(12) United States Patent  
Nofzinger

(10) Patent No.: US 11,684,510 B2  
(45) Date of Patent: Jun. 27, 2023

(54) NONINVASIVE, REGIONAL BRAIN THERMAL STIMULI FOR THE TREATMENT OF NEUROLOGICAL DISORDERS

(71) Applicant: University of Pittsburgh—Of the Commonwealth System of Higher Education, Pittsburgh, PA (US)

(72) Inventor: Eric A. Nofzinger, Allison Park, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 1211 days.

(21) Appl. No.: 16/151,243

(22) Filed: Oct. 3, 2018

(65) Prior Publication Data

US 2019/0133815 A1    May 9, 2019

Related U.S. Application Data

(63) Continuation-in-part of application No. 14/938,705, filed on Nov. 11, 2015, now Pat. No. 10,213,334.

(Continued)

(51) Int. Cl.
*A61F 7/00* (2006.01)
*A61F 7/02* (2006.01)

(Continued)

(52) U.S. Cl.
CPC ................ *A61F 7/007* (2013.01); *A61F 7/02* (2013.01); *A61F 7/10* (2013.01); *A61M 21/02* (2013.01);

(Continued)

(58) Field of Classification Search
CPC ...... A61F 2007/0002; A61F 2007/0007; A61F 2007/0008; A61F 2007/0056
See application file for complete search history.

(56) References Cited

U.S. PATENT DOCUMENTS 222,690 A    12/1879   Goldschmidt
301,931 A    7/1884    Smith et al.
(Continued)

FOREIGN PATENT DOCUMENTS

EP    0050473 A2    4/1982
EP    1977710       10/2008
(Continued)

OTHER PUBLICATIONS

Cathey; The Really Cool Mammalian Diving Reflex; 3 pages; retrieved from the internet (https://blogs.psychcentral.com/overcoming-ocd/2015/08/the-really-cool-mammalian-diving-reflex/) on Oct. 16, 2020.

(Continued)

*Primary Examiner* — Kaitlyn E Smith
(74) *Attorney, Agent, or Firm* — The Webb Law Firm

(57) ABSTRACT

Apparatuses and methods for treating neurological and/or neuropsychiatric disorders are by application of thermal energy to the patient's forehead region, for example, by maintaining a target temperature or temperature range to the forehead of a patient for a time period. In particular, described herein are regional brain cooling mechanisms to treat neuropsychiatric disorders such as depression, anxiety, and autism.

37 Claims, 13 Drawing Sheets

Related U.S. Application Data which is a continuation of application No. 14/341,642, filed on Jul. 25, 2014, now Pat. No. 9,211,212, which is a continuation-in-part of application No. 12/288,417, filed on Oct. 20, 2008, now Pat. No. 9,492,313, which is a continuation-in-part of application No. 11/788,694, filed on Apr. 20, 2007, now Pat. No. 8,236,038.

(60) Provisional application No. 61/859,161, filed on Jul. 26, 2013, provisional application No. 60/793,680, filed on Apr. 20, 2006.

(51) Int. Cl.
*A61F 7/10* (2006.01)
*A61M 21/02* (2006.01)
*A61B 17/00* (2006.01)
*A61M 21/00* (2006.01)
*A61M 16/06* (2006.01)

(52) U.S. Cl.
CPC ..... *A61B 2017/00132* (2013.01); *A61F 7/106* (2013.01); *A61F 2007/0002* (2013.01); *A61F 2007/0007* (2013.01); *A61F 2007/0054* (2013.01); *A61F 2007/0056* (2013.01); *A61F 2007/0071* (2013.01); *A61F 2007/0075* (2013.01); *A61F 2007/0076* (2013.01); *A61F 2007/0095* (2013.01); *A61M 16/0683* (2013.01); *A61M 2021/0066* (2013.01); *A61M 2205/366* (2013.01); *A61M 2205/3606* (2013.01); *A61M 2205/3673* (2013.01); *A61M 2205/59* (2013.01); *A61M 2230/10* (2013.01); *A61M 2230/50* (2013.01); *A61M 2230/60* (2013.01); *A61M 2230/63* (2013.01)

(56) References Cited

U.S. PATENT DOCUMENTS

| | | |
|---|---|---|
| 683,991 A | 10/1901 | Rowe |
| 737,473 A | 8/1903 | Porter |
| 805,371 A | 11/1905 | Meinecke et al. |
| 919,614 A | 4/1909 | Meinecke |
| 1,002,021 A | 8/1911 | Barnes |
| 1,127,221 A | 2/1915 | Finkelstein |
| 1,318,411 A | 10/1919 | Rozene |
| 1,322,984 A | 11/1919 | Wesley |
| 1,345,906 A | 7/1920 | Augustine |
| 1,511,775 A | 10/1924 | Frederic et al. |
| 1,522,295 A | 1/1925 | Gee |
| 1,567,931 A | 12/1925 | Epler |
| 1,743,244 A | 1/1930 | Shulman |
| 1,769,186 A | 7/1930 | Morris |
| 1,870,143 A | 8/1932 | Roux |
| 1,964,655 A | 6/1934 | Williamson |
| 2,049,723 A | 8/1936 | Pomeranz |
| 2,158,571 A | 5/1939 | Culp |
| 2,320,467 A | 6/1943 | Rabil |
| 2,726,658 A | 12/1955 | Chessey |
| 3,244,210 A | 4/1966 | Giacomo |
| 3,463,161 A | 8/1969 | Andrassy |
| 3,587,577 A | 6/1971 | Smirnov et al. |
| 3,696,814 A | 10/1972 | Umemoto |
| 3,717,145 A | 2/1973 | Berndt et al. |
| 3,895,638 A | 7/1975 | Ito |
| 3,908,655 A | 9/1975 | Lund |
| 3,979,345 A | 9/1976 | Yates et al. |
| 3,988,568 A | 10/1976 | Mantell |
| 4,118,946 A | 10/1978 | Tubin |
| 4,172,495 A | 10/1979 | Zebuhr et al. |
| 4,204,543 A | 5/1980 | Henderson |
| 4,356,709 A | 11/1982 | Alexander |
| 4,425,916 A | 1/1984 | Bowen |
| 4,466,439 A | 8/1984 | Moore |
| 4,483,021 A | 11/1984 | McCall |
| 4,566,455 A | 1/1986 | Kramer |
| 4,574,411 A | 3/1986 | Yagi |
| 4,691,762 A | 9/1987 | Elkins et al. |
| 4,742,827 A | 5/1988 | Lipton |
| 4,753,242 A | 6/1988 | Saggers |
| 4,765,338 A | 8/1988 | Turner et al. |
| 4,781,193 A | 11/1988 | Pagden |
| 4,844,072 A | 7/1989 | French et al. |
| 4,854,319 A | 8/1989 | Tobin |
| 4,891,501 A | 1/1990 | Lipton |
| 4,920,963 A | 5/1990 | Brader |
| 4,961,422 A | 10/1990 | Marchosky et al. |
| 5,097,828 A | 3/1992 | Deutsch |
| 5,097,829 A | 3/1992 | Quisenberry |
| 5,163,425 A | 11/1992 | Nambu et al. |
| 5,183,058 A | 2/1993 | Janese |
| 5,184,613 A | 2/1993 | Mintz |
| 5,197,466 A | 3/1993 | Marchosky et al. |
| 5,228,431 A | 7/1993 | Giarretto |
| 5,261,399 A | 11/1993 | Klatz et al. |
| 5,274,865 A | 1/1994 | Takehashi |
| 5,292,347 A | 3/1994 | Pompei |
| 5,305,470 A | 4/1994 | Mckay |
| 5,305,471 A | 4/1994 | Steele et al. |
| 5,314,456 A | 5/1994 | Cohen |
| 5,327,585 A | 7/1994 | Karlan |
| 5,342,411 A | 8/1994 | Maxted et al. |
| 5,344,437 A | 9/1994 | Pistay |
| 5,356,426 A | 10/1994 | Delk et al. |
| 5,400,617 A | 3/1995 | Ragonesi et al. |
| 5,409,500 A | 4/1995 | Dyrek |
| 5,441,476 A | 8/1995 | Kitado et al. |
| 5,469,579 A | 11/1995 | Tremblay et al. |
| 5,531,777 A | 7/1996 | Goldstein et al. |
| 5,545,199 A | 8/1996 | Hudson |
| 5,603,728 A | 2/1997 | Pachys |
| 5,609,619 A | 3/1997 | Pompei |
| 5,643,336 A | 7/1997 | Lopez-Claros |
| 5,653,741 A | 8/1997 | Grant |
| 5,658,324 A | 8/1997 | Bailey, Sr. et al. |
| 5,715,533 A | 2/1998 | Stein |
| 5,755,756 A | 5/1998 | Freedman, Jr. et al. |
| 5,837,002 A | 11/1998 | Augustine et al. |
| 5,848,981 A | 12/1998 | Herbranson |
| 5,867,999 A | 2/1999 | Bratton et al. |
| 5,871,526 A | 2/1999 | Gibbs et al. |
| 5,895,418 A | 4/1999 | Saringer |
| 5,897,581 A | 4/1999 | Fronda et al. |
| 5,897,582 A | 4/1999 | Agnatovech et al. |
| 5,916,242 A | 6/1999 | Schwartz |
| 5,948,012 A | 9/1999 | Mahaffey et al. |
| 5,950,234 A | 9/1999 | Leong et al. |
| 5,957,963 A | 9/1999 | Dobak, III |
| 5,957,964 A | 9/1999 | Ceravolo |
| 6,010,528 A | 1/2000 | Augustine et al. |
| 6,017,337 A | 1/2000 | Pira |
| 6,030,412 A | 2/2000 | Klatz et al. |
| 6,051,019 A | 4/2000 | Dobak, III |
| 6,083,254 A | 7/2000 | Evans |
| 6,113,626 A | 9/2000 | Clifton et al. |
| 6,126,680 A | 10/2000 | Wass |
| 6,156,057 A | 12/2000 | Fox |
| 6,156,059 A | 12/2000 | Olofsson |
| 6,183,501 B1 | 2/2001 | Latham |
| 6,197,045 B1 | 3/2001 | Carson |
| 6,228,376 B1 | 5/2001 | Misumi et al. |
| 6,230,501 B1 | 5/2001 | Bailey, Sr. et al. |
| 6,231,595 B1 | 5/2001 | Dobak, III |
| 6,248,126 B1 | 6/2001 | Lesser et al. |
| 6,277,143 B1 | 8/2001 | Klatz et al. |
| 6,295,819 B1 | 10/2001 | Mathiprakasam et al. |
| 6,312,453 B1 | 11/2001 | Stefanile et al. |
| 6,363,285 B1 | 3/2002 | Wey |
| 6,375,673 B1 | 4/2002 | Clifton et al. |
| 6,375,674 B1 | 4/2002 | Carson |
| 6,409,746 B1 | 6/2002 | Igaki et al. |
| 6,416,532 B1 | 7/2002 | Fallik |

(56) References Cited

U.S. PATENT DOCUMENTS

| | | |
|---|---|---|
| 6,461,379 B1 | 10/2002 | Carson et al. |
| 6,500,201 B1 | 12/2002 | Tsuchiya et al. |
| 6,511,502 B2 | 1/2003 | Fletcher |
| 6,516,624 B1 | 2/2003 | Ichigaya |
| 6,523,354 B1 | 2/2003 | Tolbert |
| 6,551,347 B1 | 4/2003 | Elkins |
| 6,554,787 B1 | 4/2003 | Griffin et al. |
| 6,581,400 B2 | 6/2003 | Augustine et al. |
| 6,599,312 B2 | 7/2003 | Dobak, III |
| 6,610,084 B1 | 8/2003 | Torres |
| 6,629,990 B2 | 10/2003 | Putz et al. |
| 6,669,715 B2 | 12/2003 | Hoglund et al. |
| 6,673,098 B1 | 1/2004 | Machold et al. |
| 6,682,552 B2 | 1/2004 | Ramsden et al. |
| 6,692,518 B2 | 2/2004 | Carson |
| 6,699,267 B2 | 3/2004 | Voorhees et al. |
| 6,736,837 B2 | 5/2004 | Fox |
| 6,740,109 B2 | 5/2004 | Dobak, III |
| 6,740,110 B2 | 5/2004 | Babcock |
| 6,770,085 B1 | 8/2004 | Munson |
| 6,845,520 B2 | 1/2005 | Kim |
| 6,854,128 B1 | 2/2005 | Faulk |
| 6,881,219 B1 | 4/2005 | Agarwal et al. |
| 6,921,374 B2 | 7/2005 | Augustine |
| 6,929,656 B1 | 8/2005 | Lennox |
| 6,962,600 B2 | 11/2005 | Lennox et al. |
| 6,979,345 B2 | 12/2005 | Werneth |
| 7,008,445 B2 | 3/2006 | Lennox |
| 7,044,960 B2 | 5/2006 | Voorhees et al. |
| 7,052,509 B2 | 5/2006 | Lennox et al. |
| 7,056,334 B2 | 6/2006 | Lennox |
| 7,077,858 B2 | 7/2006 | Fletcher et al. |
| 7,087,075 B2 | 8/2006 | Briscoe et al. |
| 7,146,211 B2 | 12/2006 | Frei et al. |
| 7,152,412 B2 | 12/2006 | Harvie |
| 7,179,280 B2 | 2/2007 | Mills |
| 7,182,777 B2 | 2/2007 | Mills |
| 7,189,252 B2 | 3/2007 | Krueger |
| 7,229,468 B2 | 6/2007 | Wong, Jr. et al. |
| 7,309,348 B2 | 12/2007 | Streeter et al. |
| 7,559,907 B2 | 7/2009 | Krempel et al. |
| 7,637,931 B2 | 12/2009 | Heaton |
| 7,744,640 B1 | 6/2010 | Faries, Jr. et al. |
| 7,854,754 B2 | 12/2010 | Ting et al. |
| 7,875,066 B2 | 1/2011 | Cohen et al. |
| 7,877,827 B2 | 2/2011 | Marquette et al. |
| 7,909,861 B2 | 3/2011 | Balachandran et al. |
| 7,930,772 B2 | 4/2011 | Fontanez |
| 8,052,624 B2 | 11/2011 | Buchanan et al. |
| 8,236,038 B2 | 8/2012 | Nofzinger |
| 8,425,583 B2 | 4/2013 | Nofzinger |
| 8,784,293 B2 | 7/2014 | Berka et al. |
| 9,089,400 B2 | 7/2015 | Nofzinger |
| 9,211,212 B2 | 12/2015 | Nofzinger et al. |
| 9,492,313 B2 * | 11/2016 | Nofzinger .................. A61F 7/02 |
| 9,669,185 B2 | 6/2017 | Nofzinger |
| 10,058,674 B2 | 8/2018 | Walker et al. |
| 10,227,063 B2 | 3/2019 | Abreu |
| 10,245,176 B2 | 4/2019 | Smith |
| 10,610,661 B2 * | 4/2020 | Nofzinger ............. A61M 19/00 |
| 2001/0000029 A1 | 3/2001 | Misumi et al. |
| 2001/0025191 A1 | 9/2001 | Montgomery |
| 2001/0039442 A1 | 11/2001 | Gorge et al. |
| 2001/0045104 A1 | 11/2001 | Bailey, Sr. et al. |
| 2002/0026226 A1 | 2/2002 | Ein |
| 2002/0095198 A1 | 7/2002 | Wbitebook et al. |
| 2002/0103520 A1 | 8/2002 | Latham |
| 2002/0156509 A1 | 10/2002 | Cheung |
| 2003/0109911 A1 | 6/2003 | Lachenbruch et al. |
| 2003/0130651 A1 | 7/2003 | Lennox |
| 2003/0149461 A1 | 8/2003 | Johnson |
| 2003/0171685 A1 | 9/2003 | Lesser et al. |
| 2003/0195439 A1 | 10/2003 | Caselnova |
| 2004/0010178 A1 | 1/2004 | Buckner |
| 2004/0024432 A1 | 2/2004 | Castilla |
| 2004/0049134 A1 | 3/2004 | Tosaya et al. |
| 2004/0059400 A1 | 3/2004 | Lin |
| 2004/0064170 A1 | 4/2004 | Radons et al. |
| 2004/0073280 A1 | 4/2004 | Dae et al. |
| 2004/0073281 A1 | 4/2004 | Caselnova |
| 2004/0159109 A1 | 8/2004 | Harvie |
| 2004/0171970 A1 | 9/2004 | Schleuniger et al. |
| 2004/0186541 A1 | 9/2004 | Agarwal et al. |
| 2004/0249427 A1 | 12/2004 | Nabilsi |
| 2005/0065584 A1 | 3/2005 | Schiff et al. |
| 2005/0087194 A1 | 4/2005 | Scott |
| 2005/0107851 A1 | 5/2005 | Taboada et al. |
| 2005/0131504 A1 | 6/2005 | Kim |
| 2005/0143797 A1 | 6/2005 | Parish et al. |
| 2005/0193742 A1 | 9/2005 | Arnold |
| 2006/0024358 A1 | 2/2006 | Santini et al. |
| 2006/0122673 A1 | 6/2006 | Callister et al. |
| 2006/0149119 A1 | 7/2006 | Wang |
| 2006/0161230 A1 | 7/2006 | Craven |
| 2006/0173396 A1 | 8/2006 | Hatamian et al. |
| 2006/0198874 A1 | 9/2006 | Stanley |
| 2006/0235495 A1 | 10/2006 | Tsai |
| 2006/0235498 A1 | 10/2006 | Mollendorf et al. |
| 2006/0251743 A1 | 11/2006 | Karita |
| 2006/0293732 A1 | 12/2006 | Collins et al. |
| 2007/0010861 A1 | 1/2007 | Anderson et al. |
| 2007/0055330 A1 | 3/2007 | Rutherford |
| 2007/0123758 A1 | 5/2007 | Miesel et al. |
| 2007/0207220 A1 | 9/2007 | Luedtke et al. |
| 2007/0247009 A1 | 10/2007 | Hoffmann et al. |
| 2007/0282249 A1 | 12/2007 | Quisenberry et al. |
| 2007/0282406 A1 | 12/2007 | Dow |
| 2008/0015665 A1 | 1/2008 | Lachenbruch |
| 2008/0033518 A1 | 2/2008 | Rousso et al. |
| 2008/0046026 A1 | 2/2008 | Pless et al. |
| 2008/0046047 A1 | 2/2008 | Jacobs |
| 2008/0097560 A1 | 4/2008 | Radziunas et al. |
| 2008/0097561 A1 | 4/2008 | Melsky et al. |
| 2008/0103568 A1 | 5/2008 | Dow |
| 2008/0140096 A1 | 6/2008 | Svadovskiy |
| 2008/0168605 A1 | 7/2008 | Wolske |
| 2008/0188915 A1 | 8/2008 | Mills et al. |
| 2008/0228248 A1 | 9/2008 | Guyuron et al. |
| 2008/0249439 A1 | 10/2008 | Tracey et al. |
| 2008/0249520 A1 | 10/2008 | Dunning et al. |
| 2008/0269852 A1 | 10/2008 | Lennox et al. |
| 2008/0288033 A1 | 11/2008 | Mason et al. |
| 2008/0300529 A1 | 12/2008 | Reinstein |
| 2009/0024043 A1 | 1/2009 | MacLeod et al. |
| 2009/0049694 A1 | 2/2009 | Morris |
| 2009/0198311 A1 | 8/2009 | Johnson et al. |
| 2009/0236893 A1 | 9/2009 | Ehlers et al. |
| 2009/0306748 A1 | 12/2009 | Mollendorf et al. |
| 2009/0312676 A1 | 12/2009 | Rousso et al. |
| 2009/0312823 A1 | 12/2009 | Patience et al. |
| 2010/0030306 A1 | 2/2010 | Edelman et al. |
| 2010/0087701 A1 | 4/2010 | Berka et al. |
| 2010/0122398 A1 | 5/2010 | Luciano |
| 2010/0198281 A1 | 8/2010 | Chang et al. |
| 2010/0198318 A1 | 8/2010 | Rogers |
| 2010/0211142 A1 | 8/2010 | Rogers et al. |
| 2010/0241200 A1 | 9/2010 | Bruder et al. |
| 2010/0312317 A1 | 12/2010 | Baltazar |
| 2010/0331752 A1 | 12/2010 | Cumming et al. |
| 2011/0125233 A1 | 5/2011 | Shen et al. |
| 2011/0184502 A1 | 7/2011 | Bruder |
| 2011/0218421 A1 | 9/2011 | Hempel et al. |
| 2011/0282269 A1 | 11/2011 | Quisenberry et al. |
| 2012/0150268 A1 | 6/2012 | Doherty et al. |
| 2012/0302942 A1 | 11/2012 | DiPierro et al. |
| 2012/0310312 A1 | 12/2012 | Yee |
| 2013/0007945 A1 | 1/2013 | Krondahl |
| 2013/0008181 A1 | 1/2013 | Makanis et al. |
| 2013/0103125 A1 | 4/2013 | Radspieler et al. |
| 2013/0131464 A1 | 5/2013 | Westbrook et al. |
| 2013/0202668 A1 | 8/2013 | Prost et al. |
| 2013/0289680 A1 | 10/2013 | Hasegawa |
| 2014/0303698 A1 | 10/2014 | Benyaminpour et al. |
| 2014/0343069 A1 | 11/2014 | Laiji et al. |

(56) References Cited

U.S. PATENT DOCUMENTS

| | | |
|---|---|---|
| 2015/0101788 A1 | 4/2015 | Smith et al. |
| 2015/0105687 A1 | 4/2015 | Abreu |
| 2015/0238725 A1 | 8/2015 | Tucker et al. |
| 2015/0283353 A1 | 10/2015 | Kohn et al. |
| 2016/0128864 A1 | 5/2016 | Nofzinger et al. |
| 2016/0151199 A9 | 6/2016 | Gil et al. |
| 2016/0361356 A1 | 12/2016 | Roth et al. |
| 2016/0361515 A1 | 12/2016 | Jung et al. |
| 2017/0252534 A1 | 9/2017 | Nofzinger |
| 2017/0319815 A1 | 11/2017 | Nofzinger et al. |
| 2017/0333667 A1 | 11/2017 | Tucker |
| 2018/0200476 A1 | 7/2018 | Tucker et al. |
| 2019/0275287 A1 | 9/2019 | Nofzinger |

FOREIGN PATENT DOCUMENTS

| | | |
|---|---|---|
| EP | 2359781 | 8/2011 |
| GB | 460200 A | 1/1937 |
| GB | 461294 A | 2/1937 |
| JP | UM2-20522 | 2/1990 |
| JP | 10-192331 | 7/1998 |
| JP | H11-001428 A | 1/1999 |
| JP | 11-042282 | 2/1999 |
| JP | 2002536069 A | 10/2002 |
| JP | 2003164496 | 6/2003 |
| JP | 2003260080 A | 9/2003 |
| JP | 2004189999 A | 7/2004 |
| JP | 2005124609 A | 5/2005 |
| JP | 3730096 B | 10/2005 |
| JP | 2005274013 | 10/2005 |
| JP | 2006102020 | 4/2006 |
| JP | 20007175476 A | 7/2007 |
| WO | WO90/01911 A1 | 3/1990 |
| WO | WO92/20309 A1 | 11/1992 |
| WO | WO94/00086 A1 | 1/1994 |
| WO | WO95/10251 A1 | 4/1995 |
| WO | WO96/10379 A2 | 4/1996 |
| WO | WO96/31136 A1 | 10/1996 |
| WO | WO97/36560 A1 | 10/1997 |
| WO | WO98/56310 A1 | 12/1998 |
| WO | WO99/08632 A1 | 2/1999 |
| WO | WO00/03666 A1 | 1/2000 |
| WO | WO00/09052 A1 | 2/2000 |
| WO | WO01/39704 A1 | 6/2001 |
| WO | WO02/05736 A2 | 1/2002 |
| WO | WO02/34177 A1 | 5/2002 |
| WO | WO03/092539 A2 | 11/2003 |
| WO | WO2004/065862 A2 | 8/2004 |
| WO | WO2004/111741 A1 | 12/2004 |
| WO | WO2005/007060 A2 | 1/2005 |
| WO | WO2005/076806 A2 | 8/2005 |
| WO | WO2005/120428 A1 | 12/2005 |
| WO | WO2006/073915 A2 | 7/2006 |
| WO | WO2006/086086 A2 | 8/2006 |
| WO | WO2007/005026 A1 | 1/2007 |
| WO | WO2007/101039 A1 | 9/2007 |
| WO | WO2008/099017 A1 | 8/2008 |
| WO | WO2008/129357 A2 | 10/2008 |
| WO | WO2008/142650 A1 | 11/2008 |
| WO | WO2008/151260 A2 | 12/2008 |
| WO | WO2009/073208 A1 | 6/2009 |
| WO | WO2009/122336 A1 | 10/2009 |
| WO | WO2009/147413 A1 | 12/2009 |
| WO | WO2011/161571 A1 | 12/2011 |
| WO | WO2012/012683 A1 | 1/2012 |
| WO | WO2012/028730 A1 | 3/2012 |
| WO | WO2012/083151 A1 | 6/2012 |
| WO | WO2015/071810 A1 | 5/2015 |
| WO | WO2015/148411 A1 | 10/2015 |
| WO | WO2016/025323 A1 | 2/2016 |
| WO | WO2017/030851 A2 | 2/2017 |

OTHER PUBLICATIONS

Schenck; How to Calm Down for Extreme Emotions in 30 Seconds; 20 pages; retrieved from the internet (https://www.mindfulnessmuse.com/dialectical-behavior-therapy/how-to-calm-down-from-extreme-emotions-in-30-seconds) on Oct. 16, 2020.

Zhang et al.; Carbon nano-ink coated open cell polyurethane foam with micro-architectured multilayer skeleton for damping applications. RSC Advances; 6(83); pp. 80334-80341; Aug. 17, 2016.

Schrim et al.; U.S. Appl. No. 16/863,978 entitled "Wearable thermal devices and methods of using them," filed Apr. 30, 2020.

Bradenberger et al.; Autonomic nervous system activity during sleep in humans; Neuroendocrine Correlates of Sleep/Wakefullness; Springer, Boston, MA; ; pp. 471-485; (year of pub. sufficiently earlier than effective US filed and any foreign priority date) 2006.

Nofzinger et al.; U.S. Appl. No. 16/660,691 entitled "Noninvasive, regional brain thermal stimulation for inducing relaxation," filed Oct. 22, 2019.

Hayashi et al.; Face immersion increases vagal activity as assessed by heart rate variability; European Journal of Applied Physiology and Occupational Physiology; 76(5); pp. 394-399; Oct. 1997.

Adam et al.; Physiological and psychological differences between good and poor sleepers; J. psychiat. Res.; 20(4); pp. 301-316; Jan. 1986.

Ahiska et al.; Control of a thermoelectric brain cooler by adaptive neuro-fuzzy interference system; Instrumentation Science and Technology; vol. 36(6); pp. 636-655; Oct. 2008.

Ahmed et al.; Development of a cooling unit for the emergency treatment of head injury; World Congress on Medical Physics and Biomedical Engineering 2006; IFMBE Proceedings; vol. 14(5); Track 19; pp. 3243-3246; Aug. 2006 (copyright 2007).

Alam et al.; Local preoptic / anterior hypothalamic warming alters spontaneous and evoked neuronal activity in the magno-cellular basal forebrain; Brian Research; 696; pp. 221-230; Oct. 1995.

Alam et al.; Preoptic / anterior hypothalamic neurons: thermosensitivity in rapid eye movement sleep; Am. J. Physiol.Regul. Integr. Comp. Physiol.; 269; pp. R1250-R1257; Nov. 1995.

Alfoldi et al.; Brian and core temperatures and peripheral vasomotion during sleep and wakefulness at various ambient temperatures in the rat; Pflugers Arch.; 417; pp. 336-341; Nov. 1990.

Aschoff, Circadian Rhythms in Man, Science, vol. 148, pp. 1427-1432, Jun. 11, 1965.

Baker et al.; Persistence of sleep-temperature coupling after suprachiasmatic nuclei lesions in rats; Am. J. Physiol. Regul. Integr. Comp. Physiol.; 289(3); pp. R827-R838; Sep. 2005.

Bonnet et al.; Heart rate variability: sleep stage, time of night and arousal influences; Electroencephalography and Clinical Neurophysiology; 102(5); pp. 390-396; May 1997.

Boulant et al.; Hypothalamic neuronal responses to peripheral and deep-body temperatures; Am. J. of Physiol.; 225(6); pp. 1371-1374; Dec. 1973.

Boulant et al.; Temperature receptors in the central nervous system; Ann. Rev. Physiol.; 48; pp. 639-654; Mar. 1986.

Boulant et al.; The effects of spinal and skin temperatures on the firing rate and thermosensitivity of preoptic neurones; J. Physiol.; 240(3); pp. 639-660; Aug. 1974.

Boulant; Hypothalamic mechanisms in thermoregulation; Fed. Proc.; 40(14); pp. 2843-2850; Dec. 1981.

Brown; Toe temperature change: a measure of sleep onset?; Walking and Sleeping; 3(4); pp. 353-359; Sep.-Dec. 1979.

Clarkson et al.; Thermal neutral temperature of rats in helium-oxygen, argon-oxygen, and air; Am. J. Physiol.; 222(6); pp. 1494-1498; Jun. 1972.

Crawshaw et al.; Effect of local cooling on sweating rate and cold sensation; Pfugers Arch.; 354(1); pp. 19-27; Mar. 1975.

Diao et al., Cooling and Rewarming for Brain Ischemia or Injury: Theoretical Analysis, Annals of Biomedical Engineering, vol. 31, p. 346-353, Mar. 2003.

(56) References Cited

OTHER PUBLICATIONS

Dorr et al.; Effect of Vagus nerve stimulation on serotonergic and noradrenergic transmission; The journal of Pharmacology and experimental therapeutics; 318(2); pp. 890-898; Aug. 2006.
Gong et al.; Sleep-related c-Fos protien expression in the preoptic hypothalamus: effects of ambient warming; Am. J. Physiol. Regul. Integr. Comp. Physiol.; 279(6); pp. R2079-R2088; Dec. 2000.
Gordon; Relationship between preferred ambient temperature and autonomic thermoregulatory function in rat; Am. J. Physiol. Regul. Integr. Comp. Physiol.; 252; pp. R1130-R1137; Jun. 1987.
Gulia et al.; Ambient temperature related sleep changes in rats neonatally treated with capsaicin; Physiol. Behav.; 85(4); pp. 414-418; Jul. 21, 2005.
Guzman-Marin et al.; Discharge modulation of rat dorsal raphe neurons during sleep and waking: effects of preoptic / basal forebrain warming; Brain Res.; 875(1-2); pp. 23-34; Sep. 1, 2000.
Hajos et al.; The capsaicin sensitivity of the preoptic region is preserved in adult rats pretreated as neonates, but lost in rats pretreated as adults; Naunyn-Schmiedeberg's Arch. Pharmacol.; 324(3); pp. 219-222; Nov. 1983.
Haskell et al.; The effects of high and low ambient temperatures on human sleep stages; Electroencephalogr. Clin. Neurophysiol.; 51(5); pp. 494-501; May 1981.
Hayashi et al., The alerting effects of caffeine, bright light and face washing after a short daytime nap, Clinical Neurophysiology, 114(12), pp. 2268-2278, Dec. 2003.
Hensley et al.; 50 years of computer simulation of the human thermoregulatory system; J. Biomech. Eng.; 135(2); pp. 021005-1-021005-9; Feb. 2013.
Herrington; The heat regulation of small laboratory animals at various environmental temperatures; Am. J. of Physiol.; 129; pp. 123-139; Mar. 31, 1940.
Heuvel et al.; Changes in sleepiness and body temperature precede nocturnal sleep onset: evidence from a polsomnographic study in young men; J. Sleep Res.; 7(3); pp. 159-166; Sep. 1998.
Horne et al., Vehicle accidents related to sleep: a review, Occup Environ Med, vol. 56(5), pp. 289-294 (full text version 13 pgs.), May 1999.
Horne et al.; Exercise and sleep: body-heating effects; Sleep; 6(1); pp. 36-46; Sep. 1983.
Horne et al.; Slow wave sleep elevations after body heating: proximity to sleep and effects of aspirin; Sleep; 10(4); pp. 383-392; Aug. 1987.
Iber et al.; The AASM manual for the scoring of sleep and associatted events, the rules, terminology and technical specifications; Westchester, IL; © 2007; 57 pages; Oct. 28, 2014; retrieved from the internet (http://www.nswo.nl/userfiles/files/AASM%20-%20Manual%20for%20the%20Scoring%20ofSleep%20and%20Associted%20Events%20-%2005-2007_2.pdf).
Iwata et al., Brain temperature in newborn piglets under selective head cooling with minimal systemic hypothermia, Pediatrics International, 45(2), pp. 163-168; Apr. 2003.
John et al.; Changes in sleep-wakefulness after kainic acid lesion of the preoptic area in rats; Jpn J. Physiol.; 44; pp. 231-242; (year of pub. sufficiently earlier than effective US filing date and any foreign priority date) 1994.
John et al.; Effect of NMDA lesion of the medial preoptic neurons on sleep and other functions; Sleep; 21(6); pp. 587-598; Sep. 15, 1998.
Khubchandani et al.; Functional MRI shows activation of the medial preoptic area during sleep; NeuroImage; 26; pp. 29-35; May 15, 2005.
Krauchi et al., Circadian rhythm of heat production, heart rate, and skin and core temperature under unmasking conditions in men, American Physiological Society, 267 (3 Pt 2), pp. R819-R829, Sep. 1994.
Krauchi et al., Circadian Clues to Sleep Onset Mechanisms, Neuropsychopharmacology, vol. 25, No. S5, pp. S92-S96, Nov. 2001.
Krauchi et al., Functional link between distal vasodilation and sleep-onset latency, Am. J. Physiol. Regulatory Integrative Comp. Physiol., 278(3), pp. R741-R748, Mar. 2000.
Krauchi et al., Warm feet promote the rapid onset of sleep, Nature, vol. 401, pp. 36-37, Sep. 2, 1999.
Krilowicz et al.; Regulation of posterior lateral hypothalamic arousal related neuronal discharge by preoptic anterior hypothalamic warming; Brain Res.; 668(1-2); pp. 30-38; Dec. 30, 1994.
Kumar et al.; Ambient temperature that induces maximum sleep in rats; Physiol. Behav.; 98(1-2); pp. 186-191; Aug. 4, 2009.
Kumar et al.; Ambient temperature-dependent thermoregulatory role of REM sleep; Journal of Thermal Biology; 37(5); pp. 392-396; Aug. 2012.
Kumar et al.; Warm sensitive neurons of the preoptic area regulate ambient temperature related changes in sleep in the rat; Indian J. Physiol. Pharmacol.; 55(3); pp. 262-271; Jul.-Sep. 2011.
Kumar; Body temperature and sleep: are they controlled by the same mechanism?; Sleep and Biological Rhythms; 2(2); pp. 103-124; Jun. 2004.
Lack et al.; The rhythms of human sleep propensity and core body temperature; J. Sleep Res.; 5(1); pp. 1-11; Mar. 1996.
Lee et al.; Thermal spot over human body surface (part 1) regional difference in cold spot distribution; J. Human and Living Environment; 2(1); pp. 30-36; (year of pub. sufficiently earlier than effective US filing date and any foreign priority date) 1995.
Leshner et al., Manifestations and Management of Chronic Insomnia in Adults, NIH State-of-the-Science Conference, Final Panel Statement, Bethesda, MD, 36 pgs., Jun. 13-15, 2005.
Libert et al.; Effect of continuous heat exposure on sleep stages in humans; Sleep; 11(2); pp. 195-209; Apr. 1988.
Lu et al.; Effect of lesions of the ventrolateral preoptic nucleus on NREM and REM sleep; J. Neurosci.; 20(10); pp. 3830-3842; May 15, 2000.
Mahapatra et al.; Changes in sleep on chronic exposure to warm and cold ambient temperatures; Physiol. Behav.; 84(2); pp. 287-294; Feb. 15, 2005.
Mallick et al; Basal forebrain thermoregulatory mechanism modulates auto-regulated sleep; Frontiers in Neurology; 10.3389/fneur.2012.00102 (8 pages); Jun. 27, 2012.
McGinity et al.; Hypothalamic regulation of sleep and arousal; Frontiers in Bioscience; 8; pp. s1074-s1083; Sep. 1, 2003.
McGinity et al.; Keeping cool: a hypothesis about the mechanisms and functions of slow-wave sleep; TINS; 13(12); pp. 480-487 ; Dec. 1990.
McGinity et al.; Sleep suppression after basal forebrain lesions in the cat; Science; 160(3833); pp. 1253-1255; Jun. 14, 1968.
McKenzie/Mini-Mitter Co.; Mini-Logger® Series 2000, Physiological Data Logging Device; 510K Summary and Premarket Notification (No. K033534); 10 pgs.; Apr. 22, 2004.
Methipara et al.; Preoptic area warming inhibits wake-active neurons in the perifornical lateral hypothalamus; Brain Res.; 960(1-2); pp. 165-173; Jan. 17, 2003.
Morairty et al.; Selective increases in non-rapid eye movement sleep following whole body heating in rats; Brain Res.; 617(1); pp. 10-16; Jul. 16, 1993.
Nadel et al.; Differential thermal sensitivity in the human skin; Pflugers Arch.; 340(1); pp. 71-76; Mar. 1973.
Nakamura; Central circuitries for body temperature regulation and fever; Am. J. Physiol. Regul. Integr. Comp. Phsiol.; 301(5); pp. R1207-R1228; Nov. 2011.
Nakayama et al.; Thermal stimulation of electrical activity of single units of the preoptic region; Am. J. Physiol.; 204(6); pp. 1122-1126; Jun. 1963.
Nakayama; Single unit activity of anterior hypothalamus during local heating; Science; 134(3478); pp. 560-561; Aug. 25, 1961.
Nauta; Hypothalamic regulation of sleep in rats. An experimental study; J. Neurophysiol.; 9; pp. 285-316; Jul. 1946.
Nofzinger et al., Functional Neuroimaging Evidence for Hyperarousal in Insomnia, Am J Psychiatry, 161(11), pp. 2126-2128, Nov. 2004.
Nofzinger et al.; Alterations in regional cerebral glucose metabolism across waking and non-rapid eye movement sleep in depression; Arch. Gen. Psychiatry; 62(4); pp. 387-396; Apr. 2005.

(56) References Cited

OTHER PUBLICATIONS

Nofzinger et al.; Frontal cerebral hypothermia: A new approach to the treatment of insomnia; Sleep; Abstract Suppl.; vol. 32; abstract No. 0881; pp. A287-A288; Jun. 2009.
Nofzinger et al.; Frontal cerebral thermal transfer as a treatment for insomnia: A dose-ranging study; Sleep; Abstract Suppl.; vol. 34; abstract No. 0534; p. A183; Jun. 2011.
Nofzinger et al.; Regional cerebral metabolic correlates of WASO during NREM sleep in insomnia; J. Clinical Sleep Med.; 2(3); pp. 316-322; Jul. 2006.
Nofzinger/Cereve; SBIR/STTR Grant Submission; Feasibility of frontal cerebral hypothermia as a treatment for insomnia; submitted Dec. 9, 2008.
Obal et al.; Changes in the brain and core temperatures in relation to the various arousal states in rats in the light and dark periods of the day; Pflugers Arch.; 404(1); pp. 73-79; May 1985.
Olympic Medical; Olympic Cool-Cap System (Product Brochure); 4 pgs.; (year of pub. sufficiently earlier than effective US filing date and any foreign priority date) 2007.
Osborne et al.; Effects of hypothalamic lesions on the body temperature rhythm of the golden hamster; Neuroreport; 6(16); pp. 2187-2192; Nov. 13, 1995.
Parmeggiani et al; Hypothalamic temperature during the sleep cycle at different ambient temperatures; Electroencephalogr. and Clin. Neurophysiol.; 38(6); pp. 589-596; Jun. 1975.
Parmeggiani; Interaction between sleep and thermoregulation: an aspect of the control of behavioral states; Sleep; 10(5); pp. 426-435; Oct. 1987.
Parmeggiani et al.; Sleep and environmental temperature; Arch. Ital. Biol.; 108(2); pp. 369-387; Apr. 1970.
Poole et al.; Body temperature regulation and thermoneutrality in rats; Q. J. Exp. Physiol. Cogn. Med. Sci.; 62(2); pp. 143-149; Apr. 1977.
Raber et al.; Capsaicin 8% as a cutaneous patch (Qutenza tm): analgesic effect on patients with peripheral neuropathic pain; Acta Neurological Belgica; 115(3); pp. 335-343; Sep. 2015.
Ray et al.; Changes in sleep-wakefulness in the medial preoptic area lesioned rats: role of thermal preference; Behav. Brain Res.; 158(1); pp. 43-52; Mar. 7, 2005.
Ray et al.; Changes in thermal preference, sleep-wakefulness, body temperature and locomotor activity of rats during continuous recording for 24 hours; Behav. Brain Res.; 154(2); pp. 519-526; Oct. 5, 2004.
Raymann et al.; Diminished capability to recognize the optimal temperature for sleep initiation may contribute to poor sleep in elderly people; Sleep; 31(9); pp. 1301-1309; Sep. 2008.
Raymann et al.; Skin deep: enhanced sleep depth by cutaneous temperature manipulation; Brain; 131(PT 2); pp. 500-513; Feb. 2008.
Reyner et al., Evaluation of 'In-Car' Countermeasures to Sleepiness: Cold Air and Radio, Sleep, vol. 21(1), pp. 46-50, Jan. 1998.
Romanovsky et al.; Molecular biology of thermoregulation selected contribution: ambient temperature for experiments in rats: a new method for determining the zone of thermal neutrality; J. Appl. Phsyiol.; 92(6); pp. 2667-2679; Jun. 2002.
Schlaepfer et al.; Vagus nerve stimulation for depression: efficacy and safety in a european study; Psychological medicine; 38; pp. 651-661; May 2008.
Schmidek et al.; Influence of environmental temperature on the sleep-wakefulness cycle in the rat; Physiol. Behav.; 8(2); pp. 363-371; Feb. 1972.
Setokawa et al.; Facilitating effect of cooling the occipital region on nocturnal sleep; Sleep and Biological Rhythms; 5(3); pp. 166-172; Jul. 2007.

Sewitch; Slow wave sleep deficiency insomnia: a problem in thermo-downregulation at sleep onset; Phychophsyiology; 24(2); pp. 200-215; Mar. 1987.
Shapiro et al.; Thermal load alters sleep; Biol. Psychiatry; 26(7); pp. 736-740; Nov. 1989.
Sherin et al.; Activation of ventrolateral preoptic neurons during sleep; Science; 271(5246); pp. 216-219; Jan. 12, 1996.
Srividya et al.; Differences in the effects of medial and lateral preoptic lesions on thermoregulation and sleep in rats; Neuroscience; 139(3); pp. 853-864; Jan. 2006.
Srividya et al.; Sleep changes produced by destruction of medial septal neurons in rats; Neororeport; 15(11); pp. 1831-1835; Aug. 2004.
Sterman e tal.; Forebrain inhibitory mechanisms: sleep patterns induced by basal forebrain stimulation in the behaving cat; Exp. Neurol.; 6; pp. 103-117; Aug. 1962.
Stevens et al.; Regional sensitivity and spatial summation in the warmth sense; Physiol. Behav.; 13(6); pp. 825-836; Dec. 1974.
Stevens et al.; Temperature sensitivity of the body surface over the life span; Somatosens. Mot. Res.; 15(1); pp. 13-28; (year of pub. sufficiently earlier than effective US filing date and any foreign priority date) 1998.
Szymusiak et al.; Ambient temperature-dependence of sleep disturbances produced by basal forebrain damage in rats; Brain Res. Bull.; 12(3); pp. 295-305; Mar. 1984.
Szymusiak et al.; Maximal REM sleep time defines a narrower thermoneutral zone than does minimal metabolic rate; Physiol. Behav.; 26(4); pp. 687-690; Apr. 1981.
Szymusiak et al.; Sleep suppression following kainic acid-induced lesions of the basal forebrain; Exp. Neurol.; 94(3); pp. 598-614; Dec. 1986.
Szymusiak et al.; Sleep-related neuronal discharge in the basal forebrain of cats; Brain Res.; 370(1); pp. 82-92; Apr. 2, 1986.
Tamura et al.; Thermal spot over human body surface (part II) regional difference in warm spot distribution; J. Human and Living Environment; 2(1); pp. 37-42; (year of pub. sufficiently earlier than effective US filing date and any foreign priority date) 1995.
Thannickal et al.; Effect of ambient temperature on brain temperature and sleep-wakefulness in medial preoptic area lesioned rats; Indian J. Pharmacol.; 46(3); pp. 287-297; Jul. 2002.
Van Someren; Mechanisms and functions of coupling between sleep and temperature rhythms; Progress in Brain research; 153; pp. 309-324; Jan. 2006.
Van Someren; More than a maker: interaction between the ciradian regulation of temperature and sleep, age-related changes, and treatment possibilities; Chronobiol. Int.; 17(3); pp. 313-354; May 2000.
Von Economo; Sleep as a problem of localization; The Journal of Nervous and Mental Disease; 71(3); pp. 1-5; Mar. 1930.
Wang et al., Rapid and selective cerebral hypothermia achieved using a cooling helmet, Journal of Neurosurgery, vol. 100 No. 2, pp. 272-277 (full text version 18 pgs), Feb. 2004.
Yavuz et al.; Thermoelectric brain cooler helmet; 6th International Advanced Technologies Symposium (IATS'11); Elazig, Turkey; pp. 120-123; May 16-18, 2011.
Zhang et al.; Chronic vagus nerve stimulation improves autonomic control and attenuates systemic inflammation and heart failure progression in a canine high-rate pacing model; Circulation: Heart Failure; 2(6); pp. 692-699; Nov. 2009.
Nofzinger; U.S. Appl. No. 16/001,873 entitled "Methods and apparatuses for the thermal treatment of neurologic and psychiatric disorders," filed Jun. 6, 2018.
Walker et al.; U.S. Appl. No. 16/046,700 entitled "Systems for enhancing sleep," filed Jul. 26, 2018.

\* cited by examiner

NONINVASIVE, REGIONAL BRAIN THERMAL STIMULI FOR THE TREATMENT OF NEUROLOGICAL DISORDERS

CROSS REFERENCE TO RELATED APPLICATIONS

This application is a continuation-in-part of U.S. application Ser. No. 14/938,705, filed on Nov. 11, 2015, titled "APPARATUS AND METHOD FOR MODULATING SLEEP," now U.S. Patent Application Publication No. 2016/0128864, which is a continuation of U.S. patent application Ser. No. 14/341,642, filed on Jul. 25, 2014, titled "APPARATUS AND METHOD FOR MODULATING SLEEP," now U.S. Pat. No. 9,211,212, which is a continuation-in-part of U.S. patent application Ser. No. 12/288,417, filed on Oct. 20, 2008, titled "METHOD AND APPARATUS OF NON-INVASIVE, REGIONAL BRAIN THERMAL STIMULI FOR THE TREATMENT OF NEUROLOGICAL DISORDERS," now U.S. Pat. No. 9,492,313, which is a continuation-in-part application of U.S. patent application Ser. No. 11/788,694, filed on Apr. 20, 2007, titled "METHOD AND APPARATUS OF NONINVASIVE, REGIONAL BRAIN THERMAL STIMULI FOR THE TREATMENT OF NEUROLOGICAL DISORDERS," now U.S. Pat. No. 8,236,038, which claims priority to U.S. Provisional Patent Application No. 60/793,680, filed on Apr. 20, 2006, and titled METHOD AND APPARATUS OF BRAIN COOLING FOR THE TREATMENT OF NEUROLOGICAL DISORDERS," each of which is herein incorporated by reference in its entirety.

U.S. patent application Ser. No. 14/341,642 also claims priority to U.S. Provisional Patent Application No. 61/859,161, filed on Jul. 26, 2013, and titled "APPARATUS AND METHOD FOR MODULATING SLEEP," which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The apparatus and methods described herein may be used to treat a patient suffering from a neuropsychiatric disorder by non-invasively regulating regions of the brain. In particular, described herein are non-invasive regional brain cooling methods and apparatuses for treating depression, anxiety disorders (e.g., obsessive compulsive disorder, post-traumatic stress disorder, etc.), and autism.

BACKGROUND

Non-invasive regional brain thermal stimulation for treating neurological disorders offers novel applications for neuropsychiatric disorders in which there are alterations in whole brain metabolism. Such disorders, include, by way of example but not limitation, insomnia, anxiety disorders, including obsessive compulsive disorder (OCD), sleep apnea syndrome and depression. More broadly, however, described herein are methods and apparatuses (e.g., devices, systems) that may be effective in any neurological disorder in which an alteration in metabolism in a localized area may be beneficial.

One such brain disorder is insomnia. A recent NIH State-of-the-Science Conference "Manifestations and Management of Chronic Insomnia in Adults", noted that "insomnia is the most common sleep complaint across all stages of adulthood, and for millions of people, the problem is chronic." Many health and lifestyle factors can contribute to insomnia including stress, depression, medical illnesses, pain, medications, or specific sleeping disorders. The panel concluded that "there is great need for additional research to better define the nature of chronic insomnia." While recognizing evidence from both psychological and physiological models in the etiology of insomnia, the conference encouraged more research by concluding that "the neural mechanisms underlying chronic insomnia are poorly understood . . . " and that " . . . studies aiming to identify neural mechanisms should use animal models and in vivo neural imaging approaches in people with insomnia and in individuals with normal sleep."

Existing treatments of neurological and/or sleeping disorders, including insomnia, include the use of over the counter or prescription drugs and/or behavioral treatments. Prescription drugs are known to aid patients suffering from sleeping disorders, however, these drugs can be quite expensive and potentially addicting. Some medications even become less effective as use continues. Additionally, the prescriptions can have unwanted and harmful side effects.

Other techniques to treat sleeping disorders include a variety of behavioral measures including stimulus control therapy, sleep restriction therapy, relaxation training, cognitive therapy, and sleep hygiene education. While these measures have moderate effectiveness, they are costly, require significant time to implement and require highly trained clinicians to implement.

The methods and apparatuses described herein may address these issues and those relating to other neurological disorders through the novel use of non-invasive and localized or regional thermal stimuli to the brain that helps treat neurological or neuropsychiatric disorders. In the case of sleeping disorders or depression, again as an example but not as a limitation on the full scope of the present invention, the restoration of function in the cerebral cortex plays a significant role. At the molecular and neuronal levels, hypothesized functions of sleep include the restoration of brain energy metabolism through the replenishment of brain glycogen stores that are depleted during wakefulness and the downscaling of synapses that have been potentiated during waking brain function. A homeostatic sleep drive, or pressure for sleep, is known to build throughout the waking hours and then is discharged during sleep. At the electroencephalographic (EEG) level, this is measured by EEG spectral power in the delta (0.5-4 Hz) frequency band.

These sleep-related processes have some regional specificity for the prefrontal cortex. Slow wave sleep rhythms have both thalamic and cortical components. An anterior dominance of EEG spectral power in the delta EEG spectral power range has been reported. A frontal predominance for the increase in delta power following sleep loss has been also reported. This region of the cortex also plays a prominent role in waking executive functions which are preferentially impaired following sleep deprivation. These sleep deprivation induced cognitive impairments have been related to declines in frontal metabolism after sleep loss. While cerebral metabolism declines globally from waking to NREM sleep, these declines are most pronounced in heteromodal association cortex, including the prefrontal cortex.

Insomnia is associated with global cerebral hypermetabolism. Nofzinger et al. (*Am J Psychiatry,* 2004) assessed regional cerebral glucose metabolism during both waking and NREM sleep in insomnia patients and healthy subjects using [18F] fluoro-2-deoxy-D-glucose positron emission tomography (PET). Insomnia patients show increased global cerebral glucose metabolism during sleep and wakefulness; and a smaller decline in relative metabolism from wakefulness to sleep in wake-promoting regions of the brain. In a comparison between insomnia and depressed patients, insomnia patients demonstrated increased waking relative metabolism in the prefrontal cortex. Finally, recent research has shown that the amount of wakefulness after sleep onset, or WASO, in insomnia patients correlates with increasing metabolism in the prefrontal cortex during NREM sleep.

The relationship between body temperature and quality of sleep generally have been described in connection with prior research in the field of sleep medicine. Heat loss, via selective vasodilatation of distal skin regions (measured by the distal minus proximal skin temperature gradient (DPG), seems to be a crucial process for the circadian regulation of core body temperature (CBT) and sleepiness (Aschoff 1956; Krauchi and Wirz-Justice 1994, 2002; Krauchi et al. 1998, 2000). Increased DPG before lights off has been noted to promote a rapid onset of sleep, suggesting a link between thermoregulatory and arousal (sleepiness) systems (Krauchi et al. 1999, 2000). Hot environments impair the sleep process including falling asleep and maintaining sleep as well as generating slow wave sleep as the increased ambient temperature interferes with the normal declines in core body temperature associated with the sleep onset process. Finally, rapid and intense temperature drops around the sleep onset or sleeping periods are expected to have an arousing effect (Horne and Reyner 1999; Hayashi et al. 2003). In contrast, the present invention minimizes such adverse effects from temperature changes through application of a less intense hypothermic stimulus over a prolonged period of time to a localized surface of the scalp. More specifically, the present invention utilizes the application of a noninvasive, regional thermal stimulus, either through warming or cooling, to the scalp of the head to adjust metabolism in the cerebral cortex underlying the stimulus and, thereby, provide treatment for neurological disorders.

Existing technologies for brain cooling involve either whole body cooling or whole brain cooling. Most commonly employed is whole body cooling. Less commonly applied is whole brain cooling, which includes some invasive techniques. Of the below-listed devices, none have been used for the treatment of neuropsychiatric disorders such as depression or anxiety disorders, or neurological disorders such as sleeping disorders including insomnia.

For example, regulation of overall body temperature in an attempt to aid patients in falling asleep is disclosed in U.S. Pat. No. 5,441,476 to Kitado et al. Prior to the present invention, however, generalized temperature regulation has not proven efficacious in the field of sleep medicine. Adverse effects of entire body cooling include: (i) infections; (ii) coagulopathy; (iii) cardiac arrhythmias; (iv) arterial hypotension; and (v) shivering (leading to anesthesia).

Also known in the art, is the cooling of a particular organ for surgical purposes as demonstrated in U.S. Pat. No. 6,979,345 B2 to Werneth. In this reference, a device performs hypothermia to a patient or a particular organ of a patient, while administering a medication to a blood vessel. Additionally, U.S. Pat. Nos. 5,957,963, 6,149,667, 6,231, 595 B1 and 6,818,011 B2 all to Dobak, III, disclose a method and apparatus for performing hypothermia of an entire selected organ without significant effect on surrounding organs or other tissues. The cooling protects the tissue from injury caused by anoxia or trauma. An advantage of these inventions is that they reduce the need for whole body cooling, but they do not address the noninvasive, regionalized thermal stimulation method of the present invention.

Brain cooling devices are also available which reduce the risk of secondary brain injury after initial brain injury to a patient. For example, see U.S. Pat. No. 6,929,656 B1 to Lennox, which teaches an apparatus and method for reducing secondary brain injury. Unlike the present invention, though, this apparatus includes an invasive brain cooling probe and a control console. The brain cooling probe cools the brain to prevent secondary injury by cooling the cerebrospinal fluid within one or more brain ventricles.

Further, U.S. Pat. No. 6,986,783 B2 to Gunn et al. teaches a method for preventing or reducing the development of delayed brain damage in a patient, comprising the steps of applying generalized cooling headwear to the patient's head, thermostatically controlling the coolant temperature within a predetermined range to maintain the brain at a temperature below normal for an extended period of time sufficient to prevent the death of neurons, glial or other cells that would otherwise die as a consequence of direct injury to the brain or other injury to the patient likely to cause injury to the brain. Unlike the present invention, this method is designed to produce whole brain cooling using temperature changes that, in the case of treatment for sleep disorders, are too severe to allow sleep to occur or be maintained. The present invention differs from this prior art in that it uses the localized or regional application of a hypothermic stimulus that, in one embodiment, is in a range that can be used for the induction and maintenance of sleep.

The related art also teaches cooling blood flowing to the brain. For example, U.S. Pat. No. 6,682,552 B2 to Ramsden et al. discloses a device and system for use in a pre-hospital setting to cool the brain after an injury. The cooling effect of this invention is specifically geared towards cooling the blood flowing through the carotid artery to the brain. Likewise, U.S. Pat. No. 5,916,242 to Schwartz discloses a neck encircling apparatus for brain cooling in firm contact with the soft tissue of the neck, and particularly in thermal contact with the carotid arteries traversing the neck. Distinct from the present invention, neither of these devices allows for regional or localized brain cooling at temperature ranges that may permit sleep and its beneficial results for treatment of certain brain disorders.

Devices for brain cooling of an infant are also known, as shown in U.S. Pat. No. 6,312,453 B1 to Stefanile et al. This device is used where the infant has suffered hypoxic shock.

U.S. Pat. No. 5,261,399 to Klatz et al. teaches a brain cooling device and method for brain cooling. The device is a helmet for positioning on the head of the patient. The cooling is intended to prevent ischemic and anomic injuries whereby the patient survives neurologically intact. Another example is demonstrated in U.S. Pat. No. 7,008,445 B2 to Lennox, which teaches a cooling helmet. In both of these disclosures, generalized cooling of the brain occurs by a helmet that encompasses the entirety of a head region, while the present invention, again, focuses on localized or regional cooling or warming of the brain.

Similarly, U.S. Pat. No. 6,126,680 to Wass which discloses a method and apparatus for generalized convective cooling of a brain in which cooled air is passed over the entirety of a patient's head resulting in convective cooling of the patient's brain.

More generally, while direct application of a thermal stimulus to the cerebral cortex is not feasible in human clinical trials, general research on brain cooling has shown that the application of a cooling stimulus to the scalp decreases brain temperature in the underlying cortex in both animals and humans. For example, in a study of pigs, even a mild surface cooling of 15 degrees Celsius was associated with cooling of the scalp and superficial brain to 35 degrees Celsius. Iwata et al Pediatric Int. 2003. In this study, there was a notable differential effect of surface cooling on superficial vs. deep brain tissue, with superficial brain tissue cooled to a greater degree than deep brain tissue. The change in underlying brain temperature was achieved in 30-75 minutes. In a human study, (Wang et al. 2004) researchers were able to decrease surface brain temperatures by an average of 1.84 degrees Celsius within 1 hour of subjects wearing a whole head cooling helmet. Systemic hypothermia (<36 degrees Celsius) did not occur until 6.67 hours after application of the cooling stimulus. Biomedical engineering models (Diao et al. 2003) also suggest that rapid cooling (within 26 minutes) of the brain gray matter can be achieved by selective head cooling on the surface. While the purpose of this research focused on techniques for generalized brain cooling, the present invention specifically utilizes non-invasive and regionalized thermal stimulation, including brain cooling for the purposes of reducing brain metabolism in a specific brain region and not others, and thereby provides treatment for neurological disorders.

Prior to the present invention, generalized brain cooling has been known only to protect the brain against damage caused by loss of blood flow or loss of oxygen to brain tissue in several clinical circumstances such as head trauma, stroke and protection against neuronal insult during cardiopulmonary surgery. Preclinical studies have shown neuroprotective beneficial effects of brain cooling in several domains. These include: metabolism (1970); pH (1992); neurotransmitter levels (1982); free fatty acids (1989); blood-brain barrier (1990); edema (1987); glucose metabolism (1987); cerebral blood flow (1954); free radical activation (1994); lipid peroxidation (1994); calcium accumulation (1992); protein synthesis (1991); protein kinase-C activity (1991); leukocyte accumulation (1991); platelet function (1987); NMDA neurotoxicity (1991); growth factors (1994); cytoskeletal proteins (1993); calcium-dependent protein phosphorylation (1990); warm shock protein (1992); immediate early genes (1996); NOS activity (1999); and MMP expression (2003).

Further, the benefit of mild (30 degrees Celsius-34 degrees Celsius) hypothermia in global and focal ischemia has been recognized. Therapeutic hypothermia to improve neurological outcome after global and focal ischemic events affecting the brain has also shown beneficial results in controlled animal and human studies. However, no practical device for or method of treatment of neurological disorders has resulted from these studies.

The present invention provides methods of noninvasive, regional brain thermal stimulation to aid in the treatment of neurological or neuropsychiatric disorders that have not been utilized in the prior art. In fact, nothing in the related art patents discloses or suggests any teaching regarding the treatment of neurological disorders, including but not limited to sleeping disorders, via regional brain cooling or warming. The related art further does not provide an apparatus for regional brain thermal adjustment to treat neurological disorders, such as sleeping disorders, depression, anxiety disorders, or autism.

SUMMARY OF THE DISCLOSURE

Described herein are methods and apparatuses for non-invasive regional brain thermal stimulation for treating neurological disorders. In particular, the present methods and apparatuses may provide novel applications for neuropsychiatric disorders in which there are alterations in whole brain metabolism. Such disorders, include, by way of example but not limitation, insomnia, anxiety disorders (including generalize anxiety disorder, or GAD, obsessive compulsive disorder, or OCD, panic disorder, post-traumatic stress disorder, or PTSD, and social phobia or social anxiety disorders), sleep-specific disorders (including apnea syndrome), depression, and autism. More broadly, however, the present invention is effective in any neurological disorder in which an alteration in metabolism in a localized area may be beneficial.

The methods and apparatuses described herein may provide the advantages of delivering regionally selective brain cooling or warming in a noninvasive manner that alters cerebral metabolism in a regionally localized manner, and, thereby, treat neurological disorders that are characterized by regionally specific alterations in brain function.

Another advantage and purpose of the present invention is the delivery of thermal stimuli, either hypothermal, i.e., cooling or hyper-thermal, i.e., warming, to a more regionally select area of the cortex that allows for a more specific delivery of treatment to regions of the cortex that are known to have abnormal metabolism in specific neuropsychiatric disorders. No devices, aside from the regional brain thermal stimuli device of the present invention, currently exist for the treatment of neuropsychiatric disorders, including but not limited to insomnia, depression, anxiety, and autism, along with others. Regionally selective cooling reduces the adverse effects of whole body cooling such as: infections; coagulopathy; cardiac arrhythmia; arterial hypotension; and shivering (leading to anesthesia).

An object of the present invention is to treat neurological disorders; the methods and apparatuses described herein may focus on the pathophysiology underlying those disorders.

By way of example, but not limitation, insomnia is one of the potentially numerous, neurological disorders that has been identified to have regionally specific alterations in cerebral metabolism. In the context of treating insomnia, an object of the present invention is to provide frontal hypothermic regional cerebral thermal therapy (RCTT) that decreases metabolism in the prefrontal cortex at an optimal time. In this same content, yet another object of the present invention is to provide frontal hypothermic RCTT that positively impacts clinical outcomes by (i) decreasing cognitive arousal, (ii) accelerating the normal drop in core body temperature, (iii) differentially reducing frontal scalp temperature in relation to occipital temperature, (iv) reducing the latency to sleep or increasing sleep quantity when measured either subjectively or objectively by polysomnography, and/or (v) increasing subjective sleepiness. Again, this is only one example of a variety of regions of the brain that the present invention might target, and other configurations could be developed for regionally altering temperature in other areas.

More broadly, the present invention includes a method and device that provides regional brain cooling or warming for treatment of neurological disorders and that accomplishes desired clinical outcomes. Specifically, what is provided is a method and device for treating neurological or neuropsychiatric disorders, comprising the steps of applying a regional brain thermal stimuli device to a patient that cools or warms the scalp and skull and portions of the underlying brain of said patient. This cooling or warming alters the temperature of a cortical surface inside of the skull. Any neuropsychiatric disorder in which a change in regional metabolism may serve as an intervention could potentially be treated with the methods of the present invention.

In the embodiment of the invention having application in the treatment of anxiety, for example, the method comprises applying cooling to the forehead and temporal region of the skull, scalp or head of a patient. In this embodiment, the regional brain cooling device can optionally be combined with another anxiety therapy, including pharmaceutical treatments. The general method further includes utilizing optimal cooling times and temperatures as needed to address specified neurological disorders. For example, but not by way of limitation, in the case of insomnia and sleep disorders, the regional brain cooling device can be applied prior to, during, and/or prior to and during sleep. Also in an embodiment of the invention having application in the treatment of neuropsychiatric disorders such as depression and anxiety disorders, and including insomnia and sleep disorders, cooling is generally in the range of about 0 degrees Celsius to 37 degrees Celsius (and more specifically, between a lower range of about 5° C., 7° C., 9° C., 10° C., 12° C., 13° C., 14° C., 15° C., 17° C., 18° C., and an upper range of about 20° C., 22° C., 24° C., 25° C., 27° C., 28° C., 30° C., 32° C., etc., such as between about 5° C. and about 30° C., about 10° C., and about 28° C., about 10 degrees C. and 30 degrees C., etc.). The patient may be awake or asleep. In waking patients, the method may include feedback adjusting the temperature applied based on one or more inputs, including brain (e.g., neuro-electric readings, EEGs, etc.), patient adjustments, etc. Temperature ranges for cooling can be varied depending on the response of the patient and the desired clinical results. For example, in patient's with anxiety, the therapies (e.g, thermal control) described herein, may be applied while awake. The awake patient may be standing, sitting up, reclining, or laying down. In some variations, the awake patient may be ambulatory (e.g., moving around) and/or engaged in moderate activity (e.g., reading, talking, watching entertainment, etc.).

In an embodiment of the invention having application across the time periods of both pre-sleep and sleep, the present invention can provide a programmable feature may alter the temperature set point at specific times of waking and sleep to optimize the entry into sleep and the maintenance of sleep. The method can, optionally, further comprise the step of monitoring the patient during treatment and/or the cooling process so that temperature adjustments can be made to correspond with the specific state of wakefulness or sleep that the patient is in.

Also, specifically provided is a device for regional brain thermal stimulation for the treatment of neurological disorders, comprising a cover or shield having a shape that corresponds to the underlying brain region that is targeted for modifying cerebral temperature and metabolism; a cooling or warming element or material for brain cooling or warming located within said cover or shield; and a means for application of said regional brain cooling or warming device to a patient. The device can be comprised of a comfortable material that can be adjustable to fit a plurality of patients. The apparatus provides thermal stimulation by any method that cools or warms and serves the functional goal of noninvasive, localized temperature control for the treatment of neurological disorders, including, but not limited to: circulating coolant or warmed fluids including liquids and gasses, non-circulating materials or compounds that either apply cooling or heating or remove cold or warm including cold packs and chemical cooling or warming, and thermoelectric cooling or warming.

In some variations, the methods and apparatuses describe herein may apply warming. For example, the apparatuses and methods, including methods of using the apparatus to treat a neurological disorder may apply and maintain one or more target "warm" temperatures to a patient's forehead for a time period. The target temperature may be between 25° C. and 42° C. (including, e.g., 27° C.-40° C., 30° C.-40° C., 32° C.-40° C., 34° C.-40° C., such as 27° C., 28° C., 29° C., 30° C., 31° C., 32° C., 33° C., 34° C., 35° C., etc.). The target temperature may generally be a fixed amount greater than ambient temperature (but, in some variations, less than 40° C.). In any of the variations described herein, the time period may be a fixed time period or a variable time period. Generally, the time period is more than 15 minutes, more than 30 min, more than 1 hour, more than 2 hours, more than 3 hours, more than 4 hours, more than 5 hours, more than 6 hours, more than 7 hours, or more than 8 hours. For example, the time period may be 30 min, 1 hour, 2 hours, 3 hours, 4 hours, 5, hours, 6 hours, 7 hours, or 8 hours. The time period may be long enough to cover an entire sleep period for the patient. The time period may be during a wake period of the patient, or may span a waking and sleeping period. In some variations, the apparatus and/or method may be configured to apply multiple periods of fixed (and different) temperatures including both warming and/or cooling. In one variation, the apparatus may provide a treatment regime that includes initially applying cooling below ambient temperature at a first temperature (e.g., between about 10° C.-28° C.) for a first time period (e.g., 1 hour), then increasing temperature to a second temperature (e.g., between about 25° C.-40° C., such as 32° C.) for a second time period (e.g., 2 hours or more). In one variations, the apparatus may provide a treatment regime that includes initially applying warming above ambient temperature at a first temperature (e.g., between about 25° C.-40° C., such as 30° C.) for a first time period (e.g., 1 hour), then increasing temperature to a second temperature (e.g., between about 25° C.-40° C., such as 32° C.) for a second time period (e.g., 2 hours or more). Additional temperatures and time intervals may be applied. As discussed below, these different treatment regimens may modulate the therapy. For example, when treating sleeping disorders it may regulate a patient's sleep patterns, including reducing sleep onset latency (due to the initial time and temperature) and reducing type 1 sleep ("light" sleep) relative to later ("deep") sleep stages.

In general, the applicators described herein may be configured to limit the region of the body to which thermal energy is applied by the applicator. This may be achieved by configuring the thermal transfer region of the applicator so that it applies thermal energy (e.g., warming) to the forehead but does not provide a substantial amount of energy to other, non-forehead regions of the face. In general, the thermal transfer region may avoid applying energy to the eye orbit region (e.g., the region beneath the eyebrows, including the perioribital and cheek regions of the face. The thermal transfer region may also be configured so that, when worn by the patient, it does not deliver a substantial amount of thermal energy to the non-facial portions of the head (such as the top and back of the head). Thus, the thermal transfer region may be configured to contact only the forehead (below the hairline or scalp in many patients). Limiting the region of the face/head over which thermal energy is to be delivered directly in this manner may improve the comfort and effect of the apparatus and method, and may reduce the amount of energy required for treatment. As used herein the forehead may refer to the region of the head above the supraorbital ridge (above the eyes) and on either side by the temporal ridge (that links the supraorbital ridge to the coronal suture); and upper boundary of the forehead is typically the hairline.

In some variations, the system includes a disposable component and a reusable component. For example, the applicator may generally be reusable, but the skin-contacting (interface) portion of the thermal applicator may be configured to be used once or a few times and then replaced. Thus, the apparatus may include a disposable interface. Any of the methods of treatment described herein may therefore include a step of placing a disposable interface on the applicator before positioning the applicator, wherein the disposable interface forms at least a part of the thermal transfer region and is configured to contact the patient's forehead. The disposable interface may cover all or part of the applicator, or it may have an adhesive or other securement to hold it to the applicator so that it contracts the skin.

As mentioned, the step of positioning the applicator may include positioning the thermal transfer region so that the thermal transfer region does not contact the top or back of the patient's head. The step of positioning the applicator may comprise positioning the thermal transfer region only against the patient's forehead.

In general, maintaining the temperature of the thermal transfer region may comprise maintaining the temperature at a target temperature. In some variations, the target temperature may be between, e.g., 5° C. and 28° C. In some variations, the target temperature may be between about 25° C. and about 40° C. In some variations, maintaining the temperature of the thermal transfer region comprises maintaining the temperature at a target temperature that is at least about 0.5° C. less than than ambient temperature. In some variations, maintaining the temperature of the thermal transfer region comprises maintaining the temperature at a target temperature for at least about 1 hour, for at least about 4 hours, and/or at a target temperature for the patient's entire sleep period.

Also described herein are methods for treating a neurological disorder in a patient. In some variations, the method may include securing a thermal transfer region of an applicator in contact with the forehead and maintaining the temperature of the thermal transfer region within a target temperature range that is between 5 and 28° C. (e.g., between about 10° C. and 28° C., etc.) for a predetermined time period (e.g., greater than 15 minutes, greater than 20 minutes, greater than 30 minutes, greater than 35 minutes, greater than 40 minutes, greater than 45 minutes, etc.).

A method for treating a neurological disorder in a patient may include: applying noninvasive, regional brain cooling to a region of a patient's head over a forehead and a temporal region of the patient's skull to locally cool the patient's forehead and the patient's temporal region by applying a temperature of between 10° C. and 28° C.; and maintaining the applied temperature between 10° C. and 28° C. to reduce brain metabolism in one or more of the patient's frontal cortex, prefrontal cortex and temporal cortex to treat the neurological disorder.

For example, a method for treating a neurological disorder in a patient may include: securing a thermal transfer region of an applicator in contact with the forehead of the patient so that the thermal transfer region does not contact the perioribtal region of the patient's face; and maintaining the temperature of the thermal transfer region within a target temperature range that is between 10° C. and 28° C. to reduce brain metabolism in one or more of the patient's frontal cortex, prefrontal cortex and temporal cortex; and thereby treating the neurological disorder.

The neurological disorder is one of: depression, anxiety (e.g., posttraumatic stress disorder (PTSD), etc.), attention deficit hyperactivity disorder (ADHD), and/or autism. For example, the neurological disorder may be Obsessive Compulsive Disorder (OCD).

In general, maintaining may include maintaining the temperature of the thermal transfer region within the target temperature range for a first predetermined time period of between 10 minutes and 4 hours (e.g., between 15 minutes and 3.5 hours, between 20 minutes and 3 hours, etc.). For example, maintaining may include maintaining the temperature of the thermal transfer region within the target temperature range for a first predetermined amount of time and then maintaining the temperature of the thermal transfer region within a target temperature range of 25 to 36° C. for a second predetermined amount of time (e.g., between 15 minutes and 3 hours, etc.). Maintaining may comprise maintaining the temperature of the thermal transfer region within the target temperature range for a predetermined amount of time that is greater than 15 minutes for at least once a day for between 1-12 weeks. In some variations, maintaining comprises maintaining the temperature of the thermal transfer region within the target temperature range for a predetermined amount of time that is greater than 15 minutes for more than 2 times per week. Maintaining the temperature of the thermal transfer region may comprise maintaining the temperature while the patient is awake, asleep and/or extending between an awake and asleep period. In some variations, maintaining comprises cooling the thermal transfer region for a predetermined amount of time using one or more of: a thermal transfer fluid, a chemical heating or cooling element, and a joule heating element.

For example, a method for treating depression in a patient may include: applying noninvasive, regional brain cooling to a region of a patient's head over a forehead and a temporal region of the patient's skull to locally cool the patient's forehead and the patient's temporal region by applying a temperature of between 10° C. and 28° C.; and maintaining the applied temperature between 10° C. and 28° C. to reduce brain metabolism in one or more of the patient's frontal cortex, prefrontal cortex and temporal cortex to treat the neurological disorder. The temperature may be maintained for greater than 15 minutes.

DETAILED DESCRIPTION

Figure 1:
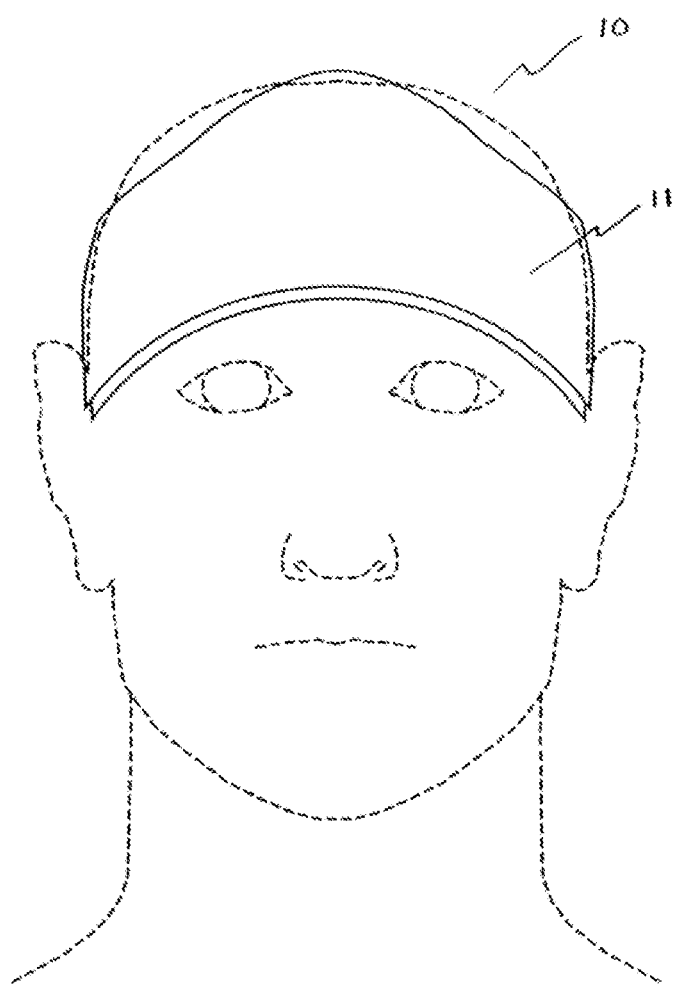
FIG. 1 displays a front view of one embodiment of the non-invasive regional brain thermal stimuli device on the head of a patient.
Figure 2:
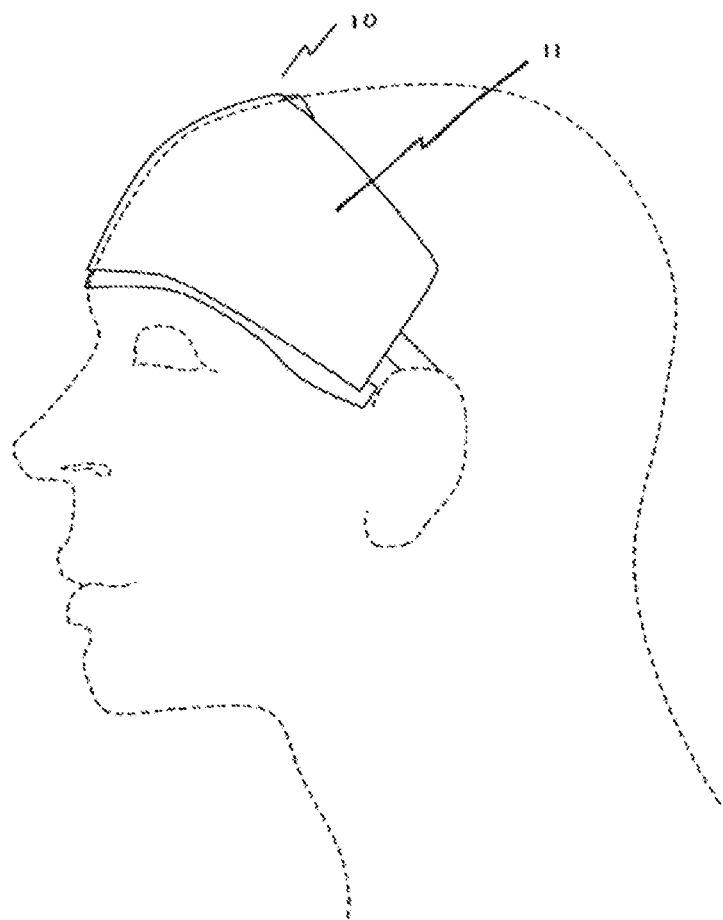
FIG. 2 shows a side view of one embodiment of the non-invasive, regional brain thermal stimuli device with an ear attachment on the head of a patient.
Figure 3:
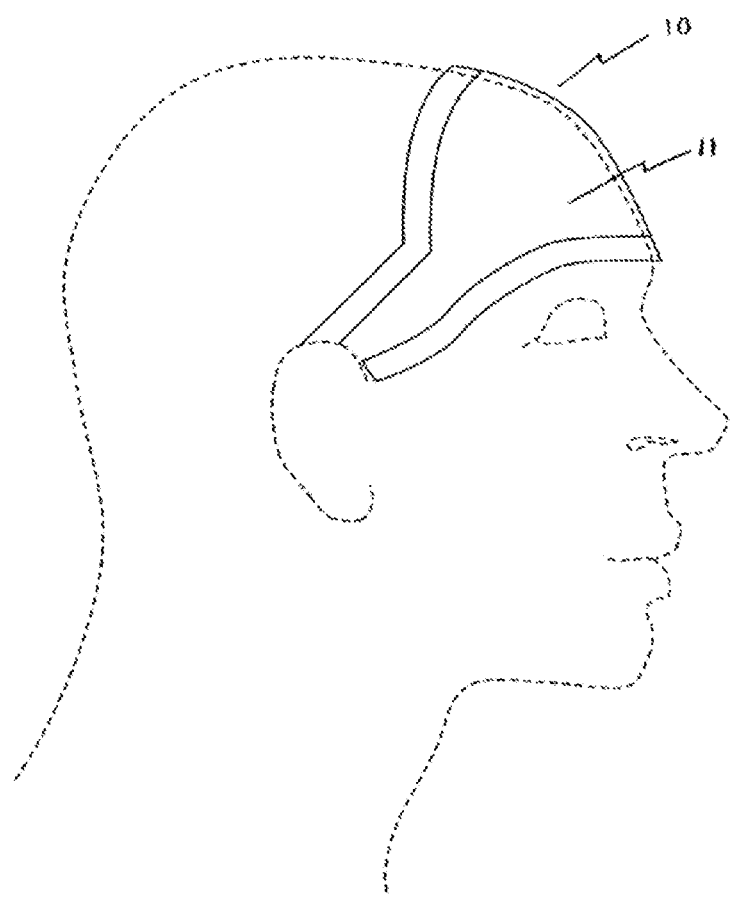
FIG. 3 illustrates a side view of one embodiment the non-invasive, regional brain thermal stimuli device with a strap attachment on the head of a patient.
Figure 4:
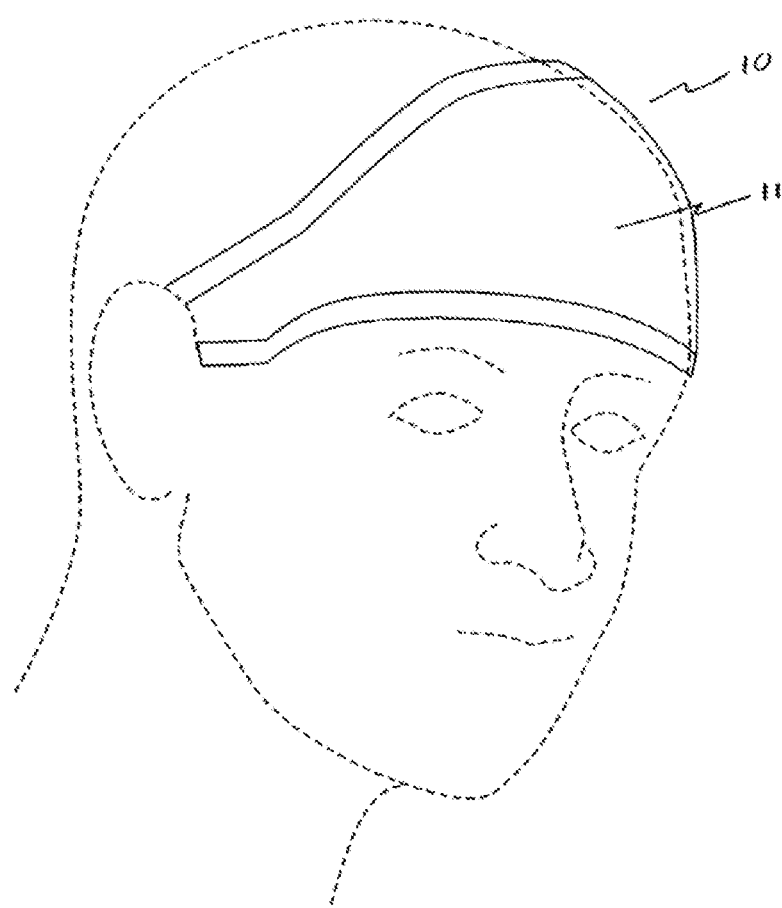
FIG. 4 shows a prospective view of one embodiment of the non-invasive, regional brain thermal stimuli device with an ear attachment, on the head of a patient.

Described herein are apparatuses (including devices and systems) that specifically control the temperature of a patient's forehead region to modulate sleep and for the treatment of neurological disorders and neuropsychiatric disorders.

The methods and apparatuses described herein will now be described in detail in relation to preferred embodiments and implementation thereof which is exemplary in nature and descriptively specific as disclosed. It must be understood that no limitation of the scope of the invention is thereby intended. The invention encompasses such alterations and further modifications in the illustrated method and apparatus, and such further applications of the principles of the invention illustrated herein, as would normally occur to persons skilled in the art to which the invention relates.

These methods may be based upon the principle that cooling or warming the scalp over certain regions of brain both triggers and maintains the physiological processes impacted by neurological disorders. For example, but not by way of limitation, cooling the prefrontal cortex of the brain can help treat the physiological processes that lead to sleep onset and sleep maintenance and thereby assist in the treatment of sleep disorders. In this example, the mechanism by which this occurs may include any or some combination of the following: 1) a reduction in metabolism in the prefrontal cortex that is necessary for the onset and maintenance of sleep; 2) a triggering of the normative drop in core body temperature that occurs as part of the sleep onset process; 3) a reduction in cognitive arousal that is mediated by increased metabolic activity in the prefrontal cortex in insomnia patients.

The method and device of this embodiment of the present invention more generally involves the application of a noninvasive, regionalized thermic stimulus to a patient's head in order to impact and adjust brain metabolism and thereby obtain the clinical benefits of treating neurological disorders.

Again by way of example, the brain cooling method and device of the present invention may obtain these benefits by decreasing hypermetabolism associated with such disorders. The brain cooling method and device of the present invention may also reduce the cognitive hyperarousal that prevents the natural entry into sleep in insomnia patients and facilitates the changes in thermoregulation associated with sleep onset. In some variations, the temperature regulation described herein may increase brain metabolism, including local brain metabolism in the frontal cortex. For example in the case of a hyper-thermic stimulus of the present invention, or non-invasive, regionalized brain warming, therapeutic benefits can be achieved where an increase to the metabolism to a localized area of a patient's brain is desired.

In general, the regional brain thermal stimuli method and device of the present invention cools or warms the scalp or skull of a patient and, in turn, cools or warms the temperature of the brain inside the skull of the patient where the invention is applied. As used in this application, the terms "regional" and "regionalized" refer to such an application of the present invention in a specific or localized area or region of the brain; and "thermal stimuli" and related variations of this phrase refer to hypothermal stimuli or cooling as well as hyper-thermal stimuli or warming. The application of a noninvasive, regionalized thermal stimulus to the scalp is associated with adjustments, i.e., reductions or increases in metabolism in the underlying cortex and such an intervention facilitates treatment of patients with neurological disorders. Again by way of example in an embodiment of the invention applying brain cooling, the invention can also facilitate sleep onset and improve sleep quality.

To help illustrate and describe the present invention, the following discussion focuses, first, on the general method of the invention and then on the general device of the present invention as they relate to brain cooling. A particular embodiment of the present invention having application to the treatment of sleep disorders such as insomnia through brain cooling is then described as one example of, but not a limitation on, the invention. Other embodiments may employ brain cooling for other regions of the brain and associated disorders, as well as brain warming for purposes of brain disorder treatment.

The method of the present invention involving a hypothermal stimuli or brain cooling generally involves the application of noninvasive, regionalized cooling to the brain, during an optimal time and at optimal temperatures, to change brain metabolism/activity in a regionally specific manner to treat brain disorders and, in particular, that is specific to each disorder based on known regional abnormalities in brain metabolism/activity found in the scientific literature for the disorder.

More specifically, the method of regional brain cooling of the present invention comprises the steps of noninvasive, regional cooling of the brain at a localized area of the brain where thermal stimulation will provide therapeutic benefits, application of such cooling at an optimal time based upon the disorder being treated and application of an optimal temperature reduction based upon the characteristics of the same disorder. The noninvasive, regional brain cooling step generally involves the use of the device of the present invention. The method of the present invention can further include the step of monitoring patient response to the cooling process and make corresponding adjustments to the timing and/or temperature of the cooling process.

Optimal timing for application of the regional thermal stimulation method of the present invention depends upon the nature of the neurological or brain disorder being treated. Optimal cooling temperatures similarly depend upon the nature of the subject disorder. The cooling method of the present invention can alternatively produce cooling cycles during use, that is, cooling can be on for a set period or periods of time and off for a set period or periods of time. The cycles are dependent on a particular patient's response to the treatments. Different cooling temperatures can also be used during treatment periods.

The thermal stimulation method of the present invention can also include the step of patient monitoring. Patients can be monitored in several ways. For example, during the application of the regionalized cooling method in a sleep laboratory setting, patients can be monitored for the presence or absence of sleep, as well as the depth of sleep as assessed by the presence of slow waves using polysomnography. Temperature probes on the surface of the scalp underneath the cooling device can monitor the temperature of the cooling and, in an alternative embodiment can provide programmed feedback to the regional brain cooling device to allow for desired temperature adjustments. This monitoring process step can also take place by any means, including electronic, known to those skilled in the art that help accomplish the functional goal of noninvasive, regionalized brain cooling for the purpose of treating neurological disorders.

The method of the present invention is used to treat disorders of the brain in which regional changes in brain activity may be beneficial. There exists a broad range of brain disorders in the fields of neurology and psychiatry, including sleep disorders associated with these neurological and psychiatric disorders, in which a change in brain activity, through regionalized brain cooling is beneficial.

For certain of these disorders, the indication is the treatment of the sleep disturbances associated with the disorders, which in turn, benefit the general condition itself. For example, in depressed patients, metabolism in the prefrontal cortex does not decline from waking to NREM sleep to the same degree as it does in healthy subjects. This abnormality in changes in regional brain metabolism across the wake/sleep period is important in either the causes of depression or in the maintenance of depression and especially in the sleep complaints often reported by these patients. Similar changes in the prefrontal cortex across the wake/sleep periods have been noted in healthy aging, and are presumed to be present in other neuropsychiatric disorders in which there is a disturbance in the ability to either fall asleep or to stay asleep during the night. Examples of such disorders include post-traumatic stress disorders, anxiety disorders, including OCD, and sleep disorders associated with aging and the dementias. The present invention also applies to treat these disorders by allowing for optimal regionalized placement, optimal cooling temperatures and optimal timing of cooling treatments that are appropriate for the disorder.

For other patients, the present invention can be applied during waking hours in connection with other neurological disorders. As an example, a neurological disorder characterized by parietal lobe metabolic abnormalities may be effectively treated by application of localized parietal scalp cooling for one hour three times per day during waking hours.

Referring to FIGS. 1-6, the noninvasive, regional brain cooling device of the present invention is comprised of a localized or regionalized item of headgear for discrete regions of the brain. The figures show configurations related to the current embodiment for cooling the frontal lobe of the brain in insomnia patients (see FIGS. 1-4) or a larger head covering (see FIGS. 5 and 6) that is positioned on the head of a patient. These same designs may also be used for treatment involving brain warming.

Referring to device to FIGS. 1-4, the thickness of cover 11 of this embodiment of device 10 can vary, and differing ranges of thickness are possible. By way of example, but not limitation, in respect to the embodiment of the present invention addressing insomnia as a neurological disorder, the preferable thickness of the device is about 0.1 inches thick to 2 inches thick and more preferably between about 0.2 inches thick and 0.5 inches thick. For other neurological disorders, thickness, again, may vary.

Figure 5:
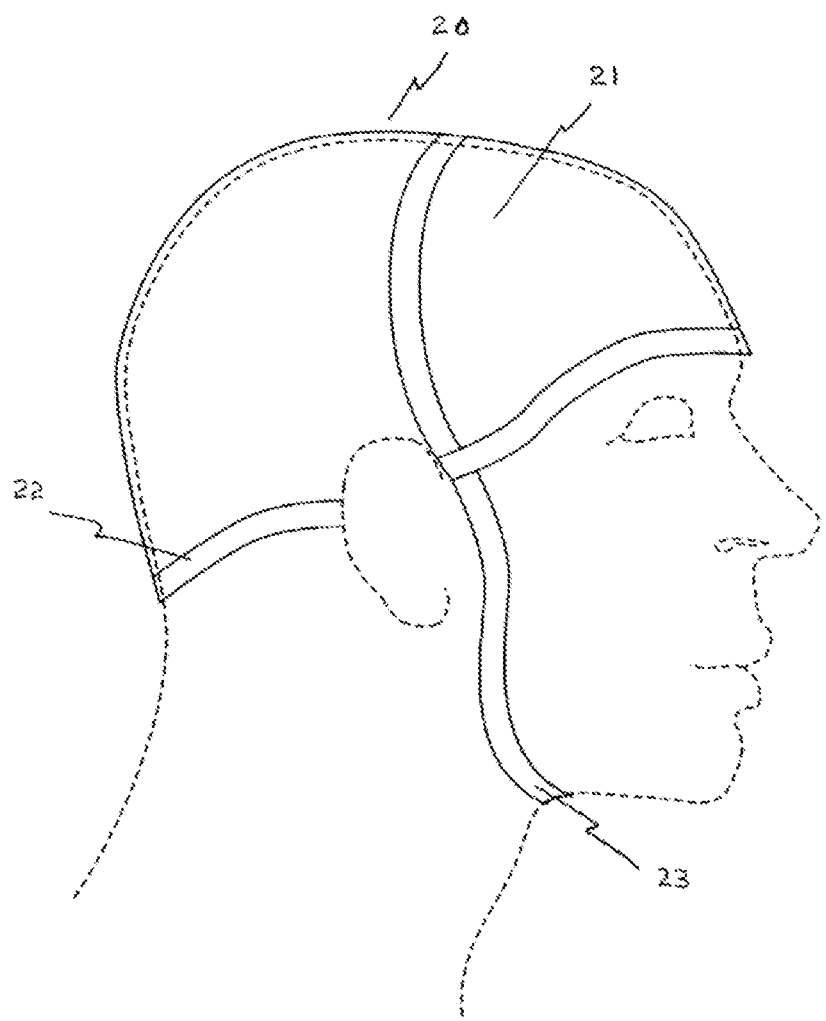
FIG. 5 shows a side view of another embodiment of the non-invasive, regional brain thermal stimuli device with a chin strap.
Figure 6:
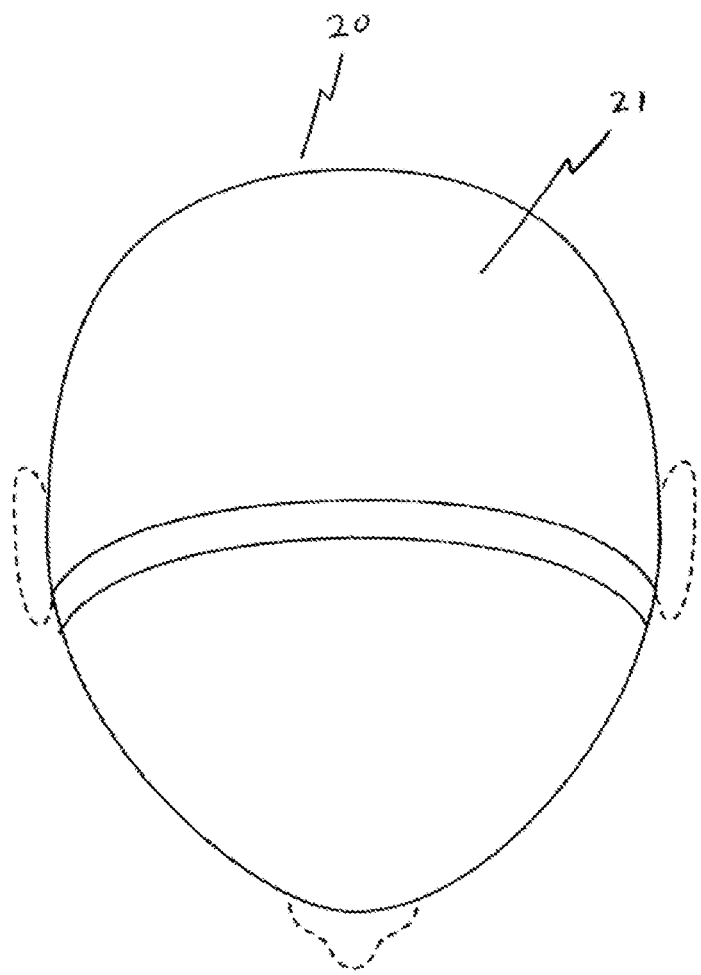
FIG. 6 illustrates a top view of another embodiment of the non-invasive, regional brain thermal stimuli device.

For embodiments of the invention as depicted in FIGS. 5 and 6, thickness of cover 21 in device 20 can also vary.

Various attachment means known to those skilled in the art can be used to attach the regional brain cooling device of the embodiments depicted in FIGS. 1-6 to a head or skull of a patient. For example and not by limitation, attachment can occur by placing straps around the ears of a patient, using one or two straps 22 which fit around the back of the head or skull of the patient, utilizing a chin strap 23, and/or using an adhesive to attach the device to the scalp of the patient or any other method of providing a wearable device. The adhesive can optionally be conductive to facilitate the cooling process. Alternatively, where the surface area of the device is sufficiently large, the device can be constructed of a stretchable cap that secures to the head or skull of a patient.

The device of the present invention is adjustable so that it can fit a plurality of different head sizes and in turn fit a plurality of patients. The apparatus accomplishes this adjustment means by any way known in the art that serves the functional goal of localized temperature control, including but not limited to snaps, Velcro or elastic.

The device of the present invention is generally placed over those regions or localized areas of the brain where cooling is desired. For example, but not by way of limitation, in an embodiment of the invention where insomnia is addressed as a neurological disorder, the device is placed on the frontal area or more particularly placed over the forehead and temporal region of the patient's skull, as shown in FIGS. 1-4. Such placement corresponds to those areas of the brain that have high levels of metabolism during sleep, i.e., the frontal and temporal cortex. For other disorders, the device of the present invention can have different sizes and/or placement on the skull of a patient.

In connection with the embodiment of the invention having application to treatment of insomnia and sleep disorders, modifications to the regional brain cooling device can be made to allow it to be used in conjunction with headgear associated with the administration of positive airway pressure treatment for sleep apnea or other sleep apnea devices, such as devices that produce a "puff" instead of constant positive pressure. These devices commonly consist of a soft plastic hollow mask that fits over the nose and/or nose and mouth of the patient. The devices also can have associated head straps attaching the masks firmly to the face of a patient and keeping the tubing that channels the air from the pressurizing machine to the mask in place.

There are a variety of configurations of headgear for holding the sleep apnea devices and/or masks in place over the oral or nasal airway passages. By way of example, but not limitation, combined sleep apnea devices and cooling headgear may consist of a variety of configurations to allow for both the holding of the mask in place as well as for the cooling of the frontal and temporal regions of the brain. In these cases, the cooling head device is configured on the inside of the headgear that holds the mask in place so that the straps for the mask keep in place both the face mask as well as the cooling device on the forehead. The straps are configured around the cooling device in such a way as to hold both the airway mask and the cooling device in place yet do not impede the circulation of fluids or gases, if any, through the cooling device.

The noninvasive, regional brain cooling of the present invention can occur using any cooling method that also serves the functional goal of localized temperature control for the treatment of neurological disorders. By way of example, but not limitation, one method of cooling is by pumping or flowing cooling fluids through the brain cooling device or optionally through a plurality of channels within the device. The terms "fluid" or "fluids" as used herein can describe a fluid, slurry or a gas or some combination thereof. By way of further example, but not limitation, where circulated cooling fluids are used, such cooling fluids can circulated by a pump or other means through a circulation system that includes a cooling chamber, insulated tubes (about 5-20 mm in diameter) that run from the chamber to the device, tube connectors on the device that allow for the connection of the tubes to the channels of the device and channels in the device (about 1-20 mm in diameter) that overlie the inner layer that is in contact with the scalp. Temperature probes on the surface of the scalp can provide feedback to the cooling chamber to adjust the temperature of the cooling fluids up or down to achieve the desired cooling temperature on the scalp. The cooling chamber may be any one of several commercially available units that allow for the cooling of fluids and pumps that circulate these fluids from the chamber to the device. The cooling chamber and pumps can be programmable to provide a range of temperatures and durations of cooling to achieve maximal cooling. The pumps also can be programmable to provide a variation to pressures of the fluids to achieve maximal cooling.

For the purposes of sleeping with the device in place, the walls of the channels for circulating the fluid are both flexible to allow for increased comfort and deformability to the contours of individual heads, yet have sufficient internal rigidity to resist compression of the channels due to the weight of a head on a pillow. The internal walls of the chamber also direct the flow of fluids evenly across the entire device to provide an even distribution of cooling over the entire surface of the device.

Another method of cooling includes passing a cooled fluid directly over the skull or scalp of a patient. Yet another method of cooling is a chemical reaction that occurs instantly between two chemicals when mixed together produces cooling. A cold pack provides an example of such a chemical reaction, but other similar reactive cooling methods can also be employed. Still another method of cooling is thermoelectric cooling based on the Peltier Effect, by which DC current is applied across two dissimilar materials causing a temperature differential.

In one embodiment of the present invention, the device consists of device having three layers. The interior layer of the apparatus fits directly on the scalp surface and is made of a material that allows for maximal comfort and that has good thermal conductive properties. The material is preferably a synthetic or the like, although other materials can be used. The middle layer optionally comprises a series of channels for circulating a fluid. The fluids may consist of a variety of elements typically used for cooling, for example, air, water, coolant or similar fluid. This middle layer can also consist of electrical refrigerant elements that produce cooling. The outer or inner layer can also house the fluid and/or channels. Further, the channels can be eliminated from the middle layer and the fluid directly flowed or pumped into and through the middle layer.

In this embodiment, the middle coolant layer is preferably designed to have varying temperatures that may differ for each individual patient according to their neurological disorder and clinical response. For example, but not as a limitation, the preferred cooling temperature in an embodiment of the invention having application to insomnia and sleep disorders ranges from about freezing (0 degrees Celsius) to just about above body temperature (about 37 degrees Celsius). Also in such an embodiment, the preferred temperature range can vary during the time of application of the device prior to sleep and throughout the sleeping period. Different behavioral states, such as waking, NREM and REM sleep, can require different temperatures in order to have maximal benefit, yet maintaining adverse events low and comfort high.

By way of example, but not limitation, an embodiment of the cooling method and device of the present invention is now described as applied to the treatment of insomnia or sleep disorders. In this embodiment, regionalized cooling preferably occurs on the frontal area of a patient's skull. Application of a cooling stimulus to the surface of the scalp decreases temperature and subsequent metabolism in the prefrontal cortex. In this content, this cooling stimulus also decreases cognitive arousal, facilitates core body temperature declines associated with sleep onset, increases depth and quality of sleep, reduces sleep onset and provides neuroprotection during sleep in sleeping disorder patients. All of these effects are associated with an improved quality of sleep and a sense of more restorative sleep.

In the embodiments of the method of this invention applicable to treatment of sleep disorders, the periods of application of cooling that are most important to help facilitate and maintain sleep include the pre-sleep period and the sleep period itself. Normal sleep is associated with a pre-sleep decline in core body temperature, a sensation of sleepiness, and a gradual loss of consciousness and a decline in cerebral metabolism overall. Regionally, this decline is notable in the prefrontal cortex. Early sleep is associated with large amounts of slow wave sleep as measured by the amounts of EEG waves that are large in amplitude and low in frequency.

Brain cooling is most appropriate at distinct times across a 24-hour day. Brain and body temperature have distinct 24-hour rhythms. The time of application of regional brain cooling is an important variable in terms of having the desired effect. For example, whole body temperature declines around the time of sleep onset. Augmentation of brain cooling over this time may aid in the transition from wake to sleep. Brain metabolism also declines across the sleep period with some increases in REM sleep.

The brain cooling device can optionally be applied, therefore, depending upon the needs of the patient, (i) only during the pre-sleep period, (ii) only during the sleep period, or (iii) both during the pre-sleep period and during the sleep period in severe cases. Further, the temperature ranges to facilitate sleep onset or to maintain sleep may differ so that programmable features for the application of different temperatures during these two periods are important.

For some patients, cooling may only be necessary in the pre-sleep period. This cooling provides the benefits of reducing core body temperature, reducing metabolic activity in the prefrontal cortex, and reducing cognitive arousal, any of which may shorten sleep latency. Once any of these listed effects occur, sleep may proceed naturally throughout the night and further cooling during sleep may not be necessary. In a preferred embodiment of the method of this invention where pre-sleep cooling is used for the treatment of insomnia or sleep disorders, the patient places the regional brain cooling device on their head within about 10 minutes to 4 hours, and preferably within about 30 minutes to an hour, of their anticipated bedtime and removes it prior to their bedtime. Variations on these time frames can also be used, though, and are within the scope of this embodiment of the invention.

For other patients, cooling may be used both prior to sleep onset and throughout the sleeping period. Such patients may have difficulty maintaining sleep because of their inability to have declines in whole brain metabolism, or in frontal metabolism and/or their inability to generate the slow wave sleep or to reduce cognitive activity associated with worries and daily preoccupations. For such patients, an extended period of cooling provides one or more of the following benefits: reduction of core body temperature, reduction of metabolic activity in the prefrontal cortex, reduction of cognitive arousal, shortening of sleep latency, increasing slow wave sleep, decreasing arousals during sleep and increasing total sleep time. In a preferred embodiment of the method of this invention relating to both pre-sleep and sleep brain cooling for treatment of insomnia and sleep disorders, the patient places the device on their head within about 10 minutes to 4 hours, and preferably within about 30 minutes to an hour, of their anticipated bedtime and continues to wear it throughout the night of sleep. While a cooler stimulus may be necessary to facilitate sleep onset (say 0 to 30 degrees Celsius), a slightly warmer temperature may be sufficient to maintain sleep (about 15 to 30 degrees Celsius), but not be too cool as to arouse a patient from sleep. Again, other time frames of application of cooling can also be used and are within the scope of this embodiment of the invention. To increase comfort, the temperature can optionally be modulated in the cooling method of the present invention from body temperature to the desired temperature range over time.

The cooling method of the present invention can also be used solely during sleep without any pre-sleep cooling.

Further, the device may be used in the middle of the night, after a patient awakens from sleep. Patients with insomnia often describe wakening in the middle of the night and having difficulty returning to sleep. At these times, the device may be applied in the middle of the night to facilitate their return to sleep.

A further feature of the device allows patients to have control over the temperature settings of the device. In this application, a control box is placed next to the bed of the patient for easy access while the patient is lying in bed. The control box is connected electrically to the thermostat of the cooling chamber and allows the patient or other users immediate access to control the temperature of the device while they are wearing it. Patients with insomnia often feel a lack of control over their ability to sleep and allowing them to have control over the temperature configuration allows for them to have immediate feedback over the temperature range of the device so they can maximize its comfort and therapeutic efficacy over repeated practice. In this manner, the temperature range is individualized for each subject to maximize comfort, minimize adverse events and maximize efficacy.

In the embodiments of the method of the present invention relating to treatment of insomnia and sleep disorders, the regional brain cooling device can operate to cool the entire time it is in contact with the patient's scalp. However, different cooling cycles and different cooling temperatures can optionally be used during pre-sleep and sleep periods. For example, different cooling temperatures can be used for NREM and for REM sleep—based upon the different degrees of internal body temperature regulation during these periods.

For purposes of treating insomnia and sleep disorders, the preferred cooling temperature for the regionalized cooling method of the present invention is between about 5 degrees Celsius to 37 degrees Celsius and preferably between about 10 degrees Celsius to 30 degrees Celsius. Other cooling temperatures can also be used, though, and are within the scope of this invention. In choosing a particular temperature, several factors should be considered. First, too cool of a temperature or stimulus has an arousing effect and interferes with the patient's sleep. Additionally, too cool of a stimulus (e.g. 0 degrees Celsius) damages scalp tissue and can produce systemic effects related to whole body cooling. Second, too warm of a stimulus is not sufficient to have significant effects on reducing metabolism in the underlying cortex and thus the patient's neurological or neuropsychiatric disorders are not effectively treated. A temperature of between about 10 degrees Celsius to 28 degrees Celsius, as an example, provides a mild, comfortable cooling that does not have any systemic effects, yet still is cool enough to produce metabolic declines in the superficial cortex in close proximity to the stimulus. At this temperature, surface, but not deep, brain tissue shows modest declines in temperature. This temperature of about 10 degrees Celsius and 28 degrees Celsius also is not associated with any adverse effects to the scalp.

The timing of the application of the cooling step in the method of the present invention also has several determinants. First, the cooling stimulus should be applied long enough so that brain cooling occurs at both the scalp and the cortex of the brain underneath the location of application. The range of this application is generally between about 20 and 150 minutes and preferably between about 30 to 60 minutes and may vary outside of these ranges according to the individual patient. For some patients, application may only need to be continued in the time prior to sleep onset in order to facilitate sleep. For other patients, application may be necessary not only prior to sleep but also during sleep.

Where regional brain cooling is applied during sleep, application of the cooling step is desirable during the first NREM sleep cycle, which generally occurs during the first 30 to 70 minutes of sleep. Other patients may require continued cooling throughout the entire period of sleep in order to decrease brain activity and facilitate sleep for this entire period.

In additional aspects, the methods of the present invention are directed to treating anxiety disorders in a patient in need of such treatment, such as patients receiving this diagnosis from their physician. The method comprises the step of applying noninvasive, regional brain cooling to a region of a patient's head associated with said anxiety disorder. In one embodiment, the anxiety disorder is obsessive compulsive disorder. Other anxiety disorders, and other disorders, such as those discussed herein above, are also within the scope of the invention. Application of cooling reduces brain metabolism in the region of the brain underlying the region of the patient's head to which said regional cooling is applied. Cooling is applied to the frontal cortex, the prefrontal cortex and/or the temporal cortex regions of the patient's brain. The patient's physiological characteristics, such as body temperature and level of sleep, can be monitored, and, optionally, temperature and/or timing of the regional brain cooling can be adjusted based upon the results of monitoring. Preferably, the cooling temperature used is between about 5 and 37° C., more preferably between about 10 and 37° C. Also preferably, the application of cooling is carried out for a period of time prior to sleep, such as up to about one hour prior to sleep. The cooling is also applied during sleep, for periods of time such as about 1, 2, 3, 4, 5, 6, 7 and 8 hours, as well as any periods of time in between these points.

In an additional aspect, the present invention is directed to methods of treating an anxiety disorder in a patient in need of such treatment, the method comprising the steps of: identifying the region of a patient's brain that is altered in connection with said disorder; identifying an optimal thermal stimulation time and temperature for altering brain function in said region; and applying noninvasive, regional brain cooling to the regional area of a patient's head over said brain region at said optimal time and temperature to alter brain function in said region. On one embodiment, the anxiety disorder is obsessive compulsive disorder. In the context of the treatment of anxiety disorders, a patient and doctor can easily determine the amount of time and the appropriate temperature for alleviation of symptoms associated with the anxiety disorder. The regional brain cooling alters the brain function in the region of the brain underlying the region of the patient's head to which said brain thermal stimuli is applied. The regional brain cooling also alters the temperature of the cortical surface of said brain region. Optionally, as described above, the patient's physiological characteristics, including body temperature and level of sleep, can be monitored, and, also optionally, the temperature and/or timing of said brain thermal stimulation can be adjusted based upon the results of said monitoring.

Preferably, the cooling temperature used is between about 5 and 37° C., more preferably between about 10 and 37° C. The application of cooling may be carried out for a period of time prior to sleep, such as up to about one hour prior to sleep. Alternatively, in some variations it may be beneficial to apply the temperature control while the patient is awake and/or during the day. In some variations, the cooling may be also applied during sleep, for periods of time such as about 1, 2, 3, 4, 5, 6, 7 and 8 hours, as well as any periods of time in between these points.

In another aspect, the present invention provides a method of lowering core body temperature in a patient in need of treatment, the method comprising the step of application of noninvasive, regional brain cooling to the frontal cortex, the prefrontal cortex and/or the temporal cortex regions of a patient's head. The application of cooling reduces brain metabolism in the region of the brain underlying the region of the patient's head to which said regional cooling is applied.

Preferably, the cooling temperature used is between about 5 and 37° C., more preferably between about 10 and 37° C. Also preferably, the application of cooling is carried out for a period of time prior to sleep, such as up to about one hour prior to sleep. The cooling is also applied during sleep, for periods of time such as about 1, 2, 3, 4, 5, 6, 7 and 8 hours, as well as any periods of time in between these points.

Optionally, as described above, the patient's physiological characteristics, including body temperature and level of sleep, can be monitored, and, also optionally, the temperature and/or timing of said brain thermal stimulation can be adjusted based upon the results of said monitoring.

Example

The invention is further described in the following example, which is not intended to limit the invention in any way.

Research Design and Methods. A within-subjects design was used to test hypotheses. The patient group included 10 patients with primary insomnia. The primary outcome measure was NREM sleep rCMRglu in the prefrontal cortex.

Design considerations. An attempt to maximize acute effects of regional cerebral thermal therapy (RCTT) was made to determine if it has an effect on reducing metabolism in the prefrontal cortex in the first NREM cycle in insomnia patients. RCTT was applied 60 minutes prior to GNT (good night time) and continued for 60 minutes after GNT. The total time of application was 120 minutes both before sleep and continuing in to the first NREM cycle.

A 14 degree centigrade cooling stimulus (50 degrees Fahrenheit) was used for an hour prior to sleep onset, followed by an 18 degree centigrade cooling stimulus once sleep onset has been achieved. In choosing a temperature, several factors were considered. First, too cool of a stimulus may have an arousing effect and may interfere with sleep. Too cool of a stimulus (e.g. 0 degrees centigrade) may also damage scalp tissue and may produce systemic effects related to whole body cooling. Second, too warm of a stimulus may not be sufficient to have effects on reducing metabolism in underlying cortex. A temperature of 14 degrees centigrade was chosen to reflect a mild, comfortable cooling that would not be expected to have any systemic effects, yet be cool enough to produce metabolic declines in superficial cortex in close proximity to the stimulus. At this temperature in pigs, for example, surface, but not deep, brain tissue showed modest declines in temperature. Also in this study, this temperature was not associated with any adverse effects to the scalp. Jennings et al (1993) alternated cold (10 degree C.) and warm (34 degree C.) stimulation via a water circulating device to the cheeks of healthy subjects throughout a night of sleep and noted preservation of sleep in relation to a no device condition. No adverse effects on skin or core body temperature were noted in that study. To minimize arousal during sleep related to excessive cooling, the bath temperature was adjusted to 18 degrees centigrade once sleep has been achieved.

The study used a normothermic (normal skin temperature of 28 degrees centigrade) circulating water control condition to control for effects on sleep simply related to wearing something on the head during sleep. Control vs. active RCTT interventions were randomized across subjects to eliminate any order effects of application.

During the treatment period, patients were seen by a study clinician and physician for therapeutic and safety monitoring. Clinical ratings included the self- and clinician-rated Clinical Global Impressions Improvement Scale. Side effects were evaluated with the Asberg Side Effects Scale. Clinical data summaries were reviewed to minimize missing data.

Tolerability Measures:
Subjective Sleepiness and Arousal
Sleepiness and arousal were measured in a variety of ways as discussed below.

Arousal
The Pre-sleep arousal scale (Nicassio et al 1985) was given 2 hours prior to usual good night time and at lights out. This measures cognitive and somatic arousal.

Sleepiness
The Stanford Sleepiness Scale was given 2 hours prior to usual good night time and at lights out. This measures sleepiness.

Subjective Sleep Onset Latency and Sleep Quality
A post-sleep inventory of subjective sleep onset and sleep quality, including awakenings and sense of sleep restoration following the control and RCTT conditions was given after the PET scan on each of the PET assessment nights.

Temperature

Temperature was assessed in the following manners.

Core Body Temperature

A temperature assessing pill was swallowed to record continuous core body temperature over 2 hours prior to sleep and continuing through the PET scans, to assess effects of the device on core body temperature. Vitalsense®) system which involves swallowing a pill which uses a tiny radio transmitter to measure core body temperature and sends the information to a belt pack worn by the subject. The pill passes through the subject undigested and is then discarded with a bowel movement. The device has been approved as safe by the U.S. Food and Drug Administration (FDA) [510(k) number K033534].

Scalp Temperature

Thermistors over the frontal and occipital cortex recorded scalp temperatures continuously over 2 hours prior to sleep and continuing through PET scan, to assess the regionally differential changes in scalp temperature in proximity to the regional cooling device.

Objective Sleep

A variety of measures of sleep were performed.

Sleep Onset Latency

Sleep onset latency was assessed on all nights using polysomnography as defined below.

EEG Spectral Power in the Delta (0.5-4 Hz Bands) During the First NREM Period

EEG sleep: EEG sleep was monitored for 4 nights at the Clinical Neuroscience Research Center (CNRC), screening for sleep apnea and periodic limb movements on night 1. Night 1 also served the purpose of accommodation to the sleep lab environment. Night 2 served as a baseline night to collect standard EEG sleep measures on the insomnia patients including measures of sleep latency, waking after sleep onset, sleep maintenance and total sleep time. On Nights 3 and 4, regional cerebral glucose metabolism was assessed using [18F]FDG PET methods during NREM sleep when subjects are using either a normothermic circulating fluid control device or the hypothermic circulating fluid. The next night was a recovery night at the subjects own home to allow for recovery from partial sleep deprivation related to the imaging procedures on night 3. On night 4 in the lab, regional cerebral glucose metabolism was assessed using [18F]-FDG PET methods during NREM sleep when subjects are using normothermic or hypothermic according to their randomization. On nights 1 and 2, subjects had IV tubing taped over 1) the antecubital area of one arm, and 2), the antecubital area or forearm of the opposite arm for accommodation to indwelling IVs used on nights 3 and 4 for bolus injection of the radioisotope and sampling of venous blood. On the third and fourth nights, subjects had normal saline infusions at a KVO infusion rate throughout the night in one antecubital vein and a vein in the opposite arm. The sleep montage on night 1 will consist of a single EEG channel (C4/A1-A2), bilateral EOGs referenced to A1-A2, bipolar submental EMG, oral-nasal thermistors, rib cage and abdominal motion sensors, single-lead EKG, fingertip oximetry, and anterior tibialis EMG. On the PET assessment nights, an expanded EEG montage (F3,F4,C4,P3,P4,O1,O2, T3,T4 each referenced to A1-A2) will be used. Manual and automated scoring of sleep was performed.

Regional Cerebral Metabolism

Regional cerebral metabolism is the primary outcome measure and was assessed using [18F]-FDG PET methods.

PET paradigms: Procedures for administration of [18F]-FDG and PET scanning were identical between the two conditions, control vs. RCTT. Prior to injection, subjects were lying in their bed in the CNRC. Two intravenous lines were placed. An intravenous line running at KVO with normal saline was placed in an antecubital vein in one arm for injection of the radionuclide. In the contralateral arm, an intravenous catheter was placed for venous sampling. For each condition, 20 minutes uptake was assessed following injection of five mCi of 18F-FDG via an antecubital IV. This was injected immediately following the first 20 minutes of sleep onset. For quantitation of absolute glucose metabolic rates, venous blood was sampled (1 ml each) at 6 evenly spaced intervals from 45 minutes to 90 minutes following the injection. Radioactivity was assayed at each interval; glucose was assayed on the first and last interval. At 60 minutes following the injection of the radionuclide, 6 consecutive 5-minute emission scans were taken, followed by a 10 minute transmission scan. The RCTT device was removed at the end of the 20 minute uptake period and before subjects were transported to the PET center for scanning, so that the device did not interfere with the PET scanning procedures.

The 18F-FDG was obtained commercially. The total number of dosages (i.e., RCTT and control) of 18F-FDG that were given during each PET session (i.e., waking and NREM sleep) was one. Each of the two PET sessions used 5 mCi dose of 18F-FDG for a total of 10 mCi 18F-FDG/subject. Subjects were instructed to void two hours post injection to minimize bladder exposure.

PET scanning focused on the brainstem and forebrain using the wide field of view offered by the ECAT HR+ scanner. A 30 minute emission scan (six summed sequential 5-minute scans to allow for excluding data contaminated by movement) was performed at T=60 minutes. A 10-minute transmission scan was obtained immediately after the emission scan (rather than prior to injection as is typical) to allow quantitative correction of attenuation. Calculation of absolute cerebral metabolic rates followed the guidelines established by Schmidt et al (1996) using a 3K model, and using the single scan, six blood sample method validated by Phillips et al (1995).

All patients underwent MR scanning prior to their first PET study in the UPMC MR Research Center, which is located directly below the PET Facility, using a GE Signa 1.5 Tesla scanner. The subjects were positioned in a standard head coil and a brief scout T1-weighted image obtained. Standard axial T1-weighted (TE=18, TR=400, NEX=1, slice thickness=3 mm/interleaved), images were acquired. MR data was registered with the PET data using AIR software. Registered MR was used as an individualized anatomic map for the selection of ROI's used in the analysis of the PET data.

PET images were reconstructed using standard commercial software as 63 transaxial slices (center-to-center 2.4 mm) with approximately 4-5 mm full-width half-maximum resolution. The image sets from each of the two scanning sessions was co-registered by Automatic Image Registration (AIR) software (Woods et al, 1992). After registration, the PET data is summed and then this very high count image set is registered to the subject's volume MR study by AIR (Woods et al, 1993). Regions-of-interest (ROI) and Statistical Parametric Mapping (SPM) (Friston et al, 1990; Friston et al, 1991) analyses were used.

Data Collection and Statistical Considerations

The research design tested differences in prefrontal glucose metabolism between a control vs. active condition in a within-subjects design. The primary analytic method was a matched t-test using each subject as their own control.

Results

Figure 7:
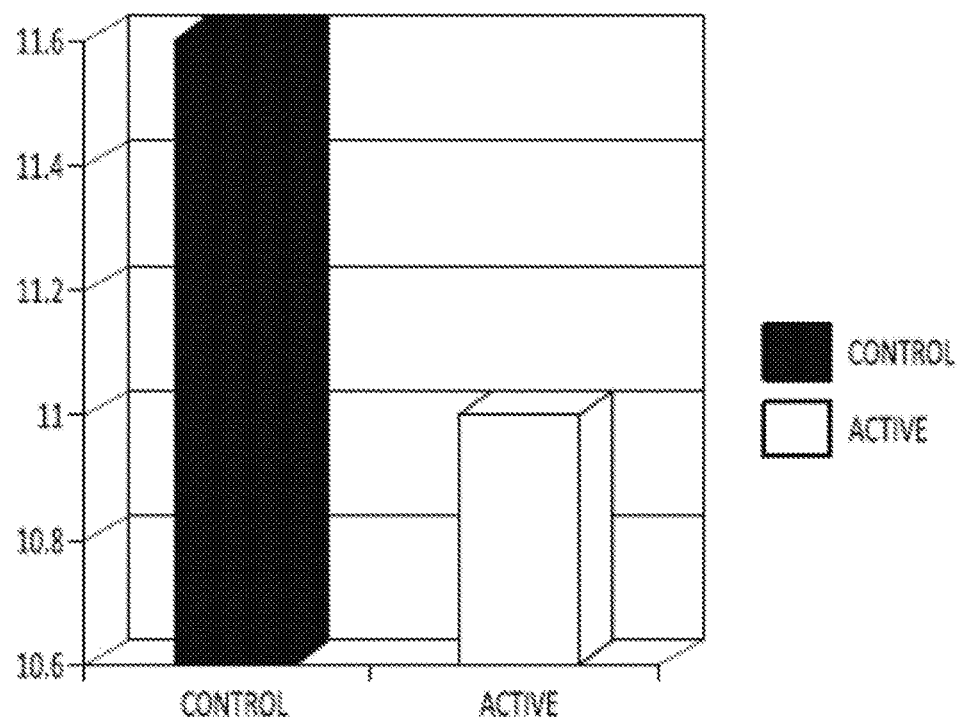
FIG. 7 is a graph illustrating the effects of the device and methods of the present invention on whole brain metabolism.
Figure 8:
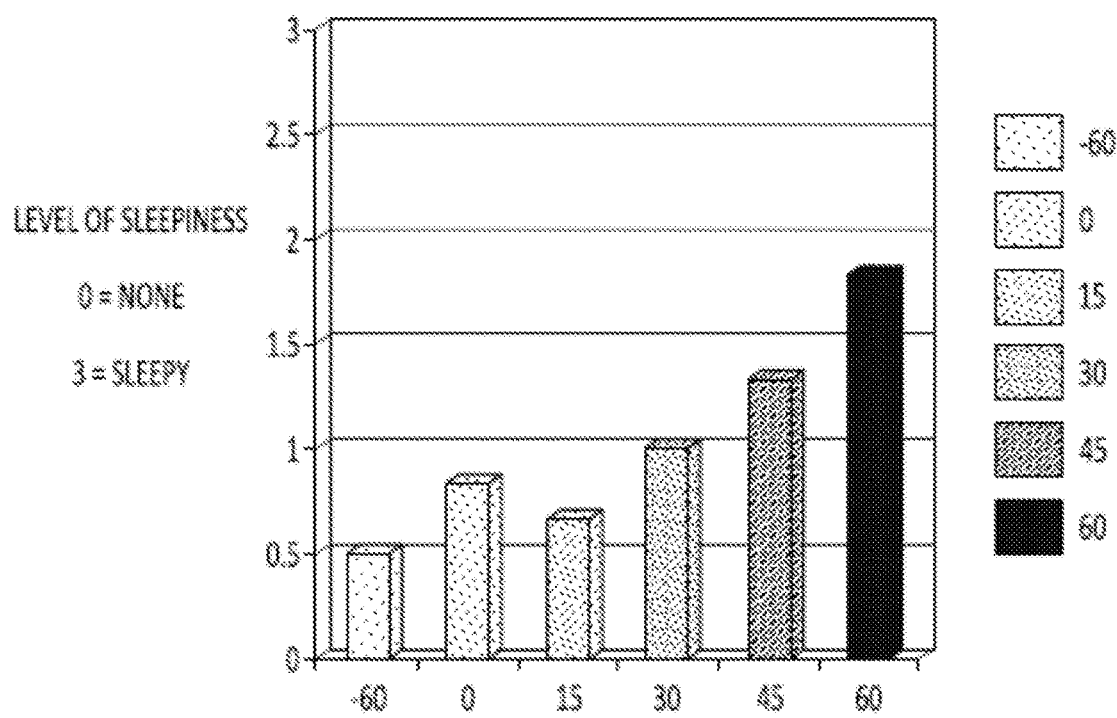
FIG. 8 is a graph illustrating the effects of the device and methods of the present invention on sleepiness in study subjects.
Figure 9:
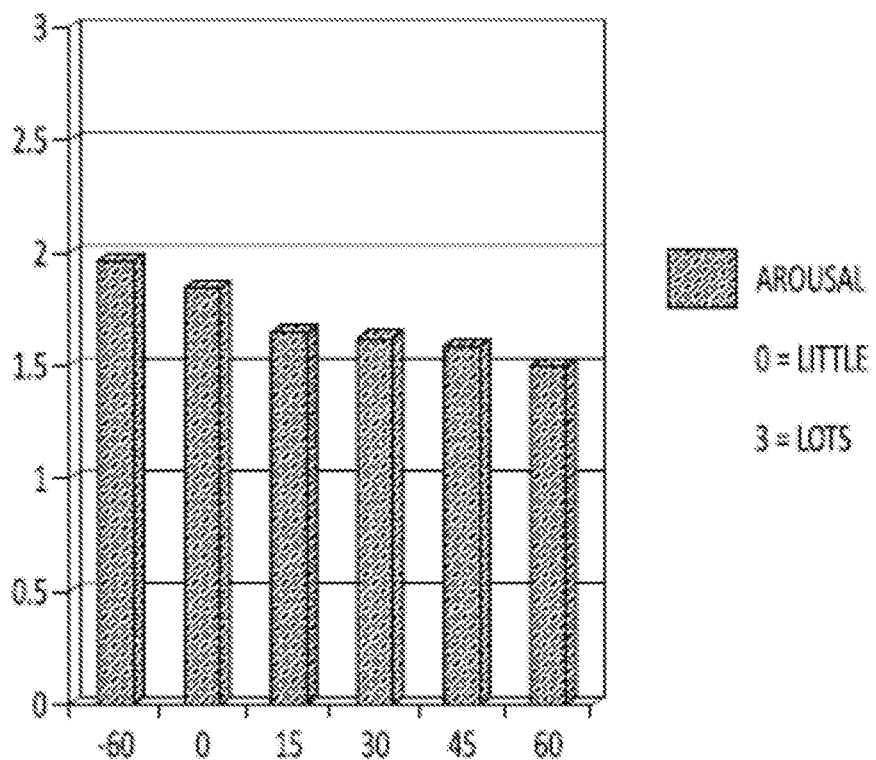
FIG. 9 is a graph illustrating the effects of the device and methods of the present invention on subjective arousal in study subjects.
Figure 10:
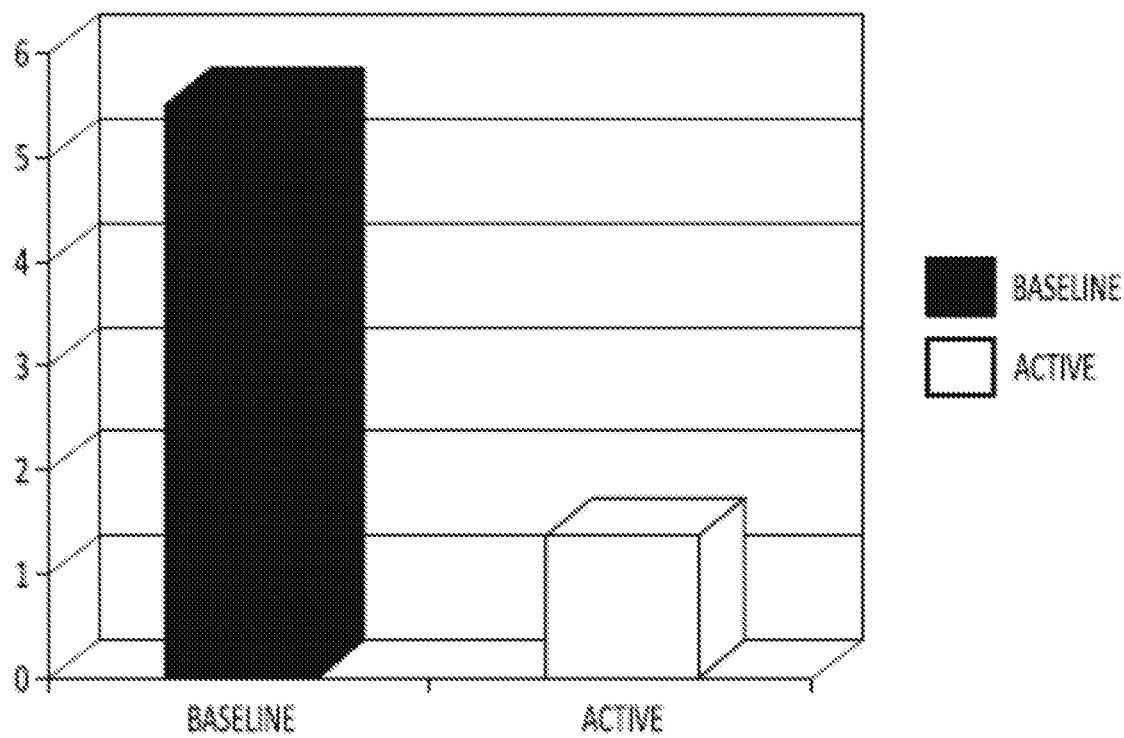
FIG. 10 is a graph illustrating the effects of the device and methods of the present invention on waking after sleep in study subjects.
Figure 11:
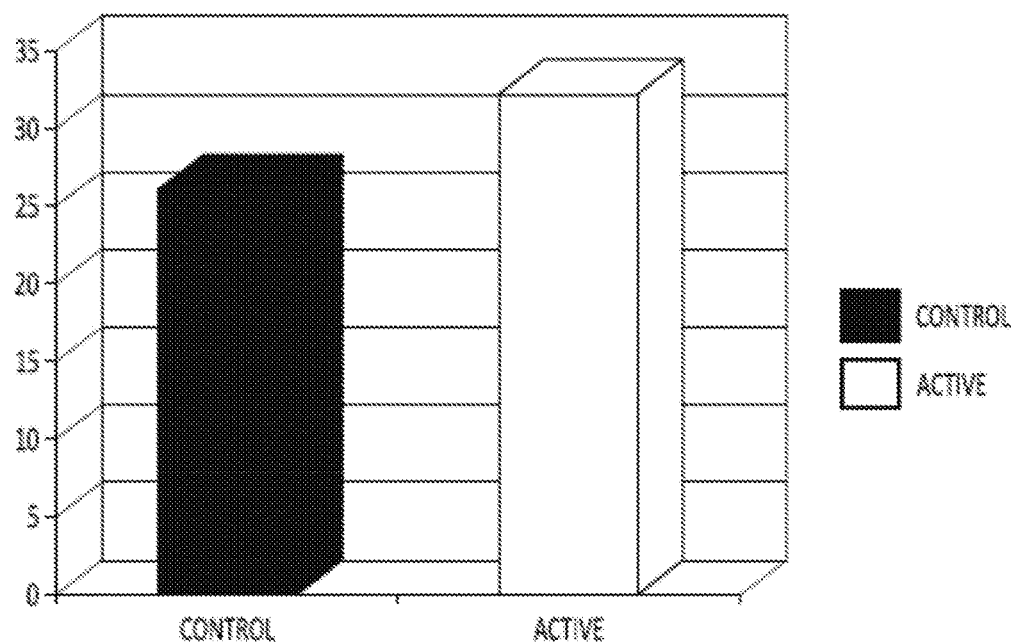
FIG. 11 is a graph illustrating the effects of the device and methods of the present invention on restorative slow wave sleep in study subjects.
Figure 12:
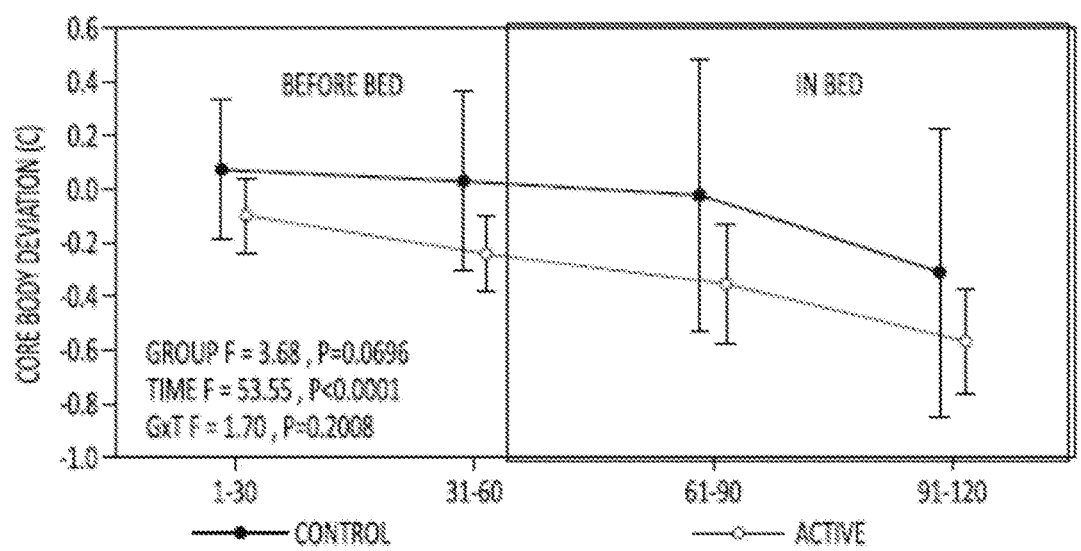
FIG. 12 is a graph illustrating that the device and methods of the present invention accelerate a reduction in core body temperature.

The results of the study are presented in FIGS. 7-12. As shown in FIG. 7, using the device and methods of the present invention, whole brain metabolism was reduced in insomnia patients as compared with the control group. An increase in sleepiness prior to bedtime (FIG. 8), a reduction in arousal (FIG. 9), a reduction in waking after sleep onset (FIG. 10) and an increase in restorative slow wave sleep (FIG. 11) were also found. RCTT also accelerated the reduction in core body temperature associated with sleep onset in insomnia patients (FIG. 12).

Warming

The apparatuses and methods configured may also or alternatively provide a temperature at the patient's forehead that is greater than ambient temperature (e.g., in some variations between about 25° C. and about 42° C.) for a period of time, which may be a predetermined period of time, to treat a neurological disorder.

As used herein the term "warm" or "warming" generally refers to the temperature relative to the ambient temperature surrounding a subject, such as the ambient air temperature (e.g., typically 22° C.) surrounding the subject. A subject wearing an apparatus may perceive a stimulus greater than ambient temperature as "warm", even if the actual temperature of the thermal transfer region of the applicator is lower than the skin surface temperature. Thus, the thermal stimulus applied may be referred to as "warm" or "warming" based on the perception of the thermal transfer region when applied to the subject's forehead, likely because of activation of thermoreceptors in the subject's skin. Thus, in some instances it may be more accurate to refer to warming relative to subject perception (e.g., relative to the ambient temperature). In general, the warm or warming temperature may be between about 25 and 42° C. (e.g., between 25-40° C.).

With respect to sleep, the restorative nature of sleep and studies demonstrating abnormal hyperarousal in insomnia patients described in the medical literature suggests that the restorative aspects of sleep can be linked regionally with heteromodal association cortex, especially in the frontal regions. Two studies were performed to clarify the regional cerebral metabolic correlates of this. In the first study, changes in regional cerebral metabolism that occur between waking and sleep in healthy subjects were identified. Fourteen healthy subjects (age range 21 to 49; 10 women and 4 men) underwent concurrent EEG sleep studies and [18F] fluoro-2-deoxy-D-glucose ([18]-FDG) positron emission tomography (PET) scans during waking and NREM sleep. Whole brain glucose metabolism declined significantly from waking to NREM sleep. Relative decreases in regional metabolism from waking to NREM sleep were found in heteromodal frontal, parietal and temporal cortex, and in dorsomedial and anterior thalamus. These findings are consistent with a restorative role for NREM sleep largely in cortex that subserves essential executive function in waking conscious behavior. In the second study, changes in regional cerebral metabolism were identified that occur between usual NREM sleep and recovery NREM sleep following a night of sleep deprivation. In this study, homeostatic sleep need, or sleep drive, was modulated in a within-subjects design via sleep deprivation. Four young adult healthy male subjects (mean age+s.d.=24.9±1.2 years) received NREM sleep using [18F]fluoro-2-deoxy-D-glucose positron emission tomography ([18F]-FDG PET) assessments after a normal night of sleep and again after 36 hours of sleep deprivation. Both absolute and relative regional cerebral glucose metabolic data were obtained and analyzed. In relation to baseline NREM sleep, subjects' recovery NREM sleep was associated with 1) increased slow wave activity (an electrophysiological marker of sleep drive); 2) global reductions in whole brain metabolism; and 3) relative reductions in glucose metabolism in broad regions of frontal cortex, with some extension into parietal and temporal cortex. The results demonstrate that the homeostatic recovery function of sleep following sleep deprivation is associated with global reductions in whole brain metabolism as well as greater relative reductions in broad regions of largely frontal, and related parietal and temporal cortex. In other words, sleep deprivation accentuates the decrease in brain metabolism normally seen during NREM sleep. A medical device that alters metabolism in a pattern similar to that seen in healthy sleep or recovery sleep following sleep deprivation, therefore, could benefit insomnia patients.

A study of insomnia patients investigated how these normal changes in brain metabolism become disturbed in insomnia patients. Insomnia patients and healthy subjects completed regional cerebral glucose metabolic assessments during both waking and NREM sleep using [18F]fluoro-2-deoxy-D-glucose positron emission tomography (PET). Insomnia patients showed increased global cerebral glucose metabolism during sleep and wakefulness. A group x state interaction analysis confirmed that insomnia subjects showed a smaller decrease than did healthy subjects in relative metabolism from waking to NREM sleep in the ascending reticular activating system, hypothalamus, thalamus, insular cortex, amygdala and hippocampus and in the anterior cingulate and medial prefrontal cortices. While awake, in relation to healthy subjects, insomnia subjects showed relative hypometabolism in a broad region of the frontal cortex bilaterally, left hemispheric superior temporal, parietal and occipital cortices, the thalamus, hypothalamus and brainstem reticular formation. This study demonstrated that subjectively disturbed sleep in insomnia patients is associated with increased brain metabolism. Their inability to fall asleep may be related to a failure of arousal mechanisms to decline in activity from waking to sleep. Further, their daytime fatigue may reflect decreased activity in prefrontal cortex that results from inefficient sleep. These findings suggest interacting neural networks in the neurobiology of insomnia. These include a general arousal system (ascending reticular formation and hypothalamus), an emotion regulating system (hippocampus, amygdala and anterior cingulate cortex), and a cognitive system (prefrontal cortex). Notably, ascending arousal networks are functionally connected to cortical regions involved in cognitive arousal at the cortical level which can feedback and modulate more primitive brainstem and hypothalamic arousal centers. A medical device that alters metabolism in one or more portions of this network could benefit insomnia patients and produce more restful sleep.

A second study in insomnia patients was conducted to clarify the cerebral metabolic correlates of wakefulness after sleep onset (WASO) in primary insomnia patients testing the hypothesis that insomnia subjects with more WASO would demonstrate increased relative metabolism especially in the prefrontal cortex given the role of this region of the brain in restorative sleep and in cognitive arousal. Fifteen patients who met DSM-IV criteria for primary insomnia completed 1-week sleep diary (subjective) and polysomnographic (objective) assessments of WASO and regional cerebral glucose metabolic assessments during NREM sleep using [18F] fluoro-2-deoxy-D-glucose positron emission tomography (PET). Both subjective and objective WASO positively correlated with NREM sleep-related cerebral glucose metabolism in the pontine tegmentum and in thalamocortical networks in a frontal, anterior temporal, and anterior cingulate distribution. These effects may result from increased activity in arousal systems during sleep and/or to activity in higher order cognitive processes related to goal-directed behavior, conflict monitoring, emotional awareness, anxiety and fear. These processes are thought to be regulated by activity of the prefrontal cortex.

Although many of the studies and examples described above are related specifically to sleep, the methods and apparatuses described herein may similarly be used to treat other neurological/neuropsychiatric disorders, as described above.

For example, forehead warming may provide an indirect path towards activating warm sensitive neurons in the hypothalamus. In general, any of the apparatuses for enhancing sleep by warming forehead temperature (relative to ambient temperature) described herein may include an applicator (e.g., pad, etc.) that fits against a subject's forehead and can be worn before and/or during sleep. In some variations, an apparatus for enhancing sleep by warming the forehead relative to the ambient temperature may include a custom-sized headpiece to fit the area of the scalp over the frontal cortex that circulated varying temperature fluids and a programmable warming chamber/pump that provided the warming and power for circulating the fluid to the headpiece.

In one example of an apparatus for enhancing sleep by increasing forehead temperature relative to the ambient temperature, the apparatus includes a thermal regulator unit, a thermal applicator/hose assembly (sometimes referred to as the forehead pad) and a headgear to maintain the thermal applicator in contact and in position with the frontal cortex. As mentioned above, the apparatus described herein may be worn by a sleeping subject, and thus may be adapted for comfort as well as safety and efficacy. In variations including a fluid (including a circulating fluid), the apparatus may be configured to prevent fluid loss/leakage. An apparatus for enhancing sleep by increasing forehead temperature relative to the ambient temperature may also be used without a circulating fluid. For example, by directly heating (including resistive heating) of the skin-contacting surface of the applicator. An apparatus for enhancing sleep by decreasing (or increasing) forehead temperature relative to the ambient temperature may also be used without a circulating fluid. For example, by directly cooling (including thermoelectric cooler, convection coolers such as fans, etc.) of the skin-contacting surface of the applicator.

For example, a thermal regulator unit may utilizes thermal electric modules (TECs), to heat (or cool) the applicator directly, or to heat a thermal transfer fluid (TTF) which is pumped through transfer lines of the thermal applicator. Other heaters such as resistive heating coils, chemical heating (e.g., exothermic reactions), high specific-heat capacity materials, or phase-change materials could also be used as part of the thermal regulator unit; other coolers (including chemical coolers) may be used.

In one variation, the apparatus is configured to operate with a TFF (fluid) to heat the applicator. Major components of such a thermal regulator unit may include a one or more heat exchangers, heat sinks, TECs, a pump, fan, electronic control circuits, software, user interface, TTF reservoir, unit enclosure, connections for incoming electrical power, and TTF connections for the thermal applicator.

In some variations, the components may be assembled such that the heat sink(s) are placed in thermal contact with one side of the TEC(s) and the heat exchanger is placed in thermal contact with the opposite side of the TEC(s) away from the heat sink. The heat exchanger can be constructed from any known material and design for the purpose. Portions of the assembly can be insulated to reduce parasitic heat loads on the heat exchanger. The thermal regulator unit can be operated in a warming (or cooling) mode to control the temperature of the TTF to the desired levels. The thermal regulator utilizes a pump to circulate the TTF through the heat exchanger and the thermal applicator. The pump can be of any appropriate type, i.e. centrifugal, piston, gear, diaphragm etc. A TTF reservoir is incorporated to provide additional TTF to replenish the TTF lost for any reason. The reservoir can be an integral fillable component within the thermal regulator unit or can be constructed as a replaceable cartridge. The plumbing connection for the reservoir may be designed such that the volume of the TTF within the reservoir is not serially located within the TTF circulation circuit of the heat exchanger and the thermal applicator. This design is referred to as a side stream reservoir.

The side stream configuration effectively allows the thermal regulator to heat/cool the circulating TTF to the desired temperature faster by eliminating the need to heat/cool the TTF held in the reservoir. The reservoir or replaceable cartridge can be sized as required to provide the desired capacity for the user's convenience. The replaceable cartridge can be configured with a valve system that allows the user to engage or remove the cartridge into the thermal regulator without causing a leak of TTF. The cartridge may be configured with a one way vent to allow air intake as the TTF is drained from the cartridge. This configuration allows the TTF to drain from the cartridge and not re-enter the cartridge if a back pressure is generated within the circulating circuit. If this type of one way vent is utilized in the cartridge, a separate air vent may be plumbed into the circulation circuit to allow air trapped within the circuit to exit. Another configuration of the cartridge utilizes two connection points into the thermal regulator. One connection allows air trapped within the circulation circuit to vent into the cartridge while TTF is allowed to drain into the circulation circuit from the second connection point. The connection valves may be designed in any number of known configurations. One such implementation utilizes check valves in each of the mating connection components. This may provide a means of engaging or removing the cartridge without TTF leaking from the removed cartridge or from the mating connection point within the thermal regulator. In another variation the cartridge is sealed with a rubber type material that can be punctured with a hollow needle. Once punctured the TTF would make a fluid connection with the circulation circuit. When the cartridge is removed, the needle would be withdrawn allowing the rubber type material to reseal the puncture hole preventing the TTF from leaking from the cartridge. The needle would be designed with a spring loaded sliding rubber type material seal that would slide over the inlet port on of the needle when the cartridge is removed. Another variation utilizes ball type or O-ring seal type check valves commonly known. The cartridge size and shape are determined by the required capacity, the desired cosmetic industrial design and the available space within the enclosure. Once engaged in the thermal regulator, the cartridge is held in place by any latching mechanism. In another embodiment, the cartridge air vent is bi-directional and may be constructed of a material such as Gore-Tex. Such a material allows air to pass through it while preventing TTF from passing.

In some variations the cartridge may include a liner holding the fluid within the cartridge, and the liner may be collapsible as fluid is removed and expandable as fluid is added to the cartridge. In variations including a collapsible liner (bag or holder), the cartridge may not need or include a vent into the fluid, and the fluid reservoir held by the liner may be isolated from the environment, reducing the likelihood of leakage.

The cartridge and engagement valves are designed to prevent or minimize the potential of the user refilling the cartridge. This design will ensure the user only utilizes TTF specifically formulated for the cooling unit.

The TTF can consist of but is not limited to distilled water, an anti-microbial agent, a component to lower the freezing point and a wetting agent. Other TTF ingredients could also be used. All TTF may be compliant with the bio compatibility requirements of IEC 60601 and FDA requirements.

The control circuits may or may not utilize software for controlling the cooling or heating of the thermal regulator unit. The control circuit may utilizes one or more thermistors located within or in proximity to the circulating circuit to measure the temperature of the TTF and adjust the power to the TECs as required to maintain the TTF within the circulating circuit at the desired temperature. Additionally, the control circuit can utilize one or more thermal control switches located on the heat sink and possibly the heat exchanger as a safety switch in case temperatures on one or both components are outside the desired thresholds. The control circuit may utilize Pulse width modulation (PWM) to provide power to the TECs, pump and fan. Software can also be utilized to provide control algorithms for controlling all aspects of the system. The software could control the power to be supplied to the TECs in such way to produce any desired cooling curve of the TTF. In one variation the power could be applied to the TECs such that the TTF is cooled more rapidly with the onset of power and the rate of temperature change is reduced as the actual TTF temperature and targeted TTF temperature difference becomes smaller. There are other temperature curves that could be considered. Additionally, the TTF temperature could be controlled by user physiological measurements or by time. The control circuits can also provide a user interface to the cooling unit. Possible variations could include but not be limited to an on/off switch, heat/cool mode selector switch, temperature display of targeted temperature or actual temperature of the TTF. The control circuit could also control display lighting. In some variations the control circuit can monitor the level of TTF in the reservoir or cartridge and display the level to the user. The control circuit could also shut the unit off if it detected a low or empty TTF level.

The enclosure provides a means of mounting all of the internal components of the system and provides for air intake and exhaust of the fan air. The fan inlet and exhaust can be directed through a grid system within the enclosure that is designed to prevent users from coming in contact with components that could produce an injury. Furthermore, the grids may be designed in such a way to allow the user to direct the airflow in a direction they find desirable. The enclosure allows for a conveniently positioned user interface, reservoir filling or cartridge replacement, a visual means for determining the TTF level remaining, connection points for incoming power, connection points for the inlet and outlet of the circulating circuit thermal applicator/hose assembly and any other desirable connections.

The inlet/outlet connectors of the thermal applicator/hose assembly and the thermal regulator enclosure connectors utilize check valves that allow the thermal applicator/hose assembly to be connected and removed from the regulator assembly without leaking TTF from either component. The hose portion of the assembly is sufficiently insulated to prevent or minimize condensation on the hose assembly to the desired ambient temperature and humidity conditions. The thermal applicator component of the system may be designed to form a seal between at least two layers of flexible rubber like material. The seal may be formed by any known technique such at ultra-sonic welding, RF welding, adhesive bonding or chemical welding. The flexible material layers are selected from a wide range of known materials that exhibit the desired material properties such as flexibility, conformability, permeability, comfortable feel for the user etc. such as urethane or vinyl sheet. It is desirable the material is bio-compatible. The seal formed between the layers forms a flow channel or passageway for the TTF to circulate while the applicator is in contact with the user's skin. The thermal applicator acts as a heat exchanger when used in this way. The TTF which is temperature controlled by the thermal regulator is pumped through the hose portion of the assembly into the thermal applicator in contact with the user's skin. Thermal energy is transferred to or from the user depending upon the selected temperature of the TTF and the user's skin temperature. The design of the channels and the total length of channels produced by forming the seal between the layers of the applicator effect the amount of energy transferred. The design of the channels and the circulation path within the applicator also effect the temperature variation within the applicator. It is desirable to design the channels in such a way to maintain an even distribution of temperature across the applicator. The inlet and outlet connections of the hose to the thermal applicator may be made permanent or utilize the type of connections that can be disconnected. The design of the channels within the applicator may vary in size or cross sectional area to produce desired pressures, temperatures or flows within the channels. Additionally, the use of small weld spots or dots within the flow channels may be used to control ballooning of the channel while under pressure. The outer perimeter of the applicator is designed to provide contouring of the applicator to the desired portion of the user's skull in proximity to the fontal/prefrontal cortex. This area is generally defined as the area including the left and right temple area and the area defined between the eyebrows and the top center of the head. The applicator perimeter may also include a variety of cuts, slits or other geometrical definitions that allow the applicator to better contour to the user's head within the desired contact area.

The thermal applicator may be held in contact with the subjects head with a head gear system. In one variation of the headgear component, a series of adjustable straps are used to selectively adjust the contact pressure of the applicator to the user. Other variations of the headgear can be constructed with and elastic type material without adjustability. The elastic nature of the material applies contact pressure to the thermal applicator. Other variations utilize both features, i.e. adjustable straps and elastic materials. In some variations the thermal applicator can be permanently integrated with the headgear and in other variations, the thermal applicator can be removable from the headgear.

As mentioned, the applicator portion of the apparatus generally includes as skin-contacting region configured to lie against the subject's forehead. The skin-contacting region generally includes the thermal transfer region. Temperature is only regulated actively over the thermal transfer region, which is preferably the region of the subject's forehead. The applicator may be configured so that other regions of the subject's head or face are not in contact with the thermal transfer region; thus temperature regulation may only be applied to the forehead but not to other regions such as the eye orbits, cheeks, neck, back of the head, hairline, etc. Thus, in some variations the applicator may contact or cover other regions, not just the forehead, but the thermal transfer regions may only contact the forehead but not the eye (periorbital and orbital regions) or cheek regions.

The applicator may generally be configured to enhance wearer comfort. For example, the applicator may have a relatively thin thickness (e.g., less than 5 cm, less than 2 cm, less than 1 cm, etc.), so that it can be comfortably worn while sleeping. The applicator may adjustably fit to a variety of patient head circumferences.

In general any of the apparatuses described herein may be configured to apply a temperature that is greater than the ambient temperature surrounding the subject. In some variations this means controlling the patient-contacting (skin-contacting) surface of the applicator to a temperature that is between 25° C. and 40° C. (e.g., 27° C., 28° C., 29° C., 30° C., 31° C., 32° C., 33° C., 34° C., 35° C., 36° C., 37° C., 38° C., 39° C., 40° C., or any intermediate temperature there between). The temperature may be held constant or varied (or allowed to vary) within a range (e.g., between about 27° C. and 40° C., etc.).

In some variations the temperature applied may be determined based on the relative ambient temperature. For example, the temperature applied may set to a predetermined amount ($\Delta_{Temp}$) warmer than the ambient temperature (e.g., 0.5° C. warmer than ambient, 1° C. warmer than ambient, 1.5° C. warmer than ambient, 2° C. warmer than ambient, etc.). In some variations, the maximum temperature may be limited to 40° C.

Thus, in some variations, the regional application of the thermal transfer pad (applicator) may be used to treat a neurological disorder. The treatment region may be limited to the forehead, as mentioned above. For example, in one variation, the thermal transfer pad is shaped to cover the region of the forehead that overlies glabrous (non-hairy) skin. The frontal cortex is thought to be uniquely important among body regions for providing thermoregulatory information to the hypothalamus given that it has the highest thermal sensitivity of body surfaces, it has a neural and vascular supply that are specialized for this function and the forehead allows a convenient surface for placing a pad during sleep applications as to minimally interfere with sleep. Thus, an arrangement of the applicator that established thermal transfer between the applicator and the forehead may benefit sleep.

Some disorders, such as depression, have characteristic alterations in REM sleep. The study discussed above demonstrates that altering the temperature of the thermal transfer applicator has predictable effects on the occurrence of REM sleep. One method of treatment may include a variable thermal transfer across the night that is intended to target the occurrence of REM sleep in a therapeutic manner. In depression, for example, where REM sleep duration and intensity seem to be more highly concentrated in the first third of the night, use of 30° C. by the applicator over this period would be expected to inhibit abnormal REM sleep production whereas the use of more neutral temperatures (e.g., ambient) in the latter half of the night may lead to more normal REM sleep production in that part of the night.

Alterations in REM and NREM sleep can occur in a variety of neuropsychiatric disorders. The general principle of altering the temperature of the thermal transfer region of the applicator (which may be referred to herein as a "mask") to facilitate or diminish discrete aspects of deep NREM sleep or REM sleep that are directly related to the specific disorder would be expected to have therapeutic utility specific to the disorder.

In any of the variations described herein, the apparatus may include one or more temperature sensors to detect ambient temperature and/or skin temperature. For example, the apparatus may detect ambient temperature at or near the applicator and/or may detect skin temperature of a subject wearing the applicator. Sensed temperature information may be feed back into the apparatus controller, and may be used, for example, to set or adjust the temperature applied.

The apparatuses described herein may also include or to operate with one or more sensors (or sensing subsystems) configured to determine a subject's sleep state. Sensors or sensing subsystems may include EEG (electroencephalogram) sensors, motion sensors (detecting sleep motions to determine sleep state), and/or body temperature sensors, or other means for determining sleep as known to those of skill in the art; additional examples are provided below.

Altering the temperature properties of the applicator have been shown to have predictable effects on sleep physiology. It would be possible, therefore, to measure the changes in sleep physiology and incorporate them into a feedback loop that then results in changes in the temperature. In this manner, the apparatus controller may therefore adjust the apparatus temperature applied in real time to achieve some desired physiological effect.

In some variations, a variable temperature with defined changes can be delivered across the period of use with the changes linked to feedback from changes in the physiology of the body across a period of use.

For example, the following physiological measures may be monitored and temperature adjusted in real time according to the level of the physiological measure: presence or absence of REM or NREM sleep as assessed by any method of REM/NREM sleep assessment by someone skilled in the art, such as EEG frequency, Heart Rate Variability, Muscle Tone or other means; depth of slow wave sleep, as measured by EEG wave analysis or other means; degree of autonomic arousal as measured by HR variability or other means; galvanic skin response; skin temperature, either at the skin on the head underneath the device, or on skin at some other portion of the head not underneath the device, or peripheral skin temperature, or core body temperature (measured internally or by some external means) or some combined measure assessing thermoregulation of the head and periphery, or core body to peripheral temperature measure.

As mentioned, the person wearing the device may, in some variations, modify the temperature profile across the period of use, with or without the changes linked to feedback. For example, a control on the apparatus may allow the subject wearing the apparatus to adjust the temperature according to their immediate comfort and treatment needs, either up or down some small increments.

The applicator may generally include skin-contacting (forehead contacting) thermal transfer region. This thermal transfer region may be configured of any appropriate material. For example, in some variations, the lining of the transfer pad that comes in contact with the skin is a hydrogel allowing for increased surface area contact and increased thermal transfer characteristics. Other materials with appropriate temperature transfer characteristics could be used.

In some variations the applicator includes a lining is combined with dermatologic products that can be rejuvenating for the skin when in contact over the course of a night. For example, creams configured to hydrate the skin and/or apply a medicament to the skin may be used.

In some variations an inner lining can be refreshed on a nightly or less frequent basis that can benefit the skin when applied over the night of sleep. Thus, an applicator, and particularly the skin-contacting portion of the applicator may be configured to be disposable and/or replaceable either daily (e.g., nightly), every other day, every week, etc.

Any of the variations of the apparatuses described herein may also be configured to record, store and/or transmit data about the operation of the device and/or the subject using the device. In the clinical management of a patient, a healthcare provider may want to know certain parameters of the patient and/or device over multiple nights of use such that care can be optimized. In some variations, a memory (e.g. memory card, memory chip, etc.), automatically records all or some parameters and stores them for later display and/or transmission to a healthcare provider. Further, in monitoring their own care, a device user may want to know certain parameters of the patient and/or device over multiple nights of use such that care can be optimized. The apparatus may be configured to display and/or transmit this information, e.g., for uploading to a computing device (computer, mobile communications device, website, etc.).

In some variations, this information could be transferred to a healthcare provider's office or some other central database via the phone or internet or some wireless technology where someone could review the information and provide recommended adjustments in the treatment accordingly.

Examples of information that may be stored could include, but would not be limited to: temperature of the applicator; skin temperature; core body temperature; measures of autonomic variability, depth of sleep as assessed by NREM sleep, EEG power in discrete frequency bands; REM sleep or other sleep staging, etc.; periods of activity and/or wakefulness across the night; subjective measures of sleep depth/comfort/satisfaction; and sleep duration.

The apparatuses described herein can be used for treating neurological disorders and neuropsychiatric disorders by applying the apparatuses to heat and/or cool the forehead region of a subject. In some embodiments, the disclosure provides a method for treating a neurological disorder in a subject. The method includes securing a thermal transfer region of an applicator in contact with the forehead of the subject in need thereof so that the thermal transfer region does not contact the perioribtal region of the subject's face; and maintaining the temperature of the thermal transfer region within a target temperature range that is between 10 and 28° C. for a predetermined amount of time.

Exemplary neurological disorders and diseases treatable with the apparatus and methods described herein include, but are not limited to, Abulia, Agraphia, Alcoholism, Alien hand syndrome, Allan-Herndon-Dudley syndrome, Alternating hemiplegia of childhood, Alzheimer's disease, Amaurosis fugax, Amnesia, Amyotrophic lateral sclerosis (ALS), Aneurysm, Angelman syndrome, Anosognosia, anxiety, Aphasia, Apraxia, Arachnoiditis, Arnold-Chiari malformation, Asomatognosia, Asperger syndrome, Ataxia, Attention deficit hyperactivity disorder (ADHD), ATR-16 syndrome, Auditory processing disorder, Autism spectrum, Behçet's disease, Bipolar disorder, Bell's palsy, Brachial plexus injury, Brain injury, Brain tumor, Brody myopathy, Canavan disease, Capgras delusion, Carpal tunnel syndrome, Causalgia, Central pain syndrome, Central pontine myelinolysis, Centronuclear myopathy, Cephalic disorder, Cerebral aneurysm, Cerebral arteriosclerosis, Cerebral atrophy, Cerebral autosomal dominant arteriopathy with subcortical infarcts and leukoencephalopathy, Cerebral dysgenesis-neuropathy-ichthyosis-keratoderma syndrome, Cerebral gigantism, Cerebral palsy, Cerebral vasculitis, Cervical spinal stenosis, Charcot-Marie-Tooth disease, Chiari malformation, Chorea, Chronic fatigue syndrome, Chronic inflammatory demyelinating polyneuropathy, Chronic pain, Cluster Headache, Cockayne syndrome, Coffin-Lowry syndrome, Coma, Complex regional pain syndrome, Compression neuropathy, Congenital distal spinal muscular atrophy, Congenital facial diplegia, Corticobasal degeneration, Cranial arteritis, Craniosynostosis, Creutzfeldt-Jakob disease, Cumulative trauma disorders, Cushing's syndrome, Cyclothymic; disorder, Cyclic vomiting syndrome, Cytomegalic inclusion body disease, Cytomegalovirus Infection, Dandy-Walker syndrome, Dawson disease, De Morsier's syndrome, Dejerine-Klumpke palsy, Dejerine-Sottas disease, Delayed sleep phase disorder or syndrome, Dementia, Depression, Dermatomyositis, Developmental coordination disorder, Diabetic neuropathy, Diffuse sclerosis, Diplopia, Disorders of consciousness, Distal hereditary motor neuropathy type V, Distal spinal muscular atrophy type 1, Distal spinal muscular atrophy type 2, Down syndrome, Dravet syndrome, Duchenne muscular dystrophy, Dysarthria, Dysautonomia, Dyscalculia, Dysgraphia, Dyskinesia, Dyslexia, Dystonia, Empty sella syndrome, Encephalitis, Encephalocele, Encephalotrigeminal angiomatosis, Encopresis, Enuresis, Epilepsy, Epilepsy-intellectual disability in females, Erb's palsy, Erythromelalgia, Essential tremor, Exploding head syndrome, Fabry's disease, Fahr's syndrome, Fainting, Familial spastic paralysis, Febrile seizures, Fisher syndrome, Friedreich's ataxia, Fibromyalgia, Foville's syndrome, Fetal alcohol syndrome, Fragile λ syndrome, Fragile X-associated tremor/ataxia syndrome, Functional Neurological Disorder, Gaucher's disease, Generalized epilepsy with febrile seizures plus, Gerstmann's syndrome, Giant cell arteritis, Giant cell inclusion disease, Globoid cell leukodystrophy, Gray matter heterotopia, Guillain-Barré syndrome, Generalized anxiety disorder, HTLV-1 associated myelopathy, Hallervorden-Spatz syndrome, Head injury, Headache, Hemicrania Continua, Hemifacial spasm, Hereditary motor neuropathies, Hereditary motor neuropathies, Hereditary spastic paraplegia, Heredopathia atactica polyneuritiformis, Herpes zoster oticus, Herpes zoster, Hirayama syndrome, Hirschsprung's disease, Holmes-Adie syndrome, Holoprosencephaly, Huntington's disease, Hydranencephaly, Hydrocephalus, Hypercortisolism, Hypoxia, Immune-mediated encephalomyelitis, Inclusion body myositis, Incontinentia pigmenti, Refsum disease, infantile spasms, inflammatory myopathy, Intracranial cyst, Intracranial hypertension, isodicentric 15, Joubert syndrome, Karak syndrome, Kearns-Sayre syndrome, Kinsbourne syndrome, Kleine-Levin syndrome, Klippel Feil syndrome, Krabbe disease, Kufor-Rakeb syndrome, Kugelberg-Welander disease, Lafora disease, Lambert-Eaton myasthenic syndrome, Landau-Kleffner syndrome, Lateral medullary (Wallenberg) syndrome, Learning disabilities, Leigh's disease, Lennox-Gastaut syndrome, Lesch-Nyhan syndrome, Leukodystrophy, Leukoencephalopathy with vanishing white matter, Lewy body dementia, Lissencephaly, Locked-in syndrome, Lou Gehrig's disease, Lumbar disc disease, Lumbar spinal stenosis, Lupus erythematosus-neurological sequelae, Lyme disease, Machado-Joseph disease, Macrencephaly, Macropsia, Mal de debarquement, Megalencephalic leukoencephalopathy with subcortical cysts, Megalencephaly, Melkersson-Rosenthal syndrome, Menieres disease, Meningitis, Menkes disease, Metachromatic leukodystrophy, Microcephaly, Micropsia, Migraine, Miller Fisher syndrome, Mini-stroke, Misophonia, Mitochondrial myopathy, syndrome, Monomelic amyotrophy, Morvan syndrome, Motor neurone disease, Motor skills disorder, Moyamoya disease, Mucopolysaccharidoses, Multi-infarct dementia, Multifocal motor neuropathy, Multiple sclerosis, Multiple system atrophy, Muscular dystrophy, Myalgic encephalomyelitis, Myasthenia gravis, Myelinoclastic diffuse sclerosis, Myoclonic Encephalopathy of infants, Myoclonus, Myopathy, Myotubular myopathy, Myotonia congenital, Narcolepsy, Neuro-Behçet's disease, Neurofibromatosis, Neuroleptic malignant syndrome, Neuromyotonia, Neuronal ceroid lipofuscinosis, Neuronal migration disorders, Neuropathy, Neurosis, Niemann-Pick disease, Non-24-hour sleep-wake disorder, Nonverbal learning disorder, O'Sullivan-McLeod syndrome, Occipital Neuralgia, Occult spinal dysraphism sequence, Ohtahara syndrome, Olivopontocerebellar atrophy, Opsoclonus myoclonus syndrome, Optic neuritis, Orthostatic hypotension, Otosclerosis, Overuse syndrome, Palinopsia, Paresthesia, Parkinson's disease, Paramyotonia congenital, Paraneoplastic diseases, Paroxysmal attacks, Parry-Romberg syndrome, PANDAS, Pelizaeus-Merzbacher disease, Periodic paralyses, Peripheral neuropathy, Pervasive developmental disorders, Phantom limb/Phantom pain, Photic sneeze reflex, Phytanic acid storage disease, Pick's disease, Pinched nerve, Pituitary tumors, PMG, Polyneuropathy, Polio, Polymicrogyria, Polymyositis, Porencephaly, Post-polio syndrome, Postherpetic neuralgia, Postural hypotension, Prader-Willi syndrome, Primary lateral sclerosis, Prion diseases, Progressive hemifacial atrophy, Progressive multifocal leukoencephalopathy, Progressive supranuclear palsy, Prosopagnosia, Pseudotumor cerebri, Quadrantanopia, Quadriplegia, Rabies, Radiculopathy, Ramsay Hunt syndrome type I, Ramsay Hunt syndrome type II, Ramsay Hunt syndrome type III, Rasmussen encephalitis, Reflex neurovascular dystrophy, Refsum disease, REM sleep behavior disorder, Repetitive stress injury, Restless legs syndrome, Retrovirus-associated myelopathy, Rett syndrome, Reye's syndrome, Rhythmic movement disorder, Romberg syndrome, Saint Vitus dance, Sandhoff disease, Schilder's disease, Schizencephaly, seizure, Sensory processing disorder, Septo-optic dysplasia, Shaken baby syndrome, Shingles, Shy-Drager syndrome, Sjögren's syndrome, Sleep apnea, Sleeping sickness, Snatiation, Sotos syndrome, Spasticity, Spina bifida, Spinal and bulbar muscular atrophy, Spinal cord injury, Spinal cord tumors, Spinal muscular atrophy, Spinal muscular atrophy with respiratory distress type 1, Spinocerebellar ataxia, Split-brain, Steele-Richardson-Olszewski syndrome, Stiff-person syndrome, Stroke, Sturge-Weber syndrome, Stuttering, Subacute sclerosing panencephalitis, Subcortical arteriosclerotic encephalopathy, Superficial siderosis, Sydenham's chorea, Syncope, Synesthesia, Syringomyelia, Tarsal tunnel syndrome, Tardive dyskinesia, Tardive dysphrenia, Tarlov cyst, Tay-Sachs disease, Temporal arteritis, Temporal lobe epilepsy, Tetanus, Tethered spinal cord syndrome, Thalamocortical dysrhythmia, Thomsen disease, Thoracic outlet syndrome, Tic Douloureux, Todd's paralysis, Tourette syndrome, Toxic encephalopathy, Transient ischemic attack, Transmissible spongiform encephalopathies, Transverse myelitis, Traumatic brain injury, Tremor, Trichotillomania, Trigeminal neuralgia, Tropical spastic paraparesis, Trypanosomiasis, Tuberous sclerosis, Tinnitus, Unverricht-Lundborg disease, Vestibular schwannoma, Von Hippel-Lindau disease, Vil-iuisk encephalomyelitis, Visual Snow, Wallenberg's syndrome, Werdnig-Hoffmann disease. West syndrome, Whiplash, Williams syndrome, Wilson's disease, Y-Linked hearing impairment, and Zellweger syndrome.

In some embodiments, the neurological disorders treatable with the methods and apparatus include depression, anxiety, posttraumatic stress disorder (PTSD) and attention-deficit/hyperactivity disorder (ADHD).

In some embodiments, the neurological disorders treatable with the methods and apparatus include Stroke, Multiple Sclerosis, Parkinson's Disease, Traumatic Brain Injury, Spinal Cord Injury, Dystonia, Chronic Regional Pain Syndrome, Motor Neuron Disease/Amyotrophic Lateral Sclerosis, Guillain-Barre Syndrome, Muscular Dystrophy, Cerebral Palsy, Neuropathy, Progressive Supranuclear Palsy (PSP), Multi System Atrophy (MSA), Bells Palsy, Spinal Cerebellar Ataxia (SCA), Hereditary Spastic Paraparesis and Myositis.

In some embodiments, the neurological disorders and conditions treatable with the methods and apparatus include epilesy, non-epileptic seizures, migraine, syncope, multiple sclerosis, neuropathy and neuralgia.

In some embodiments, the neuropsychiatric disorders and conditions treatable with the methods and apparatus include anxiety, neurotic com-plaints, apathy, mood disorder, hallucination, delusion, behavioral change, personality alteration, and delirium.\

In some embodiments, the neuropsychiatric disorders and conditions treatable with the methods and apparatus include depression, mood disorders, anxiety disorders, substance abuse, post-traumatic stress disorder, psychotic disorders, manic-depressive illness and personality disorders.

In some embodiments, the neuropsychiatric disorders and conditions treatable with the methods and apparatus include Alzheimer's disease, frontotemporal lobar degeneration, progressive supranuclear palsy, corticobasal degeneration, Huntington's disease, and Lewy body disease), Creutzfeldt-Jakob disease, cerebrovascular disorders, subdural hematoma, encephalitis, traumatic brain injury, brain tumor, metabolic encephalopathy, intoxication, and normal pressure hydrocephalus.

In some embodiments, the neuropsychiatric disorders and conditions treatable with the methods and apparatus include anxiety disorders, mood disorders, depression, bipolar disorders, substance abuse and impulse control disorders, eating disorders, learning disabilities, anorexia, suspected personality disorders, dementia, and gender dysphoria.

In some embodiments, the neurological disorders and neuropsychiatric disorders and conditions treatable with the methods and apparatus include depression, anxiety, post-traumatic stress disorder (PTSD) and attention-deficit disorder (ADHD), and obsessive compulsive disorder (OCD).

In some embodiments, the disclosure provides methods of treating neurological disorders and neuropsychiatric disorders and conditions. The method includes warming and/or cooling the thermal transfer region, for example, cooling from 10° C. to 28° C. for a predetermined amount of time. The treatment can also be achieved by alternating warming and cooling the thermal transfer region for a predetermined amount of time. The durations of warming and cooling can be adjusted accordingly depending on the outcome and response of the subject.

The warming and/or cooling the forehead region of the subject can be realized by using a thermal transfer fluid, a chemical heating or cooling element, a joule heating element, or a combination thereof.

In some embodiments, the method of treating neurological disorders and neuropsychiatric disorders and conditions provided herein includes maintaining the temperature of the thermal transfer region within a target temperature range of 10 to 28° C. for a first predetermined time period, and then maintaining the temperature of the thermal transfer region within a target temperature range of 37 to 42° C. for a second predetermined time period.

In some embodiments, the method of treating neurological disorders and neuropsychiatric disorders and conditions provided herein includes maintaining the temperature of the thermal transfer region within a target temperature range of 10 to 28° C. for a first predetermined time period, and then maintaining the temperature of the thermal transfer region within a target temperature range of 10 to 28° C. for a second predetermined time period.

The first predetermined time period can be any amount of time, for example, from about 10 minutes to about 3 hours, from about 10 minutes to about 6 hours, from about 10 minutes to about 12 hours, from about 10 minutes to about 16 hours, from about 10 minutes to about 18 hours, from about 10 minutes to about 24 hours, from 10 minutes to 36 hours, from about 10 minutes to about 48 hours, from 10 minutes to about 72 hours from 10 minutes to about 96 hours. The second predetermined time period can be any amount of time, for example, from about 10 minutes to about 3 hours, from about 10 minutes to about 6 hours, from about 10 minutes to about 12 hours, from about 10 minutes to about 16 hours, from about 10 minutes to about 18 hours, from about 10 minutes to about 24 hours, from 10 minutes to 36 hours, from about 10 minutes to about 48 hours, from 10 minutes to about 72 hours from 10 minutes to about 96 hours. In some instances, the first predetermined treatment time period is longer than the second predetermined treatment time period. In other instances, the first predetermined treatment time period is shorter than the second predetermined treatment time period. In certain instances, the first predetermined treatment time period is about the same as the second predetermined treatment time period.

The temperature or temperature range can be maintained continuously, periodically, or intermittently with regular or irregular time intervals.

In some embodiments, the method of treating neurological disorders and neuropsychiatric disorders and conditions provided herein includes maintaining the temperature of the thermal transfer region within a target temperature range that is between 10 and 28° C. for a predetermined time period, once a day for 1, 2, 3, 4, 5, 6, 7, 8, 9, 10, 11 or 12 weeks. The predetermined time period can be as short as 1 minute, but in general is at least 10 minutes. For example, the predetermined time period can be from about 10 minutes to about 24 hours.

In some embodiments, the method of treating neurological disorders and neuropsychiatric disorders and conditions provided herein includes maintaining the temperature of the thermal transfer region within a target temperature range that is between 10 and 28° C. for a predetermined time period, once every other day for 1, 2, 3, 4, 5, 6, 7, 8, 9, 10, 11 or 12 weeks. The predetermined time period can be as short as 1 minute, but in general is at least 10 minutes. For example, the predetermined time period can be from about 10 minutes to about 24 hours.

In some embodiments, the method of treating neurological disorders and neuropsychiatric disorders and conditions provided herein includes maintaining the temperature of the thermal transfer region within a target temperature range that is between 10 and 28° C. for a predetermined time period, once every other two days for 1, 2, 3, 4, 5, 6, 7, 8, 9, 10, 11 or 12 weeks. The predetermined time period can be as short as 1 minute, but in general is at least 10 minutes. For example, the predetermined time period can be from about 10 minutes to about 24 hours.

In some embodiments, the method of treating neurological disorders and neuropsychiatric disorders and conditions provided herein includes maintaining the temperature of the thermal transfer region within a target temperature range that is between 10 and 28° C. for a predetermined time period, once every other three days for 1, 2, 3, 4, 5, 6, 7, 8, 9, 10, 11 or 12 weeks. The predetermined time period can be as short as 1 minute, but in general is at least 10 minutes. For example, the predetermined time period can be from about 10 minutes to about 24 hours.

In some embodiments, the method of treating neurological disorders and neuropsychiatric disorders and conditions provided herein includes maintaining the temperature of the thermal transfer region within a target temperature range that is between 10 and 28° C. for a predetermined time period, twice a day for 1, 2, 3, 4, 5, 6, 7, 8, 9, 10, 11 or 12 weeks. The predetermined time period can be as short as 1 minute, but in general is at least 10 minutes. For example, the predetermined time period can be from about 10 minutes to about 12 hours, from about 10 minutes to about 18 hours, or from about 10 minutes to 23 hours. The total predetermined time period for maintaining a target temperature range can be 24 hours or less.

In some embodiments, the method of treating neurological disorders and neuropsychiatric disorders and conditions provided herein includes maintaining the temperature of the thermal transfer region within a target temperature range that is between 10 and 28° C. for a predetermined time period, twice a day every other day for 1, 2, 3, 4, 5, 6, 7, 8, 9, 10, 11 or 12 weeks. The predetermined time period can be as short as 1 minute, but in general is at least 10 minutes. For example, the predetermined time period can be from about 10 minutes to about 12 hours, from about 10 minutes to about 18 hours, or from about 10 minutes to 23 hours. The total predetermined time period for maintaining a target temperature range can be 24 hours or less.

In some embodiments, the method of treating neurological disorders and neuropsychiatric disorders and conditions provided herein includes maintaining the temperature of the thermal transfer region within a target temperature range that is between 10 and 28° C. for a predetermined time period, twice a day every other two days for 1, 2, 3, 4, 5, 6, 7, 8, 9, 10, 11 or 12 weeks. The predetermined time period can be as short as 1 minute, but in general is at least 10 minutes. For example, the predetermined time period can be from about 10 minutes to about 12 hours, from about 10 minutes to about 18 hours, or from about 10 minutes to 23 hours. The total predetermined time period for maintaining a target temperature range can be 24 hours or less.

In some embodiments, the method of treating neurological disorders and neuropsychiatric disorders and conditions provided herein includes maintaining the temperature of the thermal transfer region within a target temperature range that is between 10 and 28° C. for a predetermined time period, twice a day every other three days for 1, 2, 3, 4, 5, 6, 7, 8, 9, 10, 11 or 12 weeks. The predetermined time period can be as short as 1 minute, but in general is at least 10 minutes. For example, the predetermined time period can be from about 10 minutes to about 12 hours, from about 10 minutes to about 16 hours, from about 10 minutes to about 18 hours, or from about 10 minutes to 23 hours. The total predetermined time period for maintaining a target temperature range can be 24 hours or less.

In the twice a day treatment regimen, a predetermined amount of time is established for maintaining a first temperature or temperature range and a second temperature or temperature range. The predetermined time period for maintaining the first temperature or temperature range in a day can be the same as or different from the predetermined time period for maintaining the second temperature or temperature range. In some instances, the predetermined time period for maintaining the first temperature range is longer than the predetermined time period for maintaining the temperature or second temperature range during the day. In other instances, the predetermined time period for maintaining the first temperature or temperature range is shorter than the predetermined time period for maintaining the second temperature range during the day. In other instances, the predetermined time period for maintaining the first temperature or temperature range is about the same as the predetermined time period for maintaining the second temperature or temperature range during the day. The temperature or temperature range can be maintained continuously, periodically, or intermittently with regular or irregular time intervals.

In some embodiments, the method of treating neurological disorders and neuropsychiatric disorders and conditions provided herein includes maintaining the temperature of the thermal transfer region within a target temperature range that is between 10 and 28° C. for a predetermined time period, three times a day for 1, 2, 3, 4, 5, 6, 7, 8, 9, 10, 11 or 12 weeks. The predetermined time period can be as short as 1 minute, but in general is at least 10 minutes. For example, the predetermined time period can be from about 10 minutes to about 12 hours, from about 10 minutes to about 16 hours, from about 10 minutes to about 18 hours, or from about 10 minutes to 23 hours. The total predetermined time period for maintaining a target temperature range can be 24 hours or less.

In some embodiments, the method of treating neurological disorders and neuropsychiatric disorders and conditions provided herein includes maintaining the temperature of the thermal transfer region within a target temperature range that is between 10 and 28° C. for a predetermined time period, three times a day every other day for 1, 2, 3, 4, 5, 6, 7, 8, 9, 10, 11 or 12 weeks. The predetermined time period can be as short as 1 minute, but in general is at least 10 minutes. For example, the predetermined time period can be from about 10 minutes to about 12 hours, from about 10 minutes to about 16 hours, from about 10 minutes to about 18 hours, or from about 10 minutes to 23 hours. The total predetermined time period for maintaining a target temperature range can be 24 hours or less.

In some embodiments, the method of treating neurological disorders and neuropsychiatric disorders and conditions provided herein includes maintaining the temperature of the thermal transfer region within a target temperature range that is between 10 and 28° C. for a predetermined time period, three times a day every other two days for 1, 2, 3, 4, 5, 6, 7, 8, 9, 10, 11 or 12 weeks. The predetermined time period can be as short as 1 minute, but in general is at least 10 minutes. For example, the predetermined time period can be from about 10 minutes to about 12 hours, from about 10 minutes to about 16 hours, from about 10 minutes to about 18 hours, or from about 10 minutes to 23 hours. The total predetermined time period for maintaining a target temperature range can be 24 hours or less.

In some embodiments, the method of treating neurological disorders and neuropsychiatric disorders and conditions provided herein includes maintaining the temperature of the thermal transfer region within a target temperature range that is between 10 and 28° C. for a predetermined time period, three times a day every other three days for 1, 2, 3, 4, 5, 6, 7, 8, 9, 10, 11 or 12 weeks. The predetermined time period can be as short as 1 minute, but in general is at least 10 minutes. For example, the predetermined time period can be from about 10 minutes to about 12 hours, from about 10 minutes to about 16 hours, from about 10 minutes to about 18 hours, or from about 10 minutes to 23 hours. The total predetermined time period for maintaining a target temperature range can be 24 hours or less.

In the three times a day treatment regimen, a predetermined amount of time is established for maintaining a first temperature or temperature range, a second temperature or temperature range, and a third temperature or temperature range. The predetermined time period for maintaining the first temperature range in a day can be the same as or different from the predetermined time period for maintaining the second or third temperature or temperature range. In some instances, the predetermined time period for maintaining the first temperature or temperature range is longer than the predetermined time period for maintaining the second or third temperature or temperature range during the treatment. In other instances, the predetermined time period for maintaining the first temperature or temperature range is shorter than the predetermined time period for maintaining the second or third temperature or temperature range during the treatment. In other instances, the predetermined time period for maintaining the first temperature or temperature range is about the same as the predetermined time period for maintaining the second or third temperature or temperature range during the treatment. In other instances, the predetermined time is the same for maintaining the first, second and third temperature or temperature ranges. In other instances, the predetermined time period for maintaining the second temperature or temperature range is longer than the predetermined time period for maintaining the first or third temperature or temperature range during the treatment. In other instances, the predetermined time period for maintaining the third temperature or temperature range is longer than the predetermined time period for maintaining the second or first temperature or temperature range during the treatment. In other instances, the predetermined time period for maintaining the first temperature or temperature range is longer than the predetermined time period for maintaining the second temperature or temperature range, which is the same or longer than the predetermined time period for maintaining the third temperature or temperature range during the treatment. In other instances, the predetermined time period for maintaining the second temperature or temperature range can be longer than the predetermined time period for maintaining the first temperature range, which can be the same or longer than the predetermined time period for maintaining the third temperature or temperature range during the treatment. In another embodiment, the predetermined time period for maintaining the third temperature or temperature range can be longer than the predetermined time period for maintaining the second temperature or temperature range, which can be the same or longer than the predetermined amount of time for maintaining the first temperature or temperature range during the treatment. The temperature or temperature range can be maintained continuously, periodically, or intermittently with regular or irregular time intervals.

In some embodiments, the method of treating neurological disorders and neuropsychiatric disorders and conditions provided herein includes maintaining the temperature of the thermal transfer region within a target temperature range that is between 10 and 28° C. for a predetermined time period, once a week for 1, 2, 3, 4, 5, 6, 7, 8, 9, 10, 11, 12, 13, 14, 15, 16, 17, 18, 19, 20, 21, 22, 23, or 24 weeks. The treatment can be at any day of the week and can last more than 24 hours. The temperature or temperature range can be maintained continuously, periodically, or intermittently with regular or irregular intervals for the predetermined amount of time. The predetermined time period can be as short as 1 minute, but in general is at least 10 minutes. For example, the predetermined time period can be from about 10 minutes to about 12 hours, from about 10 minutes to about 16 hours, from about 10 minutes to about 18 hours, from about 10 minutes to 24 hours, from 10 minutes to 36 hours, from 10 minutes to 48 hours, from 10 minutes to 72 hours, or from 10 minutes to 96 hours.

In some embodiments, the method of treating neurological disorders and neuropsychiatric disorders and conditions provided herein includes maintaining the temperature of the thermal transfer region within a target temperature range that is between 10 and 28° C. for a predetermined time period twice a week for 1, 2, 3, 4, 5, 6, 7, 8, 9, 10, 11, 12, 13, 14, 15, 16, 17, 18, 19, 20, 21, 22, 23, or 24 weeks. The treatment can be on any single day of the week or any two separate times or days of the week. If the treatments are on two separate times or days of the week, it can last more than 24 hours. The temperature or temperature range can be maintained continuously, periodically, or intermittently with regular or irregular intervals for the predetermined amount of time. The predetermined time period can be as short as 1 minute, but in general is at least 10 minutes. For example, the predetermined time period can be from about 10 minutes to about 12 hours, from about 10 minutes to about 16 hours, from about 10 minutes to about 18 hours, from about 10 minutes to about 24 hours, from 10 minutes to 36 hours, from about 10 minutes to about 48 hours, from 10 minutes to about 72 hours.

In the twice a week treatment regimen, a predetermined amount of time is established for maintaining a first temperature or temperature range and a second temperature or temperature range. The predetermined time period for maintaining the first temperature range in a week can be the same as or different from the predetermined time period for maintaining the second temperature range. In some instances, the predetermined time period for maintaining the first temperature range is longer than the predetermined time period for maintaining the second temperature range during the day. In other instances, the predetermined time period for maintaining the first temperature range is shorter than the predetermined time period for maintaining the second temperature range. In other instances, the predetermined time period for maintaining the first temperature range is about the same as the predetermined time period for maintaining the second temperature range. The subject can be treated once each day for two separate days of the week. The subject can also be treated twice on a single day of the week. In other embodiments, the subject can be treated twice over a period of 2 days, 3 days, 4 days, 5 days, 6 days, or 7 days by adjusting the predetermined amount of time for maintaining the temperatures or temperature ranges on the subject to be treated. The temperature or temperature range can be maintained continuously, periodically, or intermittently with regular or irregular intervals.

In some embodiments, the method of treating neurological disorders and neuropsychiatric disorders and conditions provided herein includes maintaining the temperature of the thermal transfer region within a target temperature range that is between 10 and 28° C. for a predetermined time period, three times a week for 1, 2, 3, 4, 5, 6, 7, 8, 9, 10, 11, 12, 13, 14, 15, 16, 17, 18, 19, 20, 21, 22, 23, or 24 weeks. The treatment can be on any single day of the week or any three separate times or days of the week. If the treatments are on three separate times or days of the week, the time period for maintaining each temperature or temperature range can last more than 24 hours. The temperature or temperature range can be maintained continuously, periodically, or intermittently with regular or irregular intervals for the predetermined amount of time. The predetermined time period can be as short as 1 minute, but in general is at least 10 minutes. For example, the predetermined time period can be from about 10 minutes to about 12 hours, from about 10 minutes to about 16 hours, from about 10 minutes to about 18 hours, from about 10 minutes to about 24 hours, from 10 minutes to 36 hours, from about 10 minutes to about 48 hours, or from 10 minutes to about 72 hours.

In the three times a week treatment regimen, a predetermined amount of time is established for maintaining a first temperature or temperature range, a second temperature or temperature range, and a third temperature or temperature range. The predetermined time period for maintaining the first temperature range in a week can be the same as or different from the predetermined time period for maintaining the second or third temperature or temperature range. In some instances, the predetermined time period for maintaining the first temperature or temperature range is longer than the predetermined time period for maintaining the second or third temperature or temperature range during the treatment. In other instances, the predetermined time period for maintaining the first temperature or temperature range is shorter than the predetermined time period for maintaining the second or third temperature or temperature range during the treatment. In other instances, the predetermined time period for maintaining the first temperature or temperature range is about the same as the predetermined time period for maintaining the second or third temperature or temperature range during the treatment. In other instances, the predetermined time is the same for maintaining the first, second and third temperature or temperature ranges. In other instances, the predetermined time period for maintaining the second temperature or temperature range is longer than the predetermined time period for maintaining the first or third temperature or temperature range during the treatment. In other instances, the predetermined time period for maintaining the third temperature or temperature range is longer than the predetermined time period for maintaining the second or first temperature or temperature range during the treatment. In other instances, the predetermined time period for maintaining the first temperature or temperature range is longer than the predetermined time period for maintaining the second temperature or temperature range, which is the same or longer than the predetermined time period for maintaining the third temperature or temperature range during the treatment. In other instances, the predetermined time period for maintaining the second temperature or temperature range can be longer than the predetermined time period for maintaining the first temperature range, which can be the same or longer than the predetermined time period for maintaining the third temperature or temperature range during the treatment. In another embodiment, the predetermined time period for maintaining the third temperature or temperature range can be longer than the predetermined time period for maintaining the second temperature or temperature range, which can be the same or longer than the predetermined amount of time for maintaining the first temperature or temperature range during the treatment. In some embodiments, the subject can be treated once each day on three separate days of the week. In other embodiments, the subject can be treated three times on a single days of the week. In other embodiments, the subject can be treated twice in a single day and once on a separate day of the week. In other embodiments, the subject can be treated three times over a period of 2 days, 3 days, 4 days, 5 days, 6 days, or 7 days by adjusting the predetermined amount of time for maintaining the temperatures or temperature ranges on the subject to be treated. The temperature or temperature range can be maintained continuously, periodically, or intermittently with regular or irregular intervals.

In some embodiments, the method of treating neurological disorders and neuropsychiatric disorders and conditions provided herein includes maintaining the temperature of the thermal transfer region within a target temperature range that is between 10 and 28° C. for a predetermined time period, four times a week for 1, 2, 3, 4, 5, 6, 7, 8, 9, 10, 11, 12, 13, 14, 15, 16, 17, 18, 19, 20, 21, 22, 23, or 24 weeks. The treatment can be on any single day of the week or any four separate times or days of the week. If the treatments are on four separate times or days of the week, the time period for maintaining each temperature or temperature range can last more than 24 hours. The temperature or temperature range can be maintained continuously, periodically, or intermittently with regular or irregular intervals for the predetermined amount of time. The predetermined time period can be as short as 1 minute, but in general is at least 10 minutes. For example, the predetermined time period can be from about 10 minutes to about 12 hours, from about 10 minutes to about 16 hours, from about 10 minutes to about 18 hours, from about 10 minutes to about 24 hours, from 10 minutes to 36 hours, from about 10 minutes to about 48 hours, from 10 minutes to about 72 hours, or from 10 minutes to about 96 hours.

In the four times a week treatment regimen, a predetermined amount of time is established for maintaining a first temperature or temperature range, a second temperature or temperature range, a third temperature or temperature range, and a fourth temperature or temperature range. The predetermined time period for maintaining the first temperature range in a week can be the same as or different from the predetermined time period for maintaining the second, third or fourth temperature or temperature range. In some instances, the predetermined time period for maintaining the first temperature or temperature range is longer than the predetermined time period for maintaining the second, third or fourth temperature or temperature range during the treatment. In other instances, the predetermined time period for maintaining the first temperature or temperature range is shorter than the predetermined time period for maintaining the second, third or fourth temperature or temperature range during the treatment. In other instances, the predetermined time period for maintaining the first temperature or temperature range is about the same as the predetermined time period for maintaining the second or third or fourth temperature or temperature range during the treatment. In other instances, the predetermined time is the same for maintaining the first, second, third and fourth temperature or temperature ranges. In other instances, the predetermined time period for maintaining the second temperature or temperature range is longer than the predetermined time period for maintaining the first, third or fourth temperature or temperature range during the treatment. In other instances, the predetermined time period for maintaining the third temperature or temperature range is longer than the predetermined time period for maintaining the second, first or fourth temperature or temperature range during the treatment. In other instances, the predetermined time period for maintaining the fourth temperature or temperature range is longer than the predetermined time period for maintaining the second, first or third temperature or temperature range during the treatment. In other instances, the predetermined time period for maintaining the first temperature or temperature range is longer than the predetermined time period for maintaining the second temperature or temperature range, which is the same or longer than the predetermined time period for maintaining the third temperature or temperature range, which is longer or the same as maintaining the fourth temperature or temperature range during the treatment. In other instances, the predetermined time period for maintaining the second temperature or temperature range can be longer than the predetermined time period for maintaining the first temperature range, which can be the same or longer than the predetermined time period for maintaining the third temperature or temperature range during the treatment, which is the same or longer than the predetermined time period for maintaining the fourth temperature or temperature range during the treatment. In another embodiment, the predetermined time period for maintaining the third temperature or temperature range can be longer than the predetermined time period for maintaining the second temperature or temperature range, which can be the same or longer than the predetermined amount of time for maintaining the first temperature or temperature range, which is the same or longer than the predetermined time period for maintaining the fourth temperature or temperature range during the treatment. In another embodiment, the predetermined time period for maintaining the fourth temperature or temperature range can be longer than the predetermined time period for maintaining the third temperature or temperature range, which can be the same or longer than the predetermined amount of time for maintaining the second temperature or temperature range, which is the same or longer than the predetermined time period for maintaining the first temperature or temperature range during the treatment. In some embodiments, the subject can be treated four times in a single day of the week. In other embodiments, the subject can be treated twice each day on two separate days of the week. In other embodiments, the subject can be treated three times on a single day and once on a separate day of the week. In other embodiments, the subject can be treated once each day on four separate days of the week. In other embodiments, the subject can be treated four times over a period of 2 days, 3 days, 4 days, 5 days, 6 days, or 7 days by adjusting the predetermined amount of time for maintaining the temperatures or temperature ranges on the subject to be treated. The temperature or temperature range can be maintained continuously, periodically, or intermittently with regular or irregular intervals.

In some embodiments, the method of treating neurological disorders and neuropsychiatric disorders and conditions provided herein includes maintaining the temperature of the thermal transfer region within a target temperature range that is between 10 and 28° C. for a predetermined time period five times a week for 1, 2, 3, 4, 5, 6, 7, 8, 9, 10, 11, 12, 13, 14, 15, 16, 17, 18, 19, 20, 21, 22, 23, or 24 weeks. The treatment can be on any single day of the week or any five separate times or days of the week. If the treatments are on four separate times or days of the week, the time period for maintaining each temperature or temperature range can last more than 24 hours. The temperature or temperature range can be maintained continuously, periodically, or intermittently with regular or irregular intervals for the predetermined amount of time. The predetermined time period can be as short as 1 minute, but in general is at least 10 minutes. For example, the predetermined time period can be from about 10 minutes to about 12 hours, from about 10 minutes to about 16 hours, from about 10 minutes to about 18 hours, from about 10 minutes to about 24 hours, from 10 minutes to 36 hours, from about 10 minutes to about 48 hours, from 10 minutes to about 72 hours, from 10 minutes to about 96 hours, or from about 10 minutes to about 120 hours.

In the five times a week treatment regimen, a predetermined amount of time is established for maintaining a first temperature or temperature range, a second temperature or temperature range, a third temperature or temperature range, a fourth temperature or temperature range, and a fifth temperature or temperature range. The predetermined time period for maintaining the each temperature or temperature range in a week can be the same as or different. In some instances, the predetermined time is the same for maintaining the first, second, third, fourth and fifth temperatures or temperature ranges. In other instances, the predetermined time period for maintaining the first temperature or temperature range is longer than the predetermined time period for maintaining the second temperature or temperature range, which is the same or longer than the predetermined time period for maintaining the third temperature or temperature range, which is longer or the same as maintaining the fourth temperature or temperature range during the treatment, which is longer or the same as maintaining the fifth temperature or temperature range during the treatment. In other instances, the predetermined time period for maintaining the second temperature or temperature range can be longer than the predetermined time period for maintaining the first temperature range, which can be the same or longer than the predetermined time period for maintaining the third temperature or temperature range, which is the same or longer than maintaining the fourth temperature or temperature range, which is longer or the same as maintaining the fifth temperature or temperature range during the treatment during the treatment. In another embodiment, the predetermined time period for maintaining the third temperature or temperature range can be longer than the predetermined time period for maintaining the second temperature or temperature range, which can be the same or longer than the predetermined amount of time for maintaining the first temperature or temperature range, which is the same or longer than maintaining the fourth temperature or temperature range, which is longer or the same as maintaining the fifth temperature or temperature range during the treatment during the treatment. In another embodiment, the predetermined time period for maintaining the fourth temperature or temperature range can be longer than the predetermined amount of time for maintaining the fifth temperature or temperature range, which can be the same or longer than the predetermined time period for maintaining the third temperature or temperature range, which can be the same or longer than the predetermined amount of time for maintaining the second temperature or temperature range, which is the same or longer than the predetermined amount of time for maintaining the first temperature or temperature range during the treatment. In some embodiments, the subject can be treated five times in a single day of the week. In other embodiments, the subject can be treated once each day on five separate days of the week. In other embodiments, the subject can be treated twice in a single day and three times on another day of the week. In other embodiments, the subject can be treated twice in a single day and three times on three separate days of the week. In other embodiments, the subject can be treated twice on a single day and once each day on three separate days of the week. In other embodiments, the subject can be treated twice on a single day, once on a separate single day, and twice on a separate single day of the week. In other embodiments, the subject can be treated twice on a single day, once on a separate single day, and twice each day on two separate days of the week. In other embodiments, the subject can be treated five times over a period of 2 days, 3 days, 4 days, 5 days, 6 days, or 7 days by adjusting the predetermined amount of time for maintaining the temperatures or temperature ranges on the subject to be treated. The temperature or temperature range can be maintained continuously, periodically, or intermittently with regular or irregular intervals.

In some embodiments, the method of treating neurological disorders and neuropsychiatric disorders and conditions provided herein includes maintaining the temperature of the thermal transfer region within a target temperature range that is between 10 and 28° C. for a predetermined time period, six times a week for 1, 2, 3, 4, 5, 6, 7, 8, 9, 10, 11, 12, 13, 14, 15, 16, 17, 18, 19, 20, 21, 22, 23, or 24 weeks. The treatment can be on any single day of the week or any six separate times or days of the week. If the treatments are on four separate times or days of the week, the time period for maintaining each temperature or temperature range can last more than 24 hours. The temperature or temperature range can be maintained continuously, periodically, or intermittently with regular or irregular intervals for the predetermined amount of time. The predetermined time period can be as short as 1 minute, but in general is at least 10 minutes. For example, the predetermined time period can be from about 10 minutes to about 12 hours, from about 10 minutes to about 16 hours, from about 10 minutes to about 18 hours, from about 10 minutes to about 24 hours, from 10 minutes to 36 hours, from about 10 minutes to about 48 hours, from about 10 minutes to about 72 hours, from 10 minutes to about 96 hours, from about 10 minutes to about 120 hours or from about 10 minutes to about 144 hours.

In the six times a week treatment regimen, a predetermined amount of time is established for maintaining a first temperature or temperature range, a second temperature or temperature range, a third temperature or temperature range, a fourth temperature or temperature range, a fifth temperature or temperature range, and a sixth temperature or temperature range. The predetermined time period for maintaining each temperature or temperature range in a week can be the same as or different. In some instances, the predetermined time is the same for maintaining the first, second, third, fourth, fifth, and sixth temperatures or temperature ranges. In some embodiments, the subject can be treated six times in a single day of the week. In other embodiments, the subject can be treated once each day on six separate days of the week. In other embodiments, the subject can be treated twice in a single day on three separate days of the week. In other embodiments, the subject can be treated twice in a single day, once in a single day, and three times on three separate days of the week. In other embodiments, the subject can be treated twice on a single day, once in a single day and three times in a single day of the week. In other embodiments, the subject can be treated twice on a single day and three times on a separate single day of the week. In other embodiments, the subject can be treated once each day on two separate single days and three times on a third single day of the week. In other embodiments, the subject can be treated six times over a period of 2 days, 3 days, 4 days, 5 days, 6 days, or 7 days by adjusting the predetermined amount of time for maintaining the temperatures or temperature ranges on the subject to be treated. The temperature or temperature range can be maintained continuously, periodically, or intermittently with regular or irregular intervals.

In some embodiments, the method of treating neurological disorders and neuropsychiatric disorders and conditions provided herein include maintaining the temperature of the thermal transfer region within a target temperature range by keeping the thermal transfer region at a particular temperature for a predetermined amount of time. For example, the method includes maintaining the temperature of the thermal transfer region at 10° C. for a first predetermined amount of time, 11° C. for a second predetermined amount of time, 12° C. for a third predetermined amount of time, 13° C. for a fourth predetermined amount of time, and 14° C. for a fifth predetermined amount of time within a 24-hour time period. In other embodiments, the method includes maintaining the temperature of the thermal transfer region at 10° C. for a first predetermined amount of time, 11° C. for a second predetermined amount of time, 12° C. for a third predetermined amount of time, 13° C. for a fourth predetermined amount of time, and 14° C. for a fifth predetermined amount of time within a 48-hour time period. In other embodiments, the method includes maintaining the temperature of the thermal transfer region at 10° C. for a first predetermined amount of time, 11° C. for a second predetermined amount of time, 12° C. for a third predetermined amount of time, 13° C. for a fourth predetermined amount of time, and 14° C. for a fifth predetermined amount of time within a 72-hour time period.

The temperature can be maintained for a predetermined amount of time during the subject's sleep or awake period, or both the subject's sleep and awake periods. In some embodiments, the target temperature range of the thermal transfer region is maintained for the subject's entire sleep period. In other embodiments, the target temperature range of the thermal transfer region is maintained for the subject's entire awake period.

The method of treating neurological disorders and neuropsychiatric disorders and conditions provided herein can also be applied to a subject who suffers from insomnia.

Any of the apparatuses (devices and systems) described herein may be configured to operate (or include as part of their operation) a gradual increase/decrease of the temperature (e.g., 'ramping') over a predetermined amount of time. In any of the variations described herein, the temperature may be 'ramped' from ambient to the target temperature, or target temperature range. In general, when a target temperature is described here, it is understood to be a target temperature range, e.g., +/−a range of temperatures centered on the target temperature, where the range may be a between about 0.5 degrees (e.g., +/−0.5° C.), 1 degree (+/−1° C.), 2 degree (+/−2° C.), 3 degree (+/−3° C.), 4 degree (+/−4° C.), 5 degree (+/−5° C.), etc. In some variations the target temperature range may be specified (e.g., between about 10° C. and 28° C. (inclusive), between about 11° C. and 28° C., between about 12° C. and 28° C., between about 13° C. and 28° C., between about 14° C. and 28° C., between about 15° C. and 28° C., between about 16° C. and 28° C., between about 17° C. and 28° C., between about 18° C. and 28° C., between about 19° C. and 28° C., between about 20° C. and 28° C., etc.

For example, in some variations the apparatus may be configured to include an alarm-clock (or 'wakeup') feature in which, at some predetermined/user selected time, the temperature of the applicator is changed (e.g., increased or decreased) to a predetermined temperature (e.g., ambient temperature) to stimulate the subject to wake up. For example, in some variations, the temperature may be set to a range centered on approximately 25° C. (or 30° C., etc.). This temperature may aid the subject in waking up.

Examples

Figure 13A:
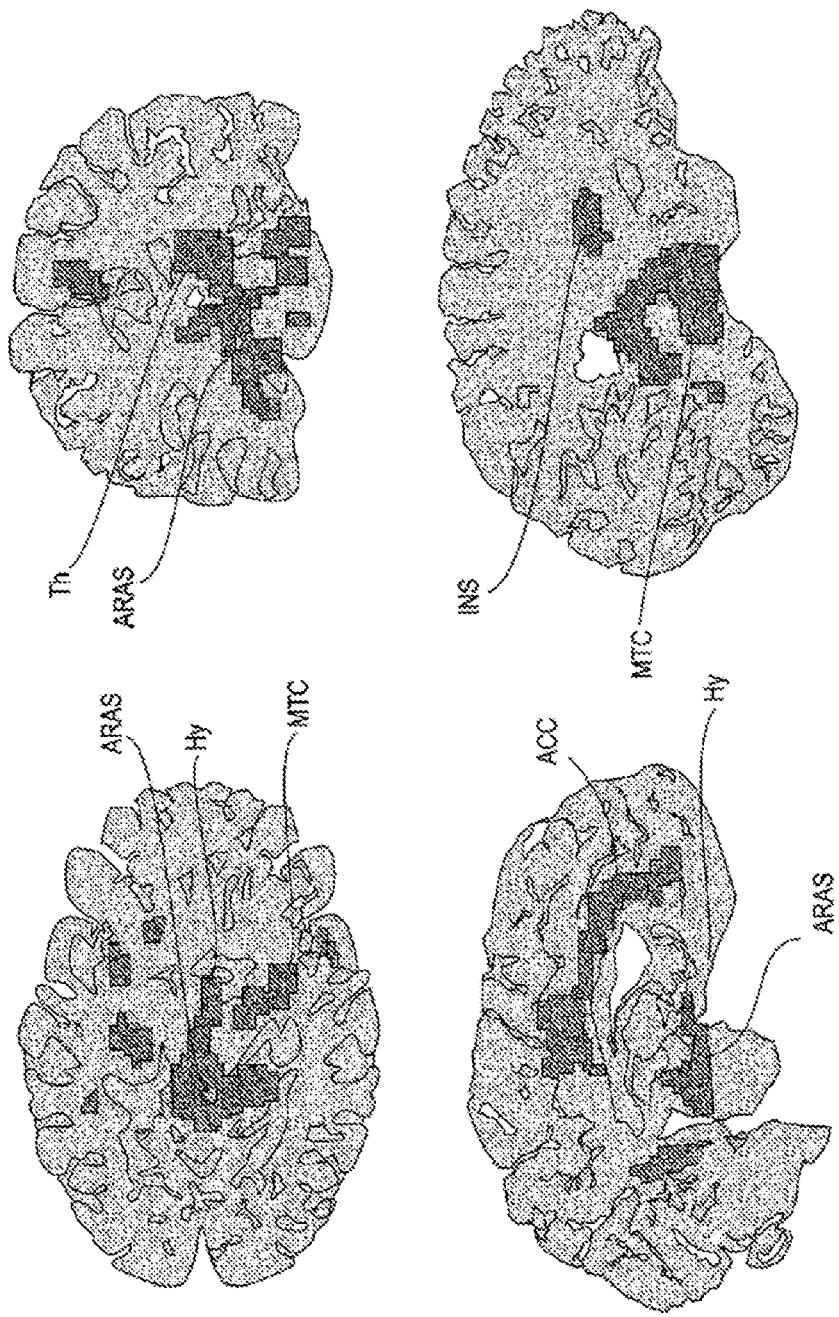
FIG. 13A illustrates brain regions where insomnia patients do not show as great of a decline in relative metabolism from waking to sleep.
Figure 13B:
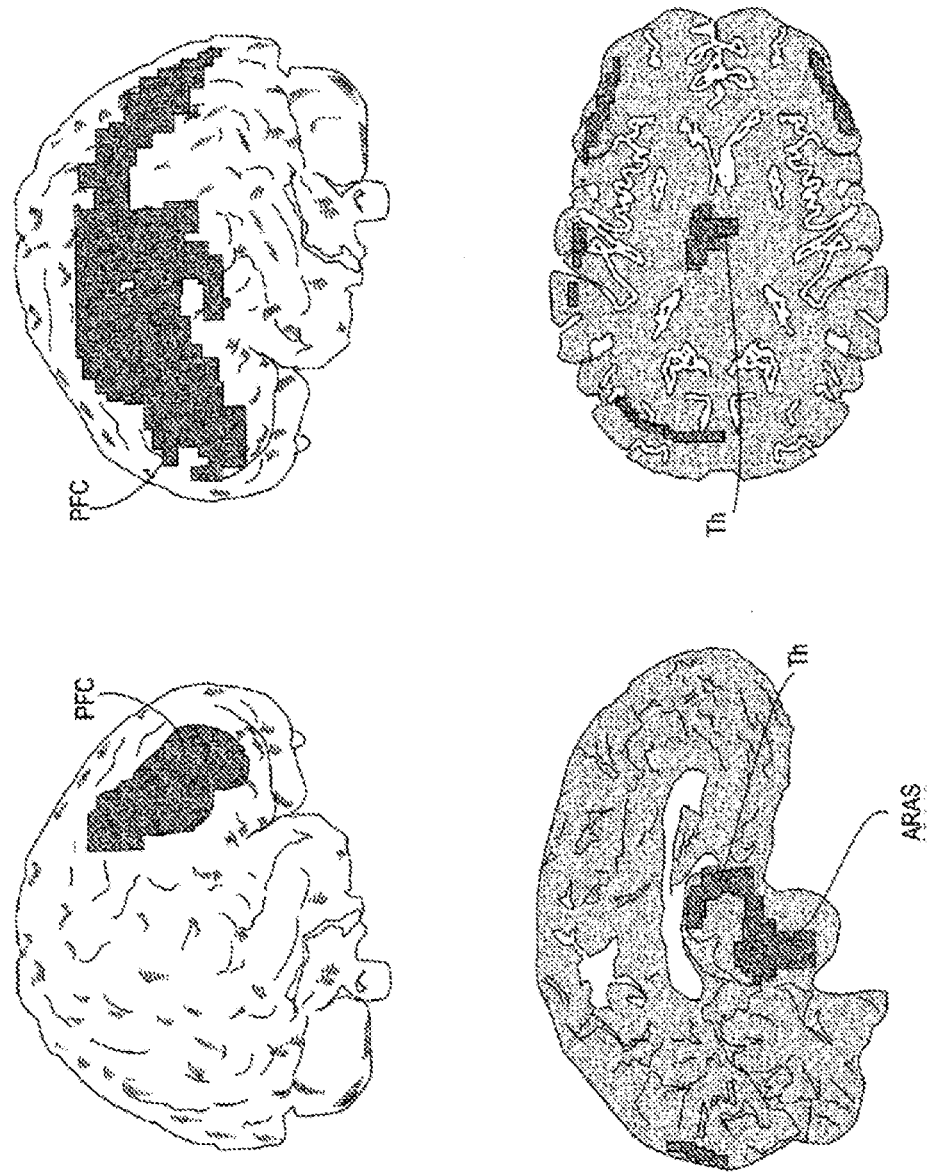
FIG. 13B shows brain regions where relative metabolism is decreased in insomnia patients.

A study of patients suffering from a neuropsyciatric disorder, including insomnia, was performed to investigate how these normal changes in brain metabolism become disturbed in these patients. For example, insomnia patients and healthy subjects completed regional cerebral glucose metabolic assessments during both waking and NREM sleep using [18F]fluoro-2-deoxy-D-glucose positron emission tomography (PET). Insomnia patients showed increased global cerebral glucose metabolism during sleep and wakefulness. A group x state interaction analysis confirmed that insomnia subjects showed a smaller decrease than did healthy subjects in relative metabolism from waking to NREM sleep in the ascending reticular activating system, hypothalamus, thalamus, insular cortex, amygdala and hippocampus and in the anterior cingulate and medial prefrontal cortices (as shown in FIGS. 13A and 13B). While awake, in relation to healthy subjects, insomnia subjects showed relative hypometabolism in a broad region of the frontal cortex bilaterally, left hemispheric superior temporal, parietal and occipital cortices, the thalamus, hypothalamus and brainstem reticular formation. This study demonstrated that subjectively disturbed sleep in insomnia patients is associated with increased brain metabolism. The inability of the insomniac patients to fall asleep may be related to a failure of arousal mechanisms to decline in activity from waking to sleep. Further, their daytime fatigue may reflect decreased activity in prefrontal cortex that results from inefficient sleep. These findings suggest interacting neural networks in the neurobiology of insomnia. These include a general arousal system (ascending reticular formation and hypothalamus), an emotion regulating system (hippocampus, amygdala and anterior cingulate cortex), and a cognitive system (prefrontal cortex). Notably, ascending arousal networks are functionally connected to cortical regions involved in cognitive arousal at the cortical level which can feedback and modulate more primitive brainstem and hypothalamic arousal centers. A medical device that alters metabolism in one or more portions of this network could benefit insomnia patients and produce more restful sleep.

A second study in insomnia patients was conducted to clarify the cerebral metabolic correlates of wakefulness after sleep onset (WASO) in primary insomnia patients testing the hypothesis that insomnia subjects with more WASO would demonstrate increased relative metabolism especially in the prefrontal cortex given the role of this region of the brain in restorative sleep and in cognitive arousal. Fifteen patients who met DSM-IV criteria for primary insomnia completed 1-week sleep diary (subjective) and polysomnographic (objective) assessments of WASO and regional cerebral glucose metabolic assessments during NREM sleep using [18F] fluoro-2-deoxy-D-glucose positron emission tomography (PET). Both subjective and objective WASO positively correlated with NREM sleep-related cerebral glucose metabolism in the pontine tegmentum and in thalamocortical networks in a frontal, anterior temporal, and anterior cingulate distribution. These effects may result from increased activity in arousal systems during sleep and/or to activity in higher order cognitive processes related to goal-directed behavior, conflict monitoring, emotional awareness, anxiety and fear. These processes are thought to be regulated by activity of the prefrontal cortex. A medical device that facilitates the normal reduction in relative metabolism in the prefrontal cortex during sleep could benefit insomnia patients.

As described above, cerebral hypothermia has been utilized in other medical disciplines as a means to reduce metabolic activity in the brain. Theoretical models suggest that application of a cooling stimulus at the scalp surface will cool and subsequently reduce metabolism in the underlying superficial cortex. These observations raised the possibility that a medical device that produced regional cooling to the scalp over the area of the prefrontal cortex, may reduce the hypermetabolism in that region in insomnia patients, allowing them to transition to sleep more easily and to subsequently obtain more restful sleep across the night. It is also conceivable that these cortical effects may have downstream effects on brainstem and hypothalamic centers of sleep/arousal regulation.

Interestingly preliminary work in other types of neuropsychiatric patients, including patient's having both insomnia and anxiety disorders and/or insomnia and stress disorders show similar results. Increased cortical activity, particularly during waking periods, that may be responsive to regional cooling, as described above.

Figure 14:
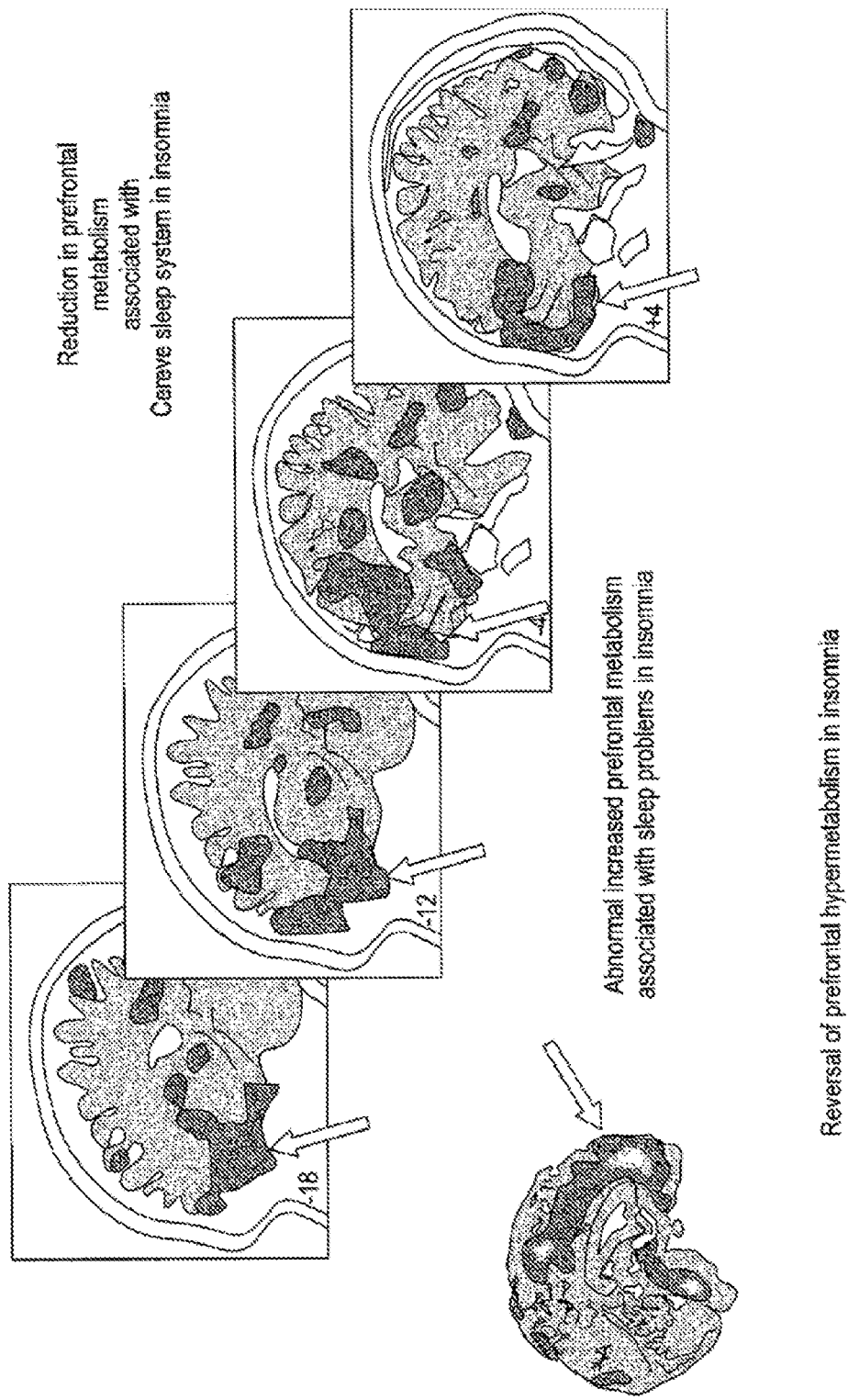
FIG. 14 shows PET scans of a patient undergoing treatment using localized cooling (e.g., resulting in frontal hypothermia) and illustrating a reversal of prefrontal hypermetabolism.

A device was constructed to test the application of regional hypothermia applied to the skin over the prefrontal cortex as a method of treating patient's. The device itself included a custom sized headpiece to fit the area of the scalp over the frontal cortex that circulated varying temperature fluids and a programmable cooling chamber/pump that provided the cooling and power for circulating the fluid to the headpiece (similar to that shown, e.g., in FIGS. 1-6). A study was performed to determine if the device lowered cerebral metabolism in the prefrontal cortex in insomnia patients. The study compared an active treatment (device at 14° C.) vs. a normothermic device comparison (control). Outcome measures included regional cerebral metabolism during sleep as measured by [18F]-FDG PET. 148 subjects were screened, 12 completed sleep studies, and 8 completed all PET imaging studies The data showed that the device reduced cerebral metabolism especially in the prefrontal cortex underneath the device. FIG. 14 illustrate some of the findings, and show trends towards reductions in whole brain metabolism, reductions in relative regional metabolism (highlighted regions of FIG. 14), especially in the prefrontal cortex, an increase in sleepiness and reduction in arousal while the device was worn for 60 minutes prior to bedtime, reductions in minutes of waking, increases in EEG delta spectral power and a reduction in core body temperature around the sleep onset period.

Significantly and surprisingly, 9 of 12 (75%) insomnia patients reported positive subjective effects of the device. All subjects encouraged further development of the device based on their experiences and all subjects easily understood/accepted the therapeutic concept for the treatment of their insomnia. They also reported: (1) a clear preference for the device over pills; (2) the device decreased distracting thoughts prior to getting in to bed; (3) the device facilitated sleep maintenance; (4) they experienced a subjective surprise that sleep passed without awareness; and (5) their sleep felt refreshing.

Figure 15:
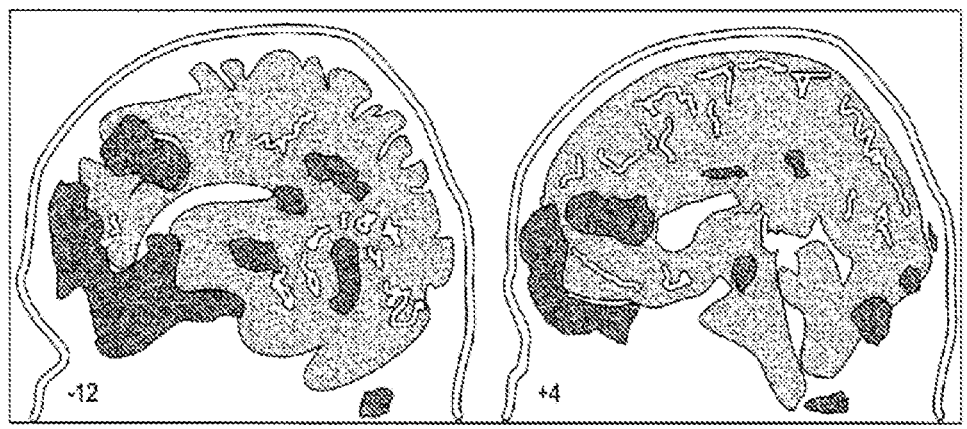
FIG. 15 is a side-by-side comparison of PET scans showing a reduction in regional metabolism in patients treated with localized cooling (e.g., resulting in prefrontal hypothermia) as described herein.

FIG. 15 shows the results of a comparison of regional cerebral metabolism during NREM sleep between two conditions, an active condition (wearing the device at 14 degrees C. for 60 minutes prior to getting into bed and continuing during sleep until the time of PET measurement at 20-40 minutes following sleep onset) and a control condition (wearing the device at a thermoneutral 30 degrees C. for 60 minutes prior to getting into bed and continuing during sleep until the time of PET measurement at 20-40 minutes following sleep onset) in primary insomnia patients. The brain regions highlighted in blue on two different sections through the brain show the areas of the brain, especially in the frontal cortex in the area underneath the device placement, where metabolism was significantly decreased in the active condition vs. the control condition.

The exemplary study above, while applied primarily to insomnia patients, illustrates the physiological effectiveness of regional cooling of the forehead resulting in significant changes in (regional) brain metabolism, and may be seen in both waking and asleep patients, including patients having any of the other neuropsychiatric disorders described herein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method for treating a neurological disorder in a patient, the method comprising:
   securing a thermal transfer region of an applicator in contact with the forehead of the patient so that the thermal transfer region does not contact the periorbital region of the patient's face; and
   maintaining the temperature of the thermal transfer region within a target temperature range that is between 10° C. and 28° C.; and
   thereby treating the neurological disorder,
   wherein the neurological disorder is one of depression, anxiety, posttraumatic stress disorder (PTSD) attention deficit hyperactivity disorder (ADHD), Obsessive Compulsive Disorder (OCD), and autism.

2. The method of claim 1, wherein the neurological disorder is one of: depression, anxiety, posttraumatic stress disorder (PTSD) and attention deficit hyperactivity disorder (ADHD).

3. The method of claim 1, wherein the neurological disorder is posttraumatic stress disorder (PTSD).

4. The method of claim 1, wherein the neurological disorder is Obsessive Compulsive Disorder (OCD).

5. The method of claim 1, wherein the neurological disorder is autism.

6. The method of claim 1, wherein maintaining the temperature comprises adjusting the temperature based on one or more feedback inputs.

7. The method of claim 6, wherein the one or more feedback inputs is one or more of: sensed motion, Electroencephalography (EEG), and electromyography (EMG).

8. The method of claim 1, wherein maintaining comprises maintaining the temperature of the thermal transfer region within the target temperature range for a first predetermined time period of between 10 minutes and 12 hours.

9. The method of claim 1, wherein maintaining comprises maintaining the temperature of the thermal transfer region within the target temperature range for a first predetermined time period of between 10 minutes and 4 hours.

10. The method of claim 1, wherein maintaining comprises maintaining the temperature of the thermal transfer region within the target temperature range for a first predetermined amount of time and then maintaining the temperature of the thermal transfer region within a target temperature range of 25 to 36° C. for a second predetermined amount of time.

11. The method of claim 1, wherein maintaining comprises maintaining the temperature of the thermal transfer region within the target temperature range for a predetermined amount of time that is greater than 15 minutes for at least once a day for between 1-12 weeks.

12. The method of claim 1, wherein maintaining comprises maintaining the temperature of the thermal transfer region within the target temperature range for a predetermined amount of time that is greater than 15 minutes for more than 2 times per week.

13. The method of claim 1, wherein maintaining the temperature of the thermal transfer region comprises maintaining the temperature while the patient is awake.

14. The method of claim 1, wherein the maintaining further comprises cooling the thermal transfer region for a predetermined amount of time using one or more of: a thermal transfer fluid, a chemical heating or cooling element, a thermoelectric temperature regulator, and a joule heating element.

15. A method for treating a neurological disorder in a patient, the method comprising:
    applying noninvasive, regional brain cooling to a region of a patient's head over a forehead and a temporal region of the patient's skull to locally cool the patient's forehead and the patient's temporal region by applying a temperature of between 10° C. and 28° C.; and
    maintaining the applied temperature between 10° C. and 28° C. to reduce brain metabolism in one or more of the patient's frontal cortex, prefrontal cortex and temporal cortex to treat the neurological disorder,
wherein the neurological disorder is one of: posttraumatic stress disorder (PTSD), obsessive compulsive disorder (OCD), autism, depression, anxiety, and attention deficit hyperactivity disorder (ADHD).

16. The method of claim 15, wherein the neurological disorder is one of: depression, anxiety, and attention deficit hyperactivity disorder (ADHD).

17. The method of claim 15, wherein the neurological disorder is posttraumatic stress disorder (PTSD).

18. The method of claim 15, wherein the neurological disorder is Obsessive Compulsive Disorder (OCD).

19. The method of claim 15, wherein the neurological disorder is autism.

20. The method of claim 15, wherein maintaining comprises maintaining the temperature of the thermal transfer region within the target temperature range for a first predetermined time period of between 10 minutes and 12 hours.

21. The method of claim 15, wherein the maintaining the applied temperature comprises maintaining the temperature for a predetermined time period of between 10 minutes and 4 hours.

22. The method of claim 15, wherein the maintaining the applied temperature comprises maintaining the temperature for a first predetermined amount of time and then maintaining the applied temperature within a target temperature range of 25 to 36° C. for a second predetermined amount of time.

23. The method of claim 15, wherein the maintaining the applied temperature comprises maintaining for a predetermined amount of time that is greater than 15 minutes for at least once a day for between 1-12 weeks.

24. The method of claim 15, wherein maintaining the applied temperature comprises maintaining for a predetermined amount of time that is greater than 15 minutes for more than 2 times per week.

25. The method of claim 15, wherein maintaining the applied temperature comprises maintaining the applied temperature while the patient is awake.

26. The method of claim 15, wherein maintaining comprises cooling for a predetermined amount of time using one or more of: a thermal transfer fluid, a chemical heating or cooling element, a thermoelectric temperature regulator, and a joule heating element.

27. A method for treating a neurological disorder in a patient, the method comprising:
securing a thermal transfer region of an applicator in contact with the forehead of the patient so that the thermal transfer region does not contact the periorbital region of the patient's face; and
maintaining the temperature of the thermal transfer region within a target temperature range to modify brain metabolism; and
thereby treating the neurological disorder,
wherein the neurological disorder is one of depression, anxiety, posttraumatic stress disorder (PTSD) attention deficit hyperactivity disorder (ADHD), Obsessive Compulsive Disorder (OCD), and autism.

28. The method of claim 27, wherein the neurological disorder is one of: depression, anxiety, posttraumatic stress disorder (PTSD) and attention deficit hyperactivity disorder (ADHD).

29. The method of claim 27, wherein the neurological disorder is posttraumatic stress disorder (PTSD).

30. The method of claim 27, wherein the neurological disorder is Obsessive Compulsive Disorder (OCD).

31. The method of claim 27, wherein the neurological disorder is autism.

32. The method of claim 27, wherein maintaining the temperature comprises adjusting the temperature based on one or more feedback inputs.

33. The method of claim 32, wherein the one or more feedback inputs is one or more of: sensed motion, Electroencephalography (EEG), and electromyography (EMG).

34. The method of claim 27, wherein maintaining comprises maintaining the temperature of the thermal transfer region within the target temperature range for a first predetermined time period of between 10 minutes and 12 hours.

35. The method of claim 27, wherein maintaining comprises maintaining the temperature of the thermal transfer region within the target temperature range of between 0° C. and 40° C.

36. The method of claim 27, wherein maintaining comprises maintaining the temperature of the thermal transfer region within the target temperature range for a predetermined amount of time that is greater than 15 minutes for at least once a day for between 1-12 weeks.

37. The method of claim 27, wherein maintaining the temperature of the thermal transfer region comprises maintaining the temperature while the patient is awake.

* * * * *

UNITED STATES PATENT AND TRADEMARK OFFICE
CERTIFICATE OF CORRECTION

PATENT NO. : 11,684,510 B2
APPLICATION NO. : 16/151243
DATED : June 27, 2023
INVENTOR(S) : Eric A. Nofzinger Page 1 of 1

It is certified that error appears in the above-identified patent and that said Letters Patent is hereby corrected as shown below:

In the Claims

Column 50, Line 6, Claim 1, delete "(PTSD)" and insert -- (PTSD), --

Column 52, Line 11, Claim 52, delete "(PTSD)" and insert -- (PTSD), --

Signed and Sealed this
Fifteenth Day of August, 2023

Katherine Kelly Vidal
*Director of the United States Patent and Trademark Office*